US009181573B2

(12) United States Patent
Van Der Laan et al.

(10) Patent No.: US 9,181,573 B2
(45) Date of Patent: Nov. 10, 2015

(54) METHOD FOR IMPROVING THE YIELD OF A POLYPEPTIDE

(75) Inventors: Jan Metske Van Der Laan, Breda (NL); Liang Wu, Delft (NL); Johannes Andries Roubos, Pijnacker (NL); Lucie Parenicova, Den Haag (NL); Alrik Pieter Los, 's-Gravenhage (NL); Noel Nicolaas Maria Elisabeth Van Peij, Delfgauw (NL); Jan Herman Pel, Terschuur (NL)

(73) Assignee: DSM IP ASSETS B.V., Heerlen (NL)

( * ) Notice: Subject to any disclaimer, the term of this patent is extended or adjusted under 35 U.S.C. 154(b) by 387 days.

(21) Appl. No.: 13/255,425

(22) PCT Filed: Mar. 8, 2010

(86) PCT No.: PCT/EP2010/052918
§ 371 (c)(1),
(2), (4) Date: Sep. 8, 2011

(87) PCT Pub. No.: WO2010/102982
PCT Pub. Date: Sep. 16, 2010

(65) Prior Publication Data
US 2011/0318752 A1    Dec. 29, 2011

(30) Foreign Application Priority Data

Mar. 10, 2009    (EP) ..................................... 09154783

(51) Int. Cl.
*G06F 19/22*    (2011.01)
*C12P 21/02*    (2006.01)

(52) U.S. Cl.
CPC ..................................... *C12P 21/02* (2013.01)

(58) Field of Classification Search
CPC .. C07K 2317/24; C07K 2317/94; C12P 1/02; G06F 19/16; G06F 19/22; G06Q 99/00
See application file for complete search history.

(56) References Cited

U.S. PATENT DOCUMENTS

2009/0286280 A1    11/2009    Roubos et al.

FOREIGN PATENT DOCUMENTS

| WO | 96/05228 | 2/1996 |
| WO | 02/055717 | 7/2002 |
| WO | 2008/000632 | 1/2008 |

OTHER PUBLICATIONS

Gouka et al., "Efficient Production of Secreted Proteins by *Aspergillus*: Progress, Limitations and Prospects," Appl. Microbiol. Biotechnol., vol. 47, pp. 1-11, (1997).
International Search Report of PCT/EP2010/052918 Mailed Jul. 19, 2010.
Written Opinion of PCT/EP2010/052918 Mailed Jul. 19, 2010.
Tsang et al, "Analytical and computational approaches to define the *Aspergillus niger* secretome", Fungal Genetics and Biology, Elsevier Inc., vol. 18, No. 2, pp. 342-348, 2008.
Webb, Andrew R. "Statistical Pattern Recognition" 2nd Edition, John Wiley & Sons Ltd., 2000.
Bleasby, Alan, "EMBOSS Pepstats", EMBOSS Wiki, European Bioinformatics Institute, Date Accessed: Jan. 14, 2014, http:emboss.sourceforge.net/apps/cvs/emboss/apps/pepstats.hml.
Kyte, Jack et al., "A Simple Method for Displaying the Hydropathic Character of a Protein", Department of Chemistry for University of California, J. Mol. Biol., Academic Press Inc., vol. 157, pp. 105-132, 1982.
Ikai, Atsushi, "Thermostability and Aliphatic Index of Globular Proteins", Department of Biophysics and Biochemistry of the University of Tokyo, J. Biochem, vol. 88, pp. 1895-1898, 1980.
Gaseiger et al, "Protein identification and Analysis Tools on the ExPASy Server" ,The Proeomics Protocols Handbook, Humana Press Inc., pp. 571-617, 2005.
Peterson, et al., "NetSurfP ver. 1.1-Protein Surface Accessibility and Secondary Structure Predictions", BMC Structural Biology 2009, 9:51 doi:10.1186/1472-6807-9-51, Date Web Accessed: Jan. 15, 2014, http://www.cbs.dtu.dk/services/NetSurfP/.
Connolly, Michael L., "Analytical Molecular Surface Calculation", Department of Molecular Biology: Research Institute of Scripps Clinic, J. Applied Crystallography,16.5, pp. 548-558, 1983.
Chothia, Cyrus, "The Nature of the Accessible and Buried Surfaces in Proteins", Service de Biochimie Cellulaire, J. Mol. Biol., vol. 105, pp. 1-12, 1976.
Ahmad et al. "Real Value Prediction of Solvent Accessibility From Amino Acid Sequence", Proteins: Structure, Function, and Genetics 50:629-635, RIKEN Tsukuba Institute, 2003.
Bent Peterson et al., "A generic method for assignment of reliability scores applied to solvent accessibility predictions", BMC Structural Biology 9:51, BioMed Central Ltd., 2009.
Dor et al. "Real-SPINE: An Integrated System of Neural Networks for Real-Value Prediction of Protein Structural Properties", Wiley InterScience, Proteins: Structure, Function, and Bionformatics, vol. 68 No. 1, pp. 76-81, 2007.
Faraggi et al., "Improving the prediction accuracy of residue solvent accessibility and real-value backbone torsion angles of proteins by guided-learning through a two-layer neural network" Proteins, vol. 74.1 pp. 847-856, 2009.
Kruskal, Joseph, "An Overview of Sequence Comparison: Time Warps, String Edits, and Macromolecules", Society for Industrial and Applied Mathematics, SIAM REVIEW, An over view of sequence comparison: time warps, strings edits and macromolecules, vol. 25, No. 2, pp. 201-237, 1983.
D. Sankoff and J. Kruskal, Addison-Wesling, Reading, Massachusetts, "Theory and Practice of Sequence Comparison: Time-Warps, Strings Edits, and Macromolecules", pp. 1-44, 1983.
Needleman et al, "A General Method Applicable to the Search for Similarities in the Amino Acid Sequence of Two Proteins", Department of Biochemistry of Northwestern University, J. Mol. Biol vol. 48, No. 2, pp. 443-453, 1970.
Kuhlman et al, Design of a Novel Globular Protein Fold with Atomic-Level Accuracy, Resarch Articles, Science, vol. 302, pp. 364-1368, 2003.

(Continued)

*Primary Examiner* — Mary Zeman
(74) *Attorney, Agent, or Firm* — Miles and Stockbridge

(57) ABSTRACT

The present invention relates to a method for improving protein yield. The method comprises modifying the value of a set of relevant protein features to fall within an optimal range or to become more close to an optimal value for one or more protein features in the eukaryotic host.

16 Claims, 9 Drawing Sheets

(56) References Cited

OTHER PUBLICATIONS

Dahiyat et al. "De Novo Protein Design: Towards Fully Automated Sequence Selection", J. Mol. Biol., vol. 273 v.4, pp. 789-796, 1997.
Baker, David, "Prediction and design of macromolecular structures and ineractions", Philosophical Transactions of the Royal Society B, pp. 361 and 459-463, 2006.
Benita et al, "Analysis of High Throughout Protein Expression in *Escherichia coli*" Molecular and Cellular Proteomics 5.9, pp. 567-1580, The American Society for Biochemistry and Molecular Biology, Inc., 2006.
http://en.wikipedia.org/wiki/Homology_Modeling (archived version as of Jan. 14, 2009).
http://en.wikipedia.org/wiki/Protein_structure_prediction_software (archived version as of Feb. 10, 2009).
Zhang, Yang, "Progress and challenges in protein structure prediction", ScienceDirect, Current Opinion in Structural Biology, Elesevier, vol. 18, pp. 342-348, 2008.
Richards, Frederic M., "Areas, Volumes, Packing, and Protein Structure", Department of Molecular Biophysics and Biochemistry of Yale Unveristy, Annual Reviews Inc., Annu. Rev. Biophys. Bioeng vol. 6, pp. 151-176, 1997.
http://en.wikipedia.org/wiki/Accessible_surface_area (archived version as of Jan. 27, 2009).
"Statistics Toolbox 7User's Guide", revised for Matlab v. 7.5, release R2011, Mathworks, 2011.
"Bioinformatics Toolbox User's Guide", revised for Matlab 4.3.1, release R2013b, Mathworks, 2013.
Wu et al., "Exploring biological design principles for improving recombinant protein production," presented at International Conference on Systems Biology held in Heidelberg-Mannheim, Germany, Aug. 28-Sep. 1, 2011.
van der Laan, "Engineering nature's enzyme repertoire for food and pharma," presented at EMBO Conference "Catalytic Mechanisms by Biological Systems" Oct. 7-10, 2012, Groningen, The Netherlands.

SEQUENCE LISTING

<160> NUMBER OF SEQ ID NOS: 30

<210> SEQ ID NO 1
<211> LENGTH: 1137
<212> TYPE: DNA
<213> ORGANISM: Artificial Sequence
<220> FEATURE:
<223> OTHER INFORMATION: Codon optimized sequence

<400> SEQUENCE: 1

```
ttcttaggta agatcgctaa gaacccagaa gcctctatga acgtttccca aatgatttct      60
tactggggtt acccatctga aatgcacaag gtcattaccg ctgacggtta cattttgcaa     120
gtttaccgta tcccacacgg taagaacaac gctaaccatt tgggtcaaag accagttgtc     180
tttttgcaac acgttttatt gggttccgct actaactgga tctccaattt gccaaagaac     240
tctctaggtt tcttgttggc tgatgctggt tacgatgtct ggttaggtaa ctctagaggt     300
aacacctggg ctcaagaaca cttgtactac tctccagact ccccagaatt ctgggctttc     360
tccttcgacg aaatggctga atacgactta ccatctacta tcgacttcat tttgagaaga     420
actggtcaaa agaaattgca ttacgttggt cactcccaag tactactat cggtttcatt      480
gccttctcca cctcccaac cttggctgaa aagatcaagg tcttctacgc tttagcccca     540
gttgctactg ttaagtacac caaatctttg ttcaacaaat tggctttgat cccacacttc     600
ttgttcaaga ttatctttgg tgacaagatg ttctatccac acaccttttt ggaacaattc     660
ttgggtgtcg aaatgtgttc tagagaaacc ttggatgtct tgtgtaagaa cgctttattc     720
gctatcactg gtgttgacaa caagaacttt aacatgtcta gattggatgt ttacattgcc     780
cacaacccag ccggtacctc cgtccaaaac accttgcact ggagacaagc tgttaagtct     840
ggtaagttcc aagccttcga ctggggtgcc ccataccaaa acttgatgca ctaccaccaa     900
ccaactcctc caatttacaa tttgaccgct atgaacgttc caattgccgt ctggtccgct     960
gataacgatt tgctagctga ccctcaagat gtcgacttct tgttgtctaa gttgtctaac    1020
ttgatctacc acaaggaaat cccaaactac aaccatttgg atttcatctg ggctatggac    1080
gctccacaag aagtttacaa cgaaatcgtc tctttgatgg ctgaagacaa gaaataa      1137
```

<210> SEQ ID NO 2
<211> LENGTH: 397
<212> TYPE: PRT
<213> ORGANISM: Calf

<400> SEQUENCE: 2

```
Met Trp Trp Leu Leu Val Thr Val Cys Phe Ile His Met Ser Gly Asn
1               5                   10                  15

Ala Phe Cys Phe Leu Gly Lys Ile Ala Lys Asn Pro Glu Ala Ser Met
                20                  25                  30

Asn Val Ser Gln Met Ile Ser Tyr Trp Gly Tyr Pro Ser Glu Met His
            35                  40                  45

Lys Val Ile Thr Ala Asp Gly Tyr Ile Leu Gln Val Tyr Arg Ile Pro
        50                  55                  60

His Gly Lys Asn Asn Ala Asn His Leu Gly Gln Arg Pro Val Val Phe
65                  70                  75                  80

Leu Gln His Gly Leu Leu Gly Ser Ala Thr Asn Trp Ile Ser Asn Leu
                85                  90                  95

Pro Lys Asn Ser Leu Gly Phe Leu Leu Ala Asp Ala Gly Tyr Asp Val
                100                 105                 110

Trp Leu Gly Asn Ser Arg Gly Asn Thr Trp Ala Gln Glu His Leu Tyr
            115                 120                 125

Tyr Ser Pro Asp Ser Pro Glu Phe Trp Ala Phe Ser Phe Asp Glu Met
        130                 135                 140

Ala Glu Tyr Asp Leu Pro Ser Thr Ile Asp Phe Ile Leu Arg Arg Thr
```

```
                145                 150                 155                 160
        Gly Gln Lys Lys Leu His Tyr Val Gly His Ser Gln Gly Thr Thr Ile
                        165                 170                 175

Gly Phe Ile Ala Phe Ser Thr Ser Pro Thr Leu Ala Glu Lys Ile Lys
                        180                 185                 190

Val Phe Tyr Ala Leu Ala Pro Val Ala Thr Val Lys Tyr Thr Lys Ser
                        195                 200                 205

Leu Phe Asn Lys Leu Ala Leu Ile Pro His Phe Leu Phe Lys Ile Ile
                        210                 215                 220

Phe Gly Asp Lys Met Phe Tyr Pro His Thr Phe Leu Glu Gln Phe Leu
        225                 230                 235                 240

Gly Val Glu Met Cys Ser Arg Glu Thr Leu Asp Val Leu Cys Lys Asn
                            245                 250                 255

Ala Leu Phe Ala Ile Thr Gly Val Asp Asn Lys Asn Phe Asn Met Ser
                            260                 265                 270

Arg Leu Asp Val Tyr Ile Ala His Asn Pro Ala Gly Thr Ser Val Gln
                            275                 280                 285

Asn Thr Leu His Trp Arg Gln Ala Val Lys Ser Gly Lys Phe Gln Ala
                            290                 295                 300

Phe Asp Trp Gly Ala Pro Tyr Gln Asn Leu Met His Tyr His Gln Pro
        305                 310                 315                 320

Thr Pro Pro Ile Tyr Asn Leu Thr Ala Met Asn Val Pro Ile Ala Val
                            325                 330                 335

Trp Ser Ala Asp Asn Asp Leu Leu Ala Asp Pro Gln Asp Val Asp Phe
                            340                 345                 350

Leu Leu Ser Lys Leu Ser Asn Leu Ile Tyr His Lys Glu Ile Pro Asn
                            355                 360                 365

Tyr Asn His Leu Asp Phe Ile Trp Ala Met Asp Ala Pro Gln Glu Val
                            370                 375                 380

Tyr Asn Glu Ile Val Ser Leu Met Ala Glu Asp Lys Lys
        385                 390                 395

<210> SEQ ID NO 3
<211> LENGTH: 1137
<212> TYPE: DNA
<213> ORGANISM: Artificial Sequence
<220> FEATURE:
<223> OTHER INFORMATION: PGE protein feature optimized (PFO) variant
      KL8, 1 extra glycosylation site added

<400> SEQUENCE: 3
tttttgggta agattgccaa gaacccagaa gcctccatga acgtttctca aatgatctct        60 tactgggggtt acccatctga aatgcacaag gttatcactg ctgacggtta catcttacaa      120
gtctacagaa tcccacacgg taagaacaat gctaaccatt tgggtcaaag accagttgtt      180
ttcttgcaac atggtctatt aggttctgcc accaactgga tctccaactt gccaaacaac      240
tctttgggtt tcttgttggc tgatgctggt tacgatgtct ggttaggtaa ctccagaggt      300
aacacctggg ctcaagaaca cttgtactac tctccagatt ctccagaatt ctgggctttc      360
tctttcgacg aaatggctga atacgacttg ccatctacca ttgacttcat cttgagaaga      420
accggtcaaa agaaattgca ctacgttggt cactctcaag taccaccat ggtttcatt       480 gctttctcca cttctccaac tttggctgaa aagatcaagg ttttctacgc tttggctcca      540
gttgccaccg tcaagtacac caaatcttta ttcaacaat tggctttgat tccacacttc       600
ttattcaaga tcatcttcgg tgacaagatg ttctatcctc acactttctt ggaacaattc      660
```

-continued

```
ttgggtgttg aaatgtgttc cagagaaact ttggatgtct tgtgtaagaa cgctttgttt      720
gccatcactg gtgttgacaa caagaacttc aacatgtccc gtttggatgt ctacattgct      780
cacaacccag ctggtacttc cgttcaaaac actttgcact ggagacaagc tgtcaaatct      840
ggtaagttcc aagcctttga ctggggtgct ccataccaaa acttgatgca ctaccaccaa      900
ccaaccccac caatctacaa cttgactgcc atgaacgttc aattgctgt ctggtccgct       960 gacaacgatt tgttggctga ccctcaagat gtcgacttct tgctatccaa gttgtccaac     1020
ttgatctacc acaaggaaat tccaaactac aaccatttgg atttcatctg ggctatggac     1080
gctccacaag aagtctacaa cgaaattgtc tctttgatgg ctgaagacaa gaagtaa       1137
```

<210> SEQ ID NO 4
<211> LENGTH: 378
<212> TYPE: PRT
<213> ORGANISM: Artificial Sequence
<220> FEATURE:
<223> OTHER INFORMATION: PGE PFO variant KL8, 1 extra glycosylation site added

<400> SEQUENCE: 4

```
Phe Leu Gly Lys Ile Ala Lys Asn Pro Glu Ala Ser Met Asn Val Ser
  1               5                  10                  15

Gln Met Ile Ser Tyr Trp Gly Tyr Pro Ser Glu Met His Lys Val Ile
             20                  25                  30

Thr Ala Asp Gly Tyr Ile Leu Gln Val Tyr Arg Ile Pro His Gly Lys
         35                  40                  45

Asn Asn Ala Asn His Leu Gly Gln Arg Pro Val Val Phe Leu Gln His
     50                  55                  60

Gly Leu Leu Gly Ser Ala Thr Asn Trp Ile Ser Asn Leu Pro Asn Asn
 65                  70                  75                  80

Ser Leu Gly Phe Leu Leu Ala Asp Ala Gly Tyr Asp Val Trp Leu Gly
                 85                  90                  95

Asn Ser Arg Gly Asn Thr Trp Ala Gln Glu His Leu Tyr Tyr Ser Pro
            100                 105                 110

Asp Ser Pro Glu Phe Trp Ala Phe Ser Phe Asp Glu Met Ala Glu Tyr
        115                 120                 125

Asp Leu Pro Ser Thr Ile Asp Phe Ile Leu Arg Arg Thr Gly Gln Lys
    130                 135                 140

Lys Leu His Tyr Val Gly His Ser Gln Gly Thr Thr Ile Gly Phe Ile
145                 150                 155                 160

Ala Phe Ser Thr Ser Pro Thr Leu Ala Glu Lys Ile Lys Val Phe Tyr
                165                 170                 175

Ala Leu Ala Pro Val Ala Thr Val Lys Tyr Thr Lys Ser Leu Phe Asn
            180                 185                 190

Lys Leu Ala Leu Ile Pro His Phe Leu Phe Lys Ile Ile Phe Gly Asp
        195                 200                 205

Lys Met Phe Tyr Pro His Thr Phe Leu Glu Gln Phe Leu Gly Val Glu
    210                 215                 220

Met Cys Ser Arg Glu Thr Leu Asp Val Leu Cys Lys Asn Ala Leu Phe
225                 230                 235                 240

Ala Ile Thr Gly Val Asp Asn Lys Asn Phe Asn Met Ser Arg Leu Asp
                245                 250                 255

Val Tyr Ile Ala His Asn Pro Ala Gly Thr Ser Val Gln Asn Thr Leu
            260                 265                 270
```

```
    His Trp Arg Gln Ala Val Lys Ser Gly Lys Phe Gln Ala Phe Asp Trp
            275                 280                 285

Gly Ala Pro Tyr Gln Asn Leu Met His Tyr His Gln Pro Thr Pro Pro
        290                 295                 300

Ile Tyr Asn Leu Thr Ala Met Asn Val Pro Ile Ala Val Trp Ser Ala
    305                 310                 315                 320

Asp Asn Asp Leu Leu Ala Asp Pro Gln Asp Val Asp Phe Leu Leu Ser
                    325                 330                 335

Lys Leu Ser Asn Leu Ile Tyr His Lys Glu Ile Pro Asn Tyr Asn His
                340                 345                 350

Leu Asp Phe Ile Trp Ala Met Asp Ala Pro Gln Glu Val Tyr Asn Glu
                355                 360                 365

Ile Val Ser Leu Met Ala Glu Asp Lys Lys
            370                 375

<210> SEQ ID NO 5
<211> LENGTH: 1137
<212> TYPE: DNA
<213> ORGANISM: Artificial Sequence
<220> FEATURE:
<223> OTHER INFORMATION: PGE PFO variant KL9, 5 extra glycosylation
      sites added

<400> SEQUENCE: 5
tttttgggta agattgccaa gaacccagaa gcctccatga acgtttctca atgatctct       60 tactggggtt acccatctga aatgcacaag gtcatcactg ctgatggtta catcttacaa     120
gtctacagaa ttccacacgg taagaacaac tccaaccatt tgggtcaaag accagttgtc    180
tttttgcaac acggtctatt aggttctgct accaactgga tctccaactt gccaaacaac    240
tctttgggtt tcttgttggc tgatgccggt tacgatgtct ggttaggtaa ctccccgtggt   300 aacacctggg ctcaagaaca cttgtactac tctccagact tccagaatt ctgggctttc    360 tctttcgacg aaatggctga atacgacttg ccatctacca ttgacttcat cttgaacaag    420
accggtcaaa agaagttgca ctacgttggt cactctcaag gtaccaccat tggtttcatc    480
gctttctcca cttctccaac tttggctgaa aagatcaagg ttttctacgc tttggctcca    540
gttgctaccg tcaagtacac caaatcttta ttcaacaaat tggctttgat tccacacttc    600
ttattcaaga tcatcttcgg tgacaagatg ttctacccac acacttcttt ggaacaattc    660
ttgggtgttg aaatgtgttc cagagaaact ttggatgtct tgtgtaagaa cgcttttgttt  720 gccatcactg tgtgttgacaa caagaacttc aacatgtcca gattagatgt ctacattgct   780
cacaacccag ccggtacttc tgttcaaaac actttgcact ggagacaagc tgtcaagtct    840
ggtaagttcc aagccttcga ctggggtgct ccataccaaa acttgatgca ctacaaccaa   900
tccactccac ctatctacaa cttgactgcc atgaacgttc caattgctgt ctggtctgct    960
gacaacgatt tgttggctga ccctcaagat gtcgatttct tgctatccaa gttgtccaac   1020
ttgacctacc acaaggaaat tccaaactac aaccatttgg acttcatctg gctatggac   1080 gctccacaag aagtttacaa cgaaatcgtt tctttgatgg ctgaagacaa aaaataa      1137

<210> SEQ ID NO 6
<211> LENGTH: 378
<212> TYPE: PRT
<213> ORGANISM: Artificial Sequence
<220> FEATURE:
<223> OTHER INFORMATION: PGE PFO variant KL9, 5 extra glycosylation
      sites added
```

<400> SEQUENCE: 6

Phe Leu Gly Lys Ile Ala Lys Asn Pro Glu Ala Ser Met Asn Val Ser
1               5                   10                  15

Gln Met Ile Ser Tyr Trp Gly Tyr Pro Ser Glu Met His Lys Val Ile
            20                  25                  30

Thr Ala Asp Gly Tyr Ile Leu Gln Val Tyr Arg Ile Pro His Gly Lys
        35                  40                  45

Asn Asn Ser Asn His Leu Gly Gln Arg Pro Val Val Phe Leu Gln His
    50                  55                  60

Gly Leu Gly Ser Ala Thr Asn Trp Ile Ser Asn Leu Pro Asn Asn
65                  70                  75                  80

Ser Leu Gly Phe Leu Leu Ala Asp Ala Gly Tyr Asp Val Trp Leu Gly
                85                  90                  95

Asn Ser Arg Gly Asn Thr Trp Ala Gln Glu His Leu Tyr Tyr Ser Pro
            100                 105                 110

Asp Ser Pro Glu Phe Trp Ala Phe Ser Phe Asp Glu Met Ala Glu Tyr
        115                 120                 125

Asp Leu Pro Ser Thr Ile Asp Phe Ile Leu Asn Lys Thr Gly Gln Lys
    130                 135                 140

Lys Leu His Tyr Val Gly His Ser Gln Gly Thr Thr Ile Gly Phe Ile
145                 150                 155                 160

Ala Phe Ser Thr Ser Pro Thr Leu Ala Glu Lys Ile Lys Val Phe Tyr
                165                 170                 175

Ala Leu Ala Pro Val Ala Thr Val Lys Tyr Thr Lys Ser Leu Phe Asn
            180                 185                 190

Lys Leu Ala Leu Ile Pro His Phe Leu Phe Lys Ile Ile Phe Gly Asp
        195                 200                 205

Lys Met Phe Tyr Pro His Thr Phe Leu Glu Gln Phe Leu Gly Val Glu
    210                 215                 220

Met Cys Ser Arg Glu Thr Leu Asp Val Leu Cys Lys Asn Ala Leu Phe
225                 230                 235                 240

Ala Ile Thr Gly Val Asp Asn Lys Asn Phe Asn Met Ser Arg Leu Asp
                245                 250                 255

Val Tyr Ile Ala His Asn Pro Ala Gly Thr Ser Val Gln Asn Thr Leu
            260                 265                 270

His Trp Arg Gln Ala Val Lys Ser Gly Lys Phe Gln Ala Phe Asp Trp
        275                 280                 285

Gly Ala Pro Tyr Gln Asn Leu Met His Tyr Asn Gln Ser Thr Pro Pro
    290                 295                 300

Ile Tyr Asn Leu Thr Ala Met Asn Val Pro Ile Ala Val Trp Ser Ala
305                 310                 315                 320

Asp Asn Asp Leu Leu Ala Asp Pro Gln Asp Val Asp Phe Leu Leu Ser
                325                 330                 335

Lys Leu Ser Asn Leu Thr Tyr His Lys Glu Ile Pro Asn Tyr Asn His
            340                 345                 350

Leu Asp Phe Ile Trp Ala Met Asp Ala Pro Gln Glu Val Tyr Asn Glu
        355                 360                 365

Ile Val Ser Leu Met Ala Glu Asp Lys Lys
    370                 375

<210> SEQ ID NO 7
<211> LENGTH: 1137
<212> TYPE: DNA
<213> ORGANISM: Artificial Sequence

```
<220> FEATURE:
<223> OTHER INFORMATION: PGE PFO variant KL11, pI shift of 6.96 to 7.74

<400> SEQUENCE: 7
tttttgggta agattgccaa gaacccagaa gcctccatga acgtctctca aatgatctct      60
tactggggtt acccatctga agaacacaag gttaccactg aagacggtta catcttggaa     120
gtcaacagaa ttccacacgg taagaagaac tctgaaaaca ccggtcaaag acctgttgtt     180
ttcttgcaac acggtctatt gggttctgct accaactgga tctccaactt gccaaagaac     240
tctttaggtt tcttgttggc tgacgctggt tacgatgtct ggttaggtaa ctcccgtggt     300
aacacctggg ctagaaagca tttgtactac tctccagatt ccaaggaatt ctgggctttc     360
tctttcgatg aaatggccaa gtacgacttg ccatctacca ttgacttcat cttgagaaga     420
accggtcaaa agaaattgca ctacgttggt cactctcaag gtaccaccat cggtttcatt     480
gctttctcca cttctccaga attggctgaa aagatcaaga ctttctacgc tttggctcca     540
gttgctaccg ttaagtacac caaatcttta ttcaacaaat ggctttgat tccacacttc      600 ttgttcaaga tcattttcgg tgacaagatg ttctacccac acactttctt ggaacaattt     660
ttgggtgtcg aaatgtgttc cagagaaact ttggatgtct tatgtaagaa cgctttgttt     720
gccatcactg gtgttgacaa caagaacttc aacatgtcca gattagatgt ttacattgct     780
cacaacccag ccggtacttc cgttcaaaac actttgcact ggagacaagc tgtcaaatct     840
ggtaagttcc aagcctacga ctgggggttct ccagaccaaa acagaatgca ctaccatcaa     900
tccactccac caatctacaa cttgactgct atgaacgttc caactgctgt ctggtctgct     960
gacaacgatt tgttggctga ccctcaagat gtcaagaact tgctatccaa gttgtccaac    1020
ttgatctacc acaaggaaat tccaaactac aaccatttgg acttcatctg gggtgaagat    1080
gctccacaag aagtttacaa cgaaatcgtc tctttgatga aggaagacaa gaaataa       1137

<210> SEQ ID NO 8
<211> LENGTH: 378
<212> TYPE: PRT
<213> ORGANISM: Artificial Sequence
<220> FEATURE:
<223> OTHER INFORMATION: PGE PFO variant KL11, pI shift of 6.96 to 7.74

<400> SEQUENCE: 8

Phe Leu Gly Lys Ile Ala Lys Asn Pro Glu Ala Ser Met Asn Val Ser
  1               5                  10                  15

Gln Met Ile Ser Tyr Trp Gly Tyr Pro Ser Glu Glu His Lys Val Thr
             20                  25                  30

Thr Glu Asp Gly Tyr Ile Leu Glu Val Asn Arg Ile Pro His Gly Lys
         35                  40                  45

Lys Asn Ser Glu Asn Thr Gly Gln Arg Pro Val Val Phe Leu Gln His
     50                  55                  60

Gly Leu Leu Gly Ser Ala Thr Asn Trp Ile Ser Asn Leu Pro Lys Asn
 65                  70                  75                  80

Ser Leu Gly Phe Leu Leu Ala Asp Ala Gly Tyr Asp Val Trp Leu Gly
                 85                  90                  95

Asn Ser Arg Gly Asn Thr Trp Ala Arg Lys His Leu Tyr Tyr Ser Pro
            100                 105                 110

Asp Ser Lys Glu Phe Trp Ala Phe Ser Phe Asp Glu Met Ala Lys Tyr
        115                 120                 125

Asp Leu Pro Ser Thr Ile Asp Phe Ile Leu Arg Arg Thr Gly Gln Lys
    130                 135                 140
```

Lys Leu His Tyr Val Gly His Ser Gln Gly Thr Thr Ile Gly Phe Ile
145                 150                 155                 160

Ala Phe Ser Thr Ser Pro Glu Leu Ala Glu Lys Ile Lys Thr Phe Tyr
            165                 170                 175

Ala Leu Ala Pro Val Ala Thr Val Lys Tyr Thr Lys Ser Leu Phe Asn
        180                 185                 190

Lys Leu Ala Leu Ile Pro His Phe Leu Phe Lys Ile Ile Phe Gly Asp
    195                 200                 205

Lys Met Phe Tyr Pro His Thr Phe Leu Glu Gln Phe Leu Gly Val Glu
210                 215                 220

Met Cys Ser Arg Glu Thr Leu Asp Val Leu Cys Lys Asn Ala Leu Phe
225                 230                 235                 240

Ala Ile Thr Gly Val Asp Asn Lys Asn Phe Asn Met Ser Arg Leu Asp
            245                 250                 255

Val Tyr Ile Ala His Asn Pro Ala Gly Thr Ser Val Gln Asn Thr Leu
        260                 265                 270

His Trp Arg Gln Ala Val Lys Ser Gly Lys Phe Gln Ala Tyr Asp Trp
    275                 280                 285

Gly Ser Pro Asp Gln Asn Arg Met His Tyr His Gln Ser Thr Pro Pro
290                 295                 300

Ile Tyr Asn Leu Thr Ala Met Asn Val Pro Thr Ala Val Trp Ser Ala
305                 310                 315                 320

Asp Asn Asp Leu Leu Ala Asp Pro Gln Asp Val Lys Asn Leu Leu Ser
            325                 330                 335

Lys Leu Ser Asn Leu Ile Tyr His Lys Glu Ile Pro Asn Tyr Asn His
        340                 345                 350

Leu Asp Phe Ile Trp Gly Glu Asp Ala Pro Gln Glu Val Tyr Asn Glu
    355                 360                 365

Ile Val Ser Leu Met Lys Glu Asp Lys Lys
370                 375

<210> SEQ ID NO 9
<211> LENGTH: 1137
<212> TYPE: DNA
<213> ORGANISM: Artificial Sequence
<220> FEATURE:
<223> OTHER INFORMATION: PGE PFO variant KL12, pI shift from 6.96 to 6.7

<400> SEQUENCE: 9
tttttgggta agattgccaa gaacccagaa gcctccatga acgtttctga atcatctct      60 tactggggtt acccatctga agaacacgaa gttaccactg aagatggtta cattttggaa     120
gttaaccgta ttccacacgg taagaagaac tctgaacaca ccggtaagag acctgttgtt     180
ttcttacaac acggtctatt aggttctgct accaactgga tctctaactt gccaaagaac     240
tctttgggtt tcttgttggc tgatgctggt tacgatgtct ggttaggtaa ctccagaggt     300
aacacctggt ccagaaagca aagactttta tctccagact ccaaggaatt ctgggctttc     360
tctttcgacg aaatggccaa gtacgatttg ccatctacca ttgacttcat cttaaagaag     420
actggtcaaa agaaattgca ctacgtcggt cactctcaag taccaccat  ggtttcatc     480 gctttctcca cctctccaga attggccaag aagatcaaga ctttctacgc tttggctcca     540
gttgctaccg tcaaatacac caaatcttta ttcaacaaat ggctcatttt gccagaattt     600
ttgttcaagg acttgttcgg tgacaaggaa ttctacccac acacttcctt ggaacaattc     660
ttgggtgttg aaatgtgttc cagagaaact ttggatgtct gtgtaagaa cgctttgttt     720

```
gccatcactg gtgtcgacaa caagaacttc aacatgtcca gattggatgt ttacattgct    780
cacaacccag ctggtacttc cgtccaaaac actttgcact ggagacaagc tgtcaaatct    840
ggtaagttcc aagccttcga ctggggttct ccagaccaaa acatgaagca ctaccatcaa    900
tccactccac cagaatacaa cgttaccgac atgaaggttc caactgctgt ctggtctgct    960
gacaacgatt tgttggctga ccctcaagat gttgacttct tgttgtccaa attgtccaac   1020
ttgatctacc acaaggaaat cccacactac aaccatttgg acttcatctg gggtgaagat   1080
gctccacaag aagtctacaa cgaaattatc agattgatga aggaagacaa gaagtaa      1137
```

<210> SEQ ID NO 10
<211> LENGTH: 378
<212> TYPE: PRT
<213> ORGANISM: Artificial Sequence
<220> FEATURE:
<223> OTHER INFORMATION: PGE PFO variant KL12, pI shift from 6.96 to 6.7

<400> SEQUENCE: 10

```
Phe Leu Gly Lys Ile Ala Lys Asn Pro Glu Ala Ser Met Asn Val Ser
1               5                   10                  15

Glu Ile Ile Ser Tyr Trp Gly Tyr Pro Ser Glu Glu His Glu Val Thr
            20                  25                  30

Thr Glu Asp Gly Tyr Ile Leu Glu Val Asn Arg Ile Pro His Gly Lys
        35                  40                  45

Lys Asn Ser Glu His Thr Gly Lys Arg Pro Val Val Phe Leu Gln His
    50                  55                  60

Gly Leu Leu Gly Ser Ala Thr Asn Trp Ile Ser Asn Leu Pro Lys Asn
65                  70                  75                  80

Ser Leu Gly Phe Leu Leu Ala Asp Ala Gly Tyr Asp Val Trp Leu Gly
                85                  90                  95

Asn Ser Arg Gly Asn Thr Trp Ser Arg Lys His Lys Thr Leu Ser Pro
            100                 105                 110

Asp Ser Lys Glu Phe Trp Ala Phe Ser Phe Asp Glu Met Ala Lys Tyr
        115                 120                 125

Asp Leu Pro Ser Thr Ile Asp Phe Ile Leu Lys Lys Thr Gly Gln Lys
    130                 135                 140

Lys Leu His Tyr Val Gly His Ser Gln Gly Thr Thr Ile Gly Phe Ile
145                 150                 155                 160

Ala Phe Ser Thr Ser Pro Glu Leu Ala Lys Lys Ile Lys Thr Phe Tyr
                165                 170                 175

Ala Leu Ala Pro Val Ala Thr Val Lys Tyr Thr Lys Ser Leu Phe Asn
            180                 185                 190

Lys Leu Ala His Leu Pro Glu Phe Leu Phe Lys Asp Leu Phe Gly Asp
        195                 200                 205

Lys Glu Phe Tyr Pro His Thr Phe Leu Glu Gln Phe Leu Gly Val Glu
    210                 215                 220

Met Cys Ser Arg Glu Thr Leu Asp Val Leu Cys Lys Asn Ala Leu Phe
225                 230                 235                 240

Ala Ile Thr Gly Val Asp Asn Lys Asn Phe Asn Met Ser Arg Leu Asp
                245                 250                 255

Val Tyr Ile Ala His Asn Pro Ala Gly Thr Ser Val Gln Asn Thr Leu
            260                 265                 270

His Trp Arg Gln Ala Val Lys Ser Gly Lys Phe Gln Ala Phe Asp Trp
        275                 280                 285
```

-continued

```
Gly Ser Pro Asp Gln Asn Met Lys His Tyr His Gln Ser Thr Pro Pro
            290                 295                 300

Glu Tyr Asn Val Thr Asp Met Lys Val Pro Thr Ala Val Trp Ser Ala
305                 310                 315                 320

Asp Asn Asp Leu Leu Ala Asp Pro Gln Asp Val Asp Phe Leu Leu Ser
                325                 330                 335

Lys Leu Ser Asn Leu Ile Tyr His Lys Glu Ile Pro His Tyr Asn His
            340                 345                 350

Leu Asp Phe Ile Trp Gly Glu Asp Ala Pro Gln Glu Val Tyr Asn Glu
        355                 360                 365

Ile Ile Arg Leu Met Lys Glu Asp Lys Lys
    370                 375
```

<210> SEQ ID NO 11
<211> LENGTH: 1191
<212> TYPE: DNA
<213> ORGANISM: Artificial Sequence
<220> FEATURE:
<223> OTHER INFORMATION: PGE variant with native signal sequence fused to -MAT factor signal pre(pro-)sequence

<400> SEQUENCE: 11

```
atgtggtggt tattggttac cgtttgtttc attcacatgt ccggtaacgc tttctgtttc      60
ttgggtaaga tcgccaagaa cccagaagcc tccatgaacg tttcccaaat gatctcttac    120
tggggttacc catctgaaat gcacaaggtc atcactgctg acggttacat cttacaagtc    180
tacagaatcc cacacggtaa gaacaatgcc aaccatttgg gtcaaagacc agttgttttc    240
ttgcaacacg gtctattagg ttctgctacc aactggatct ccaacttgcc aaagaactct    300
ttgggtttct tgttggctga tgctggttac gatgtctggt tgggtaactc agaggtaac    360
acctgggctc aagaacactt gtactactct ccagattctc agaattctg ggctttctcc    420
ttcgacgaaa tggctgaata cgacttgcca tctaccattg acttcatctt gagaagaacc    480
ggtcaaaaga aattgcacta cgttggtcac tctcaaggta ccaccattgg tttcattgct    540
ttctccactt ctccaacttt ggctgaaaag atcaaggttt ctacgctttt ggctccagtt    600
gccaccgtca agtacaccaa gtctttattc aacaaattgg ctttgattcc acacttcttg    660
ttcaagatca tctttggtga caagatgttc tacccacaca ctttcttgga caattcttg    720
ggtgttgaaa tgtgttctcg tgaaactttg gatgttctat gtaagaacgc tttgtttgcc    780
atcactggtg ttgacaacaa gaacttcaac atgtccagat ggacgtcta cattgctcac    840
aacccagccg gtacttctgt tcaaaacact tgcactggga acaagctgt caaatctggt    900
aagttccaag cctttgactg gggtgctcca taccaaaaact tgatgcacta ccatcaacca    960
actccaccaa tttacaactt gactgccatg aacgttccaa ttgctgtctg gtctgctgac   1020
aacgacttat tagctgatcc tcaagatgtc gatttcttgt tgtccaagtt gtccaacttg   1080
atctaccaca aggaaatccc aaactacaac catttggatt tcatctggc tatggacgct   1140
cctcaagaag tctacaacga aattgtctct ttgatggctg aagacaagaa a           1191
```

<210> SEQ ID NO 12
<211> LENGTH: 2710
<212> TYPE: DNA
<213> ORGANISM: Artificial Sequence
<220> FEATURE:
<223> OTHER INFORMATION: PGE AN3, CPO gene tAG fusion with Kex site (KR)

<400> SEQUENCE: 12

```
atgtcgttcc gatctctact cgccctgagc ggcctcgtct gcacagggtt ggcaaatgtg    60
atttccaagc gcgcgacctt ggattcatgg ttgagcaacg aagcgaccgt ggctcgtact   120
gccatcctga ataacatcgg ggcggacggt gcttgggtgt cgggcgcgga ctctggcatt   180
gtcgttgcta gtcccagcac ggataacccg gactacttct acacctggac tcgcgactct   240
ggtctcgtcc tcaagaccct cgtcgatctc ttccgaaatg gagataccag tctcctctcc   300
accattgaga actacatctc cgcccaggca attgtccagg gtatcagtaa cccctctggt   360
gatctgtcca gcggcgctgg tctcggtgaa cccaagttca atgtcgatga gactgcctac   420
actggttctt ggggacggcc gcagcgagat ggtccggctc tgagagcaac tgctatgatc   480
ggcttcgggc agtggctgct tgacaatggc tacaccagca ccgcaacgga cattgtttgg   540
cccctcgtta ggaacgacct gtcgtatgtg gctcaatact ggaaccagac aggatatgat   600
ctctgggaag aagtcaatgg ctcgtctttc tttacgattg ctgtgcaaca ccgcgccctt   660
gtcgaaggta gtgccttcgc gacggccgtc ggctcgtcct gctcctggtg tgattctcag   720
gcacccgaaa ttctctgcta cctgcagtcc ttctggaccg gcagcttcat tctgccaaac   780
ttcgatagca gccgttccgg caaggacgca aacaccctcc tgggaagcat ccacaccttt   840
gatcctgagg ccgcatgcga cgactccacc ttccagcccct gctccccgcg cgcgctcgcc   900
aaccacaagg aggttgtaga ctcttttccgc tcaatctata ccctcaacga tggtctcagt   960
gacagcgagg ctgttgcggt gggtcggtac cctgaggaca cgtactacaa cggcaacccg  1020
tggttcctgt gcaccttggc tgccgcagag cagttgtacg atgctctata ccagtgggac  1080
aagcaggggt cgttggaggt cacagatgtg tcgctgact tcttcaaggc actgtacagc  1140
gatgctgcta ctggcaccta ctcttcgtcc agttcgactt atagtagcat tgtagatgcc  1200
gtgaagactt tcgccgatgg cttcgtctct attgtggaaa ctcacgccgc aagcaacggc  1260
tccatgtccg agcaatacga caagtctgat ggcgagcagc tttccgctcg cgacctgacc  1320
tggtcttatg ctgctctgct gaccgccaac aaccgtcgta actccgtcgt gcctgcttct  1380
tggggcgaga cctctgccag cagcgtgccc ggcacctgtg cggccacatc tgccattggt  1440
acctacagca gtgtgactgt cacctcgtgg ccgagtatcg tggctactgg cggcaccact  1500
acgacggcta cccccactgg atccggcagc gtgacctcga ccagcaagac caccgcgact  1560
gctagcaagc gcttcctggg caagattgcc aagaaccccg aggccagcat gaacgtttcc  1620
cagatgatct cttactgggg ttaccccctcc gaggagcaca aggtcaccac cgaggatggc  1680
tacatcctgg aggtcaaccg tatccccac ggcaagaaga actccgagaa caccggccag  1740
cgtcccgttg tctttctaca acacggtctg cttggctctg ccaccaactg gatctccaac  1800
ctccccaaga actctcttgg tttcctcctt gccgatgctg gttacgatgt ctggctaggc  1860
aactcccgtg gtaacacctg ggctcaggag cacctctact actctcctga ctccgacgag  1920
ttctgggctt tctccttcga cgagatggcc gagtacgacc tccccagcac catcgacttc  1980
atcctccgcc gcactggcca ggagcagctg cactacgtcg gtcactccca gggtactacc  2040
atcggtttca ttgctttctc cacctccccc gagcttgctg agaagatcaa gaccttctac  2100
gctcttgctc ctgttgccac tgtcaagtac accaagtccc tcttcaacaa gctggctctg  2160
atccccgagt tcctcttcaa ggacctcttc ggtgacaaga tgttctaccc ccacaccttc  2220
ctggagcagt tcctgggtgt tgagatgtgc tctcgcgaaa ccctcgatgt cctttgcaag  2280
aacgccctct tcgccatcac cggtgttgac aacaagaact tcaacatgag ccgtctggat  2340
gtctacattg cccacaaccc tgctggtact tccgtccaga acaccctcca ctggcgccag  2400
```

```
gctgtcaagt ccggcaagtt ccaggcctac gactggggtt cccccgacca gaaccaggag    2460
cactacgacc agagcactcc tcccatctac aacctgaccg acatgaacgt ccccactgct    2520
gtctggtccg ccgacaacga cctccttgcc gacccccagg atgttgagaa cctcctcagc    2580
aagctcagca acctgatcta ccacaaggag atccccaact acaaccacct cgacttcatc    2640
tggggtgagg atgctcctca ggaagtctac aacgaaatag tatctctgat ggaagaggac    2700
aagaagtaaa                                                          2710

<210> SEQ ID NO 13
<211> LENGTH: 2710
<212> TYPE: DNA
<213> ORGANISM: Artificial Sequence
<220> FEATURE:
<223> OTHER INFORMATION: PGE variant AN12, pI shift from 6.96 to 4.6

<400> SEQUENCE: 13
atgtcgttcc gatctctact cgccctgagc ggcctcgtct gcacagggtt ggcaaatgtg      60
atttccaagc gcgcgacctt ggattcatgg ttgagcaacg aagcgaccgt ggctcgtact     120
gccatcctga ataacatcgg ggcggacggt gcttgggtgt cggcgcggac ctctggcatt     180
gtcgttgcta gtcccagcac ggataacccg gactacttct acacctggac tcgcgactct     240
ggtctcgtcc tcaagaccct cgtcgatctc ttccgaaatg gagataccag tctcctctcc     300
accattgaga actacatctc cgcccaggca attgtccagg gtatcagtaa ccccctctggt    360 gatctgtcca gcgcgctgg tctcggtgaa cccaagttca atgtcgatga gactgcctac      420
actggttctt ggggacggcc gcagcgagat ggtccggctc tgagagcaac tgctatgatc     480
ggcttcgggc agtggctgct tgacaatggc tacaccagca ccgcaacgga cattgtttgg     540
cccctcgtta ggaacgacct gtcgtatgtg gctcaatact ggaaccagac aggatatgat     600
ctctgggaag aagtcaatgg ctcgtctttc tttacgattg ctgtgcaaca ccgcgccctt     660
gtcgaaggta gtgccttcgc gacggccgtc ggctcgtcct gctcctggtg tgattctcag     720
gcacccgaaa ttctctgcta cctgcagtcc ttctggaccg gcagcttcat tctggccaac     780
ttcgatagca gccgttccgg caaggacgca aacaccctcc tgggaagcat ccacaccttt     840
gatcctgagg ccgcatgcga cgactccacc ttccagccct gctccccgcg cgcgctcgcc     900
aaccacaagg aggttgtaga ctcttttccgc tcaatctata ccctcaacga tggtctcagt     960
gacagcgagg ctgttgcggt gggtcggtac cctgaggaca cgtactacaa cggcaacccg    1020
tggttcctgt gcaccttggc tgccgcagag cagttgtacg atgctctata ccagtgggac    1080
aagcaggggt cgttggaggt cacagatgtg tcgctggact tcttcaaggc actgtacagc    1140
gatgctgcta ctggcaccta ctcttcgtcc agttcgactt atagtagcat tgtagatgcc    1200
gtgaagactt tcgccgatgg cttcgtctct attgtggaaa ctcacgccgc aagcaacggc    1260
tccatgtccg agcaatacga caagtctgat ggcgagcagc tttccgctcg cgacctgacc    1320
tggtcttatg ctgctctgct gaccgccaac aaccgtcgta actccgtcgt gcctgcttct    1380
tggggcgaga cctctgccag cagcgtgccc ggcacctgtg cggccacatc tgccattggt    1440
acctacagca gtgtgactgt cacctcgtgg ccgagtatcg tggctactgg cggcaccact    1500
acgacggcta ccccactgg atccggcagc gtgacctcga ccagcaagac caccgcgact    1560
gctagcaagc gcttcctggg caagattgcc aagaaccccg aggccagcat gaacgtttcc    1620
cagatgatct cctactgggg ttaccccctcc gaggagtacg aggtcaccac tgaggatggc    1680
```

-continued

```
tacatcctgg aggtcaaccg tatcccccac ggcaagaaga actccgagaa cactggccag   1740
cgtcccgttg ttttcctgca gcacggtctg cttggttccg ccaccaactg gatctccaac   1800
ctccccaaca actcgctagg attcctcctt gccgatgccg gttacgatgt ctggctaggc   1860
aactcccgtg gtaacacctg ggctcgccgc aacctctact actctcctga ctccgttgag   1920
ttctgggctt tctccttcga cgagatggct gagtacgacc tccccagcac cattgacttc   1980
atcctggaaa agaccggcca ggagcagctg cactacgtcg gtcactccca gggtactacc   2040
atcggtttca ttgctttctc cacctccccc gagcttgctg agaagatcaa gaccttctac   2100
gctcttgctc ctgttgccac cgtcaagtac accaagtccc tcttcaacaa gcttgctctg   2160
atcccccagt ccctcttcaa ggacctcttc ggtgacaagg agttctaccc ccacaccttc   2220
ctggagcagt tcctggccac tgagatgtgc tctcgcgaaa ccctcgatgt cctctgcaag   2280
aacgccctct tcgccatcac cggtgttgac aacaagaact tcaacatgag ccgtctggat   2340
gtctaccttt ctcacaaccc tgctggcacc tccgtccaga acaccctcca ctggcgccag   2400
gctgtcaagt ccggcaagtt ccaggcctac gactggggtt ctcctgacca gaaccaggag   2460
cactacgacc agagcactcc tcccatctac aacctcaccg acatgaacgt ccccactgct   2520
gtctggtctg ccgacaacga cctccttgcc gacccccagg atgttgagaa cctcctcagc   2580
aagctcagca acctgatcta ccacaaggag atccccaact acaaccacct cgacttcatc   2640
tggggtgagg atgctcctca ggaagtctac aacgaaatag tatctctgat ggaagaagat   2700
aaaaagtaaa                                                          2710
```

<210> SEQ ID NO 14
<211> LENGTH: 902
<212> TYPE: PRT
<213> ORGANISM: Artificial Sequence
<220> FEATURE:
<223> OTHER INFORMATION: PGE variant AN12, pI shift from 6.96 to 4.6

<400> SEQUENCE: 14

```
Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175
```

```
Asp Ile Val Trp Pro Leu Val Arg Asn Asp Leu Ser Tyr Val Ala Gln
                180                 185                 190

Tyr Trp Asn Gln Thr Gly Tyr Asp Leu Trp Glu Val Asn Gly Ser
        195                 200                 205

Ser Phe Phe Thr Ile Ala Val Gln His Arg Ala Leu Val Glu Gly Ser
210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
                260                 265                 270

Leu Leu Gly Ser Ile His Thr Phe Asp Pro Glu Ala Ala Cys Asp Asp
                275                 280                 285

Ser Thr Phe Gln Pro Cys Ser Pro Arg Ala Leu Ala Asn His Lys Glu
                290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
                340                 345                 350

Tyr Asp Ala Leu Tyr Gln Trp Asp Lys Gln Gly Ser Leu Glu Val Thr
                355                 360                 365

Asp Val Ser Leu Asp Phe Phe Lys Ala Leu Tyr Ser Asp Ala Ala Thr
                370                 375                 380

Gly Thr Tyr Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
                420                 425                 430

Gln Leu Ser Ala Arg Asp Leu Thr Trp Ser Tyr Ala Ala Leu Leu Thr
                435                 440                 445

Ala Asn Asn Arg Arg Asn Ser Val Val Pro Ala Ser Trp Gly Glu Thr
450                 455                 460

Ser Ala Ser Ser Val Pro Gly Thr Cys Ala Ala Thr Ser Ala Ile Gly
465                 470                 475                 480

Thr Tyr Ser Ser Val Thr Val Ser Trp Pro Ser Ile Val Ala Thr
                485                 490                 495

Gly Gly Thr Thr Thr Thr Ala Thr Pro Thr Gly Ser Gly Ser Val Thr
                500                 505                 510

Ser Thr Ser Lys Thr Thr Ala Thr Ala Ser Lys Arg Phe Leu Gly Lys
                515                 520                 525

Ile Ala Lys Asn Pro Glu Ala Ser Met Asn Val Ser Gln Met Ile Ser
                530                 535                 540

Tyr Trp Gly Tyr Pro Ser Glu Glu Tyr Glu Val Thr Thr Glu Asp Gly
545                 550                 555                 560

Tyr Ile Leu Glu Val Asn Arg Ile Pro His Gly Lys Lys Asn Ser Glu
                565                 570                 575

Asn Thr Gly Gln Arg Pro Val Val Phe Leu Gln His Gly Leu Leu Gly
                580                 585                 590

Ser Ala Thr Asn Trp Ile Ser Asn Leu Pro Asn Asn Ser Leu Gly Phe
```

```
                    595                 600                 605
Leu Leu Ala Asp Ala Gly Tyr Asp Val Trp Leu Gly Asn Ser Arg Gly
610                 615                 620

Asn Thr Trp Ala Arg Arg Asn Leu Tyr Tyr Ser Pro Asp Ser Val Glu
625                 630                 635                 640

Phe Trp Ala Phe Ser Phe Asp Glu Met Ala Glu Tyr Asp Leu Pro Ser
                645                 650                 655

Thr Ile Asp Phe Ile Leu Glu Lys Thr Gly Gln Glu Gln Leu His Tyr
            660                 665                 670

Val Gly His Ser Gln Gly Thr Thr Ile Gly Phe Ile Ala Phe Ser Thr
        675                 680                 685

Ser Pro Glu Leu Ala Glu Lys Ile Lys Thr Phe Tyr Ala Leu Ala Pro
690                 695                 700

Val Ala Thr Val Lys Tyr Thr Lys Ser Leu Phe Asn Lys Leu Ala Leu
705                 710                 715                 720

Ile Pro Gln Ser Leu Phe Lys Asp Leu Phe Gly Asp Lys Glu Phe Tyr
                725                 730                 735

Pro His Thr Phe Leu Glu Gln Phe Leu Ala Thr Glu Met Cys Ser Arg
            740                 745                 750

Glu Thr Leu Asp Val Leu Cys Lys Asn Ala Leu Phe Ala Ile Thr Gly
        755                 760                 765

Val Asp Asn Lys Asn Phe Asn Met Ser Arg Leu Asp Val Tyr Leu Ser
770                 775                 780

His Asn Pro Ala Gly Thr Ser Val Gln Asn Thr Leu His Trp Arg Gln
785                 790                 795                 800

Ala Val Lys Ser Gly Lys Phe Gln Ala Tyr Asp Trp Gly Ser Pro Asp
                805                 810                 815

Gln Asn Gln Glu His Tyr Asp Gln Ser Thr Pro Pro Ile Tyr Asn Leu
            820                 825                 830

Thr Asp Met Asn Val Pro Thr Ala Val Trp Ser Ala Asp Asn Asp Leu
        835                 840                 845

Leu Ala Asp Pro Gln Asp Val Glu Asn Leu Leu Ser Lys Leu Ser Asn
850                 855                 860

Leu Ile Tyr His Lys Glu Ile Pro Asn Tyr Asn His Leu Asp Phe Ile
865                 870                 875                 880

Trp Gly Glu Asp Ala Pro Gln Glu Val Tyr Asn Glu Ile Val Ser Leu
                885                 890                 895

Met Glu Glu Asp Lys Lys
            900

<210> SEQ ID NO 15
<211> LENGTH: 2710
<212> TYPE: DNA
<213> ORGANISM: Artificial Sequence
<220> FEATURE:
<223> OTHER INFORMATION: PGE variant AN13, pI shift from 6.96 to 4.88

<400> SEQUENCE: 15
atgtcgttcc gatctctact cgccctgagc ggcctcgtct gcacagggtt ggcaaatgtg       60
atttccaagc gcgcgacctt ggattcatgg ttgagcaacg aagcgaccgt ggctcgtact      120
gccatcctga ataacatcgg ggcggacggt gcttgggtgt cgggcgcgga ctctggcatt      180
gtcgttgcta gtcccagcac ggataacccg gactacttct acacctggac tcgcgactct      240
ggtctcgtcc tcaagaccct cgtcgatctc ttccgaaatg gagataccag tctcctctcc      300
```

```
accattgaga actacatctc cgcccaggca attgtccagg gtatcagtaa cccctctggt    360
gatctgtcca gcggcgctgg tctcggtgaa cccaagttca atgtcgatga gactgcctac    420
actggttctt ggggacggcc gcagcgagat ggtccggctc tgagagcaac tgctatgatc    480
ggcttcgggc agtggctgct tgacaatggc tacaccagca ccgcaacgga cattgtttgg    540
cccctcgtta ggaacgacct gtcgtatgtg gctcaatact ggaaccagac aggatatgat    600
ctctgggaag aagtcaatgg ctcgtctttc tttacgattg ctgtgcaaca ccgcgccctt    660
gtcgaaggta gtgccttcgc gacggccgtc ggctcgtcct gctcctggtg tgattctcag    720
gcacccgaaa ttctctgcta cctgcagtcc ttctggaccg gcagcttcat tctggccaac    780
ttcgatagca gccgttccgg caaggacgca acaccctcc tgggaagcat ccacaccttt    840
gatcctgagg ccgcatgcga cgactccacc ttccagccct gctccccgcg cgcgctcgcc    900
aaccacaagg aggttgtaga ctcttccgc tcaatctata ccctcaacga tggtctcagt    960
gacagcgagg ctgttgcggt gggtcggtac cctgaggaca cgtactacaa cggcaacccg   1020
tggttcctgt gcaccttggc tgccgcagag cagttgtacg atgctctata ccagtgggac   1080
aagcaggggt cgttggaggt cacagatgtg tcgctggact tcttcaaggc actgtacagc   1140
gatgctgcta ctggcaccta ctcttcgtcc agttcgactt atagtagcat tgtagatgcc   1200
gtgaagactt tcgccgatgg cttcgtctct attgtggaaa ctcacgccgc aagcaacggc   1260
tccatgtccg agcaatacga caagtctgat ggcgagcagc tttccgctcg cgacctgacc   1320
tggtcttatg ctgctctgct gaccgccaac aaccgtcgta actccgtcgt gcctgcttct   1380
tggggcgaga cctctgccag cagcgtgccc ggcacctgtg cggccacatc tgccattggt   1440
acctacagca gtgtgactgt cacctcgtgg ccgagtatcg tggctactgg cggcaccact   1500
acgacggcta cccccactgg atccggcagc gtgacctcga ccagcaagac caccgcgact   1560
gctagcaagc gcctcttcgg caagctccac cccaaccccg aggccaacat gaacatctcc   1620
cagatcatct cctactgggg ttaccccctcc gaggagtacg aggttgtcac cgaggatggc   1680
tacatcctcg aggtcaaccg tatcccccac ggcaagaaca cgccaacaa cactggccag   1740 cgtcccgttg ttttcctgca gcacggtctg cttggctctg ccagcaactg gatctccaac   1800
ctccccaaca actctcttgg tttcctcctt gccgatgctg gttacgatgt ctggctaggc   1860
aactcccgtg gtaacacctg gtcccgcaag cacaagaccc tcagccctga cagcgttgag   1920
ttctgggctt tctccttcga cgagatggcc aagtacgacc tccccgccac cattgacttc   1980
atcctggaaa agaccggcca ggagcagctc tactacgtcg gtcactccca gggtactacc   2040
attggtttca ttgctttctc caccaacccc gagcttgctg agaagatcaa gaccttctac   2100
gcccttgctc ctgttgccac cgtcaagtac accaagtccc tcttcaacaa gctggctctg   2160
atccccgact ccctcttcaa ggtcctcttc ggtgacaagg agttctaccc ccacaccttc   2220
ctggagcagt cctgccacc tgagatgtgc tctcgcgaaa ccctcgacct cctttgctcc   2280
aacgccctct tcgccatcac cggtgttgac aacaagaact tcaacatgag ccgtctggat   2340
gtctacctct cccacaaccc tgctggtact tccgtccaga cacccctcca ctggcgccag   2400
gctgtcaagt ccggcaagtt ccaggctttc gactgggggtt ctcctgacca gaaccaggag   2460
cactacaacc agagcactcc tcctctgtac aacctgaccg acatgaacgt ccccactgct   2520
gtctggtccg gtggtcagga tcttctggcc gaccccagg atgttgacct cctcctcccc   2580
aagatcacca acctgatcta ccacaaggag atccccaact acaaccacct cgacttcatc   2640
tgggccatgg atgctcctca ggaagtctac aacgaaatag tatctctgat ggaagaggac   2700
```
aagaagtaaa                                                                      2710

<210> SEQ ID NO 16
<211> LENGTH: 902
<212> TYPE: PRT
<213> ORGANISM: Artificial Sequence
<220> FEATURE:
<223> OTHER INFORMATION: PGE variant AN13, pI shift from 6.96 to 4.88

<400> SEQUENCE: 16

```
Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Glu Gln Leu
            340                 345                 350
```

```
Tyr Asp Ala Leu Tyr Gln Trp Asp Lys Gln Gly Ser Leu Glu Val Thr
            355                 360                 365

Asp Val Ser Leu Asp Phe Phe Lys Ala Leu Tyr Ser Asp Ala Ala Thr
        370                 375                 380

Gly Thr Tyr Ser Ser Ser Ser Thr Tyr Ser Ser Ile Val Asp Ala
385                 390                 395                 400

Val Lys Thr Phe Ala Asp Gly Phe Val Ser Ile Val Glu Thr His Ala
                405                 410                 415

Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Lys Arg Leu Phe Gly Lys
        515                 520                 525

Leu His Pro Asn Pro Glu Ala Asn Met Asn Ile Ser Gln Ile Ile Ser
    530                 535                 540

Tyr Trp Gly Tyr Pro Ser Glu Glu Tyr Glu Val Val Thr Glu Asp Gly
545                 550                 555                 560

Tyr Ile Leu Glu Val Asn Arg Ile Pro His Gly Lys Asn Asn Ala Asn
                565                 570                 575

Asn Thr Gly Gln Arg Pro Val Val Phe Leu Gln His Gly Leu Leu Gly
            580                 585                 590

Ser Ala Ser Asn Trp Ile Ser Asn Leu Pro Asn Asn Ser Leu Gly Phe
        595                 600                 605

Leu Leu Ala Asp Ala Gly Tyr Asp Val Trp Leu Gly Asn Ser Arg Gly
    610                 615                 620

Asn Thr Trp Ser Arg Lys His Lys Thr Leu Ser Pro Asp Ser Val Glu
625                 630                 635                 640

Phe Trp Ala Phe Ser Phe Asp Glu Met Ala Lys Tyr Asp Leu Pro Ala
                645                 650                 655

Thr Ile Asp Phe Ile Leu Glu Lys Thr Gly Gln Glu Gln Leu Tyr Tyr
            660                 665                 670

Val Gly His Ser Gln Gly Thr Thr Ile Gly Phe Ile Ala Phe Ser Thr
        675                 680                 685

Asn Pro Glu Leu Ala Glu Lys Ile Lys Thr Phe Tyr Ala Leu Ala Pro
    690                 695                 700

Val Ala Thr Val Lys Tyr Thr Lys Ser Leu Phe Asn Lys Leu Ala Leu
705                 710                 715                 720

Ile Pro Asp Ser Leu Phe Lys Val Leu Phe Gly Asp Lys Glu Phe Tyr
                725                 730                 735

Pro His Thr Phe Leu Glu Gln Phe Leu Ala Thr Glu Met Cys Ser Arg
            740                 745                 750

Glu Thr Leu Asp Leu Leu Cys Ser Asn Ala Leu Phe Ala Ile Thr Gly
        755                 760                 765

Val Asp Asn Lys Asn Phe Asn Met Ser Arg Leu Asp Val Tyr Leu Ser
```

```
                    770             775             780
His Asn Pro Ala Gly Thr Ser Val Gln Asn Thr Leu His Trp Arg Gln
785                 790             795                 800

Ala Val Lys Ser Gly Lys Phe Gln Ala Phe Asp Trp Gly Ser Pro Asp
                805             810              815

Gln Asn Gln Glu His Tyr Asn Gln Ser Thr Pro Pro Leu Tyr Asn Leu
            820              825              830

Thr Asp Met Asn Val Pro Thr Ala Val Trp Ser Gly Gly Gln Asp Leu
         835              840              845

Leu Ala Asp Pro Gln Asp Val Asp Leu Leu Pro Lys Ile Thr Asn
850              855              860

Leu Ile Tyr His Lys Glu Ile Pro Asn Tyr Asn His Leu Asp Phe Ile
865              870             875                 880

Trp Ala Met Asp Ala Pro Gln Glu Val Tyr Asn Glu Ile Val Ser Leu
                885              890             895

Met Glu Glu Asp Lys Lys
            900
```

<210> SEQ ID NO 17
<211> LENGTH: 1342
<212> TYPE: DNA
<213> ORGANISM: Artificial Sequence
<220> FEATURE:
<223> OTHER INFORMATION: Chitinase (ZDU) wild-type

<400> SEQUENCE: 17

```
atgaagctct ctccatcct cctcgtcgct cttgtatctc tggtcagcgg tgctcaccac      60
caccgtcacc gtcacatgaa cgaccctgct cctgcttctt tccccggtcc ccaccaccag    120
caccacggta tccctcctca aagctggtt gctcgcaaca cttctgctga gtacaagtcc     180
attgcctact cgtcaactg ggccatctac ggccgcaacc acaaccccca ggacatcccc     240
attgacaagc tcacccacat cctgtacgct ttcgccaacg tccgtgccaa cggcgaggtc    300
tacctctccg accctggtc cgacattgac aagcgcttcc ccggtgacag ctggtccgac    360
accggcaaca acgtctacgg ctgtgtcaag cagctcaacc tcctcaagca gaagaaccgc    420
aacctcaagg tcctcctctc catcggtggc tggacctact cttccaactt cgtcaccccc    480
gccagcactg accagggtcg caagaccttc gcctcttctg ctgtcaagct ccttgccgac    540
cttggtttcg acggtctgga cattgactgg gaatacccg ccaacgaggc tcaggccacc    600
gacatggtcc tcctcctccg tgagatccgt gaggagcttg acgagtacgg ccgtgagcac    660
ggcaacggca cccacttcct gctctccatt gccacctccg ccggtccctc caagtacaac    720
accctgcaca tctcctccat gaacctctac ctcgacttct ggaacctgat ggcctacgac    780
tacgctggca gctgggatgc cactgctggc caccaggcca acctgtaccc cctccgtgat    840
gaccccgtca gcactccctt caacaccgac caggccatct ccgcctacct cactgctggt    900
gttcctgctc acaagctgat cctgggtatg ccctctacg gccgtgcttt caccaacacc    960
gacggtcccg gcaagcccct taacggtgtt ggtcagggca gctgggagaa cggtgtctgg   1020
gactacaagg cccttcctcc tgctggtgcc tccgtcagcg agctgcgctc catcggtgcc   1080
agctactcct acgatgctgg caagaaaacc atgatatctt cgacacactcc tgctgttgct   1140
cgccagaagg ccgactacat ccgctccaag ggtcttggtg gtgccatgtg gtgggaaacc   1200
tccggtgaca aggtcggtgt tgagtccctg atctccaccg ttgttgactc tcttggtggt   1260
atcggtgctc ttgacaagtc cgtcaaccac ctggaatacc ccgagtccca gtacgacaac   1320
```
gtcaagaagg gtttccacta aa                                            1342

<210> SEQ ID NO 18
<211> LENGTH: 446
<212> TYPE: PRT
<213> ORGANISM: Artificial Sequence
<220> FEATURE:
<223> OTHER INFORMATION: Chitinase (ZDU) wild-type

<400> SEQUENCE: 18

```
Met Lys Leu Phe Ser Ile Leu Leu Val Ala Leu Val Ser Leu Val Ser
1               5                   10                  15

Gly Ala His His His Arg His Arg His Met Asn Asp Pro Ala Pro Ala
            20                  25                  30

Ser Phe Pro Gly Pro His His Gln His His Gly Ile Pro Pro His Lys
        35                  40                  45

Leu Val Ala Arg Asn Thr Ser Ala Glu Tyr Lys Ser Ile Ala Tyr Phe
    50                  55                  60

Val Asn Trp Ala Ile Tyr Gly Arg Asn His Asn Pro Gln Asp Ile Pro
65                  70                  75                  80

Ile Asp Lys Leu Thr His Ile Leu Tyr Ala Phe Ala Asn Val Arg Ala
                85                  90                  95

Asn Gly Glu Val Tyr Leu Ser Asp Pro Trp Ser Asp Ile Asp Lys Arg
            100                 105                 110

Phe Pro Gly Asp Ser Trp Ser Asp Thr Gly Asn Asn Val Tyr Gly Cys
        115                 120                 125

Val Lys Gln Leu Asn Leu Lys Gln Lys Asn Arg Asn Leu Lys Val
    130                 135                 140

Leu Leu Ser Ile Gly Gly Trp Thr Tyr Ser Ser Asn Phe Val Thr Pro
145                 150                 155                 160

Ala Ser Thr Asp Gln Gly Arg Lys Thr Phe Ala Ser Ser Ala Val Lys
                165                 170                 175

Leu Leu Ala Asp Leu Gly Phe Asp Gly Leu Asp Ile Asp Trp Glu Tyr
            180                 185                 190

Pro Ala Asn Glu Ala Gln Ala Thr Asp Met Val Leu Leu Leu Arg Glu
        195                 200                 205

Ile Arg Glu Glu Leu Asp Glu Tyr Gly Arg Glu His Gly Asn Gly Thr
    210                 215                 220

His Phe Leu Leu Ser Ile Ala Thr Ser Ala Gly Pro Ser Lys Tyr Asn
225                 230                 235                 240

Thr Leu His Ile Ser Ser Met Asn Leu Tyr Leu Asp Phe Trp Asn Leu
                245                 250                 255

Met Ala Tyr Asp Tyr Ala Gly Ser Trp Asp Ala Thr Ala Gly His Gln
            260                 265                 270

Ala Asn Leu Tyr Pro Leu Arg Asp Asp Pro Val Ser Thr Pro Phe Asn
        275                 280                 285

Thr Asp Gln Ala Ile Ser Ala Tyr Leu Thr Ala Gly Val Pro Ala His
    290                 295                 300

Lys Leu Ile Leu Gly Met Pro Leu Tyr Gly Arg Ala Phe Thr Asn Thr
305                 310                 315                 320

Asp Gly Pro Gly Lys Pro Phe Asn Gly Val Gly Gln Gly Ser Trp Glu
                325                 330                 335

Asn Gly Val Trp Asp Tyr Lys Ala Leu Pro Pro Ala Gly Ala Ser Val
            340                 345                 350
```

Ser Glu Leu Arg Ser Ile Gly Ala Ser Tyr Ser Tyr Asp Ala Gly Lys
            355                 360                 365

Lys Thr Met Ile Ser Tyr Asp Thr Pro Ala Val Ala Arg Gln Lys Ala
        370                 375                 380

Asp Tyr Ile Arg Ser Lys Gly Leu Gly Gly Ala Met Trp Trp Glu Thr
385                 390                 395                 400

Ser Gly Asp Lys Val Gly Val Glu Ser Leu Ile Ser Thr Val Val Asp
                405                 410                 415

Ser Leu Gly Gly Ile Gly Ala Leu Asp Lys Ser Val Asn His Leu Glu
            420                 425                 430

Tyr Pro Glu Ser Gln Tyr Asp Asn Val Lys Lys Gly Phe His
        435                 440                 445

<210> SEQ ID NO 19
<211> LENGTH: 1342
<212> TYPE: DNA
<213> ORGANISM: Artificial Sequence
<220> FEATURE:
<223> OTHER INFORMATION: Chitinase variant ZDU-6

<400> SEQUENCE: 19
atgaagctct ctccatcct gctggtcgct cttgtctctt tagtgtctgg cgctcaccac      60
caccgtcacc gtcacatgaa cgaccctgct cctgcctcct tccccggtcc ccaccaccag    120
caccacggta tccctcctca aagcttgtt gctcgcaaca cttctgctga gtaccgctcg     180
gtggcctact cgtcaactg ggccatctac ggccgcaacc acaaccccca ggatcttcct    240
gctgagaagc tcaccacgt cctctacgct ttcgccaacg tccgtccac tggtgaagtc     300
tacctcaccg acacctggtc ggataccgac aagcactacc ccaccgacag ctggtccgac    360
actggtaaca cgtctacgg ctgcgtcaag cagctcttcc tgctcaagca gcagaaccgc    420
aacctcaagg tcctcctctc catcggtggc tggacctact cttccaactt cgctcagccc    480
gcctccactg atgccggtcg caagaccttc gcctccactg ccgtcaagct cctccaggat    540
cttggattcg atggcttgga tattgactgg gaatacccg agaacgacca gcaggcctcc    600
gacttcgtcc tcctcctcaa ggagatccgt gaggagctgg acaactactc tgctgctcac    660
gccaacggcc agcacttctt gttgactgtt gcctccccg ctggtcccca gaactacaac    720
aagctccgtc tgcaggagat gacccctac cttgacttct ggaacctgat ggcctacgac    780
tacgctggca gctgggattc tgttgctggc caccaggcca acctgtaccc cagcacctcc    840
aaccccgcca gcactccttt caacaccgac caggctgttg actactacat ctccgctggt    900
gttcctgcct ccaagattgt cctgggcatg cccttgtacg gccgtgcttt caccaacacc    960
gatggccctg gtaccccctt caacggtgtc ggccagggca gctgggagaa cggtgtgtgg   1020
gattacaagg cccttcctca ggctggtgcc accgaacaca ccgatgactc gattggtgcc   1080
tcctacagct acgaccccag cactcgtacc atgatctcct acgacacccc cgccgttgct   1140
gagatgaagg ctgagtacat ccgctccaag ggtctgggtg gtgccatgtg gtgggagact   1200
tctgccgaca agaccggtga ggattcgctg atcaccaccg tcgtcgaggg tgttggtggt   1260
gttggtgctc ttgaccagtc ccagaaccac ctggaatacc ccgagagcca gtacgacaac   1320
ctgcgcaacg gattccacta aa                                             1342

<210> SEQ ID NO 20
<211> LENGTH: 446
<212> TYPE: PRT
<213> ORGANISM: Artificial Sequence
<220> FEATURE:
<223> OTHER INFORMATION: Chitinase variant ZDU-6

<400> SEQUENCE: 20

```
Met Lys Leu Phe Ser Ile Leu Leu Val Ala Leu Val Ser Leu Val Ser
1               5                   10                  15

Gly Ala His His Arg His Arg His Met Asn Asp Pro Ala Pro Ala
            20                  25                  30

Ser Phe Pro Gly Pro His His Gln His His Gly Ile Pro Pro His Lys
        35                  40                  45

Leu Val Ala Arg Asn Thr Ser Ala Glu Tyr Arg Ser Val Ala Tyr Phe
    50                  55                  60

Val Asn Trp Ala Ile Tyr Gly Arg Asn His Asn Pro Gln Asp Leu Pro
65                  70                  75                  80

Ala Glu Lys Leu Thr His Val Leu Tyr Ala Phe Ala Asn Val Arg Pro
                85                  90                  95

Thr Gly Glu Val Tyr Leu Thr Asp Thr Trp Ser Asp Thr Asp Lys His
            100                 105                 110

Tyr Pro Thr Asp Ser Trp Ser Asp Thr Gly Asn Asn Val Tyr Gly Cys
        115                 120                 125

Val Lys Gln Leu Phe Leu Leu Lys Gln Gln Asn Arg Asn Leu Lys Val
    130                 135                 140

Leu Leu Ser Ile Gly Gly Trp Thr Tyr Ser Ser Asn Phe Ala Gln Pro
145                 150                 155                 160

Ala Ser Thr Asp Ala Gly Arg Lys Thr Phe Ala Ser Thr Ala Val Lys
                165                 170                 175

Leu Leu Gln Asp Leu Gly Phe Asp Gly Leu Asp Ile Asp Trp Glu Tyr
            180                 185                 190

Pro Glu Asn Asp Gln Gln Ala Ser Asp Phe Val Leu Leu Leu Lys Glu
        195                 200                 205

Ile Arg Glu Glu Leu Asp Asn Tyr Ser Ala Ala His Ala Asn Gly Gln
    210                 215                 220

His Phe Leu Leu Thr Val Ala Ser Pro Ala Gly Pro Gln Asn Tyr Asn
225                 230                 235                 240

Lys Leu Arg Leu Gln Glu Met Thr Pro Tyr Leu Asp Phe Trp Asn Leu
                245                 250                 255

Met Ala Tyr Asp Tyr Ala Gly Ser Trp Asp Ser Val Ala Gly His Gln
            260                 265                 270

Ala Asn Leu Tyr Pro Ser Thr Ser Asn Pro Ala Ser Thr Pro Phe Asn
        275                 280                 285

Thr Asp Gln Ala Val Asp Tyr Tyr Ile Ser Ala Gly Val Pro Ala Ser
    290                 295                 300

Lys Ile Val Leu Gly Met Pro Leu Tyr Gly Arg Ala Phe Thr Asn Thr
305                 310                 315                 320

Asp Gly Pro Gly Thr Pro Phe Asn Gly Val Gly Gln Gly Ser Trp Glu
                325                 330                 335

Asn Gly Val Trp Asp Tyr Lys Ala Leu Pro Gln Ala Gly Ala Thr Glu
            340                 345                 350

His Thr Asp Asp Ser Ile Gly Ala Ser Tyr Ser Tyr Asp Pro Ser Thr
        355                 360                 365

Arg Thr Met Ile Ser Tyr Asp Thr Pro Ala Val Ala Glu Met Lys Ala
    370                 375                 380

Glu Tyr Ile Arg Ser Lys Gly Leu Gly Gly Ala Met Trp Trp Glu Thr
385                 390                 395                 400
```

Ser Ala Asp Lys Thr Gly Glu Asp Ser Leu Ile Thr Thr Val Val Glu
            405                 410                 415

Gly Val Gly Gly Val Gly Ala Leu Asp Gln Ser Gln Asn His Leu Glu
        420                 425                 430

Tyr Pro Glu Ser Gln Tyr Asp Asn Leu Arg Asn Gly Phe His
        435                 440                 445

<210> SEQ ID NO 21
<211> LENGTH: 1285
<212> TYPE: DNA
<213> ORGANISM: Artificial Sequence
<220> FEATURE:
<223> OTHER INFORMATION: Chitinase variant ZDU-7

<400> SEQUENCE: 21
atgaagctct tctccatcct gctggtcgct cttgtctctt tagtgtctgg cgctgccatc        60
tggaaccgtg atgctcctag cactgatctg gaggctcgtg ccaacgccgg ttaccgctct       120
gttgccact tcgtcaactg gccatctac ggccgtaacc acaaccccca ggatcttcct         180
gctgagaagc tgacccacgt cctctacgct ttcgccaacg tccgtcccga gactggcgag       240
gtctacttga ctgacacctg gtccgacacc gacaagcact accccaccga cagctggtcc       300
gacactggca caacgtcta cggcaacgtc aagcagctct tcctgctcaa gcagcagaac       360
cgcaacctga aggtcctcct ctccatcggt ggctggacct actctcccaa cttcgctcag       420
cctgccagca ctgatgctgg ccgcaagacc ttcgccagca ctgctgtcaa gctcctccag       480
gatcttggat cgatggtct tgacattgac tgggaatacc ccgccaacga ccagcaggcc       540
tccgacttcg tcctcctcct caaggagatc cgtgaggagc tcgacaacta ctctgctgct       600
cacgctcctg gataccactt cctgctgacc gttgcctccc ccgccggtcc tcagaactac       660
aacaagctcc gcctccagga gatgaccccc taccttgact tctggaactt gatggcctac       720
gactacgctg gcagctggga ttctgttgct ggtcaccagg ccaacctgta ccctccacc       780
tcgaaccccg cctctactcc cttcaacacc gaccaggctg ttgactacta catctccgct       840
ggtgttcctg cctccaagat tgtccttgga atgcctctgt acggccgtgc tttcaccaac       900
accgatggcc ctggtacccc cttcaacggt gtcggccagg gcagctggga gaacggtgtc       960
tgggattaca aggcccttcc ccaggctggt gccactgagc acaccgatga ctccatcggt      1020
gcctcctact cctacgaccc cagcactcgt accatgatct cctacgacac cccgccgtt       1080
gctgagatga aggctgaata catccgctcc aagggcttgg gtggtgccat gtggtgggaa      1140
acctctgccg acaagaccgg tgaggactct ctgatcacca ccgttgttga gggtgttggt      1200
ggtgttggtg ctctggatca gtcccagaac cacctggaat ccccgagtc ccagtacgac      1260
aacctgcgca acggcttcca ctaaa                                             1285

<210> SEQ ID NO 22
<211> LENGTH: 427
<212> TYPE: PRT
<213> ORGANISM: Artificial Sequence
<220> FEATURE:
<223> OTHER INFORMATION: Chitinase variant ZDU-7

<400> SEQUENCE: 22

Met Lys Leu Phe Ser Ile Leu Leu Val Ala Leu Val Ser Leu Val Ser
1               5                   10                  15

Gly Ala Ala Ile Trp Asn Arg Asp Ala Pro Ser Thr Asp Leu Glu Ala
            20                  25                  30

```
Arg Ala Asn Ala Gly Tyr Arg Ser Val Ala Tyr Phe Val Asn Trp Ala
         35                  40                  45

Ile Tyr Gly Arg Asn His Asn Pro Gln Asp Leu Pro Ala Glu Lys Leu
 50                  55                  60

Thr His Val Leu Tyr Ala Phe Ala Asn Val Arg Pro Glu Thr Gly Glu
 65                  70                  75                  80

Val Tyr Leu Thr Asp Thr Trp Ser Asp Thr Lys His Tyr Pro Thr
                 85                  90                  95

Asp Ser Trp Ser Asp Thr Gly Asn Asn Val Tyr Gly Asn Val Lys Gln
                100                 105                 110

Leu Phe Leu Leu Lys Gln Gln Asn Arg Asn Leu Lys Val Leu Leu Ser
                115                 120                 125

Ile Gly Gly Trp Thr Tyr Ser Pro Asn Phe Ala Gln Pro Ala Ser Thr
        130                 135                 140

Asp Ala Gly Arg Lys Thr Phe Ala Ser Thr Ala Val Lys Leu Leu Gln
145                 150                 155                 160

Asp Leu Gly Phe Asp Gly Leu Asp Ile Asp Trp Glu Tyr Pro Ala Asn
                165                 170                 175

Asp Gln Gln Ala Ser Asp Phe Val Leu Leu Leu Lys Glu Ile Arg Glu
                180                 185                 190

Glu Leu Asp Asn Tyr Ser Ala Ala His Ala Pro Gly Tyr His Phe Leu
            195                 200                 205

Leu Thr Val Ala Ser Pro Ala Gly Pro Gln Asn Tyr Asn Lys Leu Arg
        210                 215                 220

Leu Gln Glu Met Thr Pro Tyr Leu Asp Phe Trp Asn Leu Met Ala Tyr
225                 230                 235                 240

Asp Tyr Ala Gly Ser Trp Asp Ser Val Ala Gly His Gln Ala Asn Leu
                245                 250                 255

Tyr Pro Ser Thr Ser Asn Pro Ala Ser Thr Pro Phe Asn Thr Asp Gln
            260                 265                 270

Ala Val Asp Tyr Tyr Ile Ser Ala Gly Val Pro Ala Ser Lys Ile Val
        275                 280                 285

Leu Gly Met Pro Leu Tyr Gly Arg Ala Phe Thr Asn Thr Asp Gly Pro
    290                 295                 300

Gly Thr Pro Phe Asn Gly Val Gly Gln Gly Ser Trp Glu Asn Gly Val
305                 310                 315                 320

Trp Asp Tyr Lys Ala Leu Pro Gln Ala Gly Ala Thr Glu His Thr Asp
                325                 330                 335

Asp Ser Ile Gly Ala Ser Tyr Ser Tyr Asp Pro Ser Thr Arg Thr Met
                340                 345                 350

Ile Ser Tyr Asp Thr Pro Ala Val Ala Glu Met Lys Ala Glu Tyr Ile
            355                 360                 365

Arg Ser Lys Gly Leu Gly Gly Ala Met Trp Trp Glu Thr Ser Ala Asp
370                 375                 380

Lys Thr Gly Glu Asp Ser Leu Ile Thr Thr Val Glu Gly Val Gly
385                 390                 395                 400

Gly Val Gly Ala Leu Asp Gln Ser Gln Asn His Leu Glu Tyr Pro Glu
                405                 410                 415

Ser Gln Tyr Asp Asn Leu Arg Asn Gly Phe His
            420                 425

<210> SEQ ID NO 23
<211> LENGTH: 1525
```

<212> TYPE: DNA
<213> ORGANISM: Artificial Sequence
<220> FEATURE:
<223> OTHER INFORMATION: Beta-glucosidase wild-type ZTB-WT

<400> SEQUENCE: 23

```
atgtccttcc gctctcttct ggctctgtcc ggtctggtct gcaccggtct ggctatgacc      60
accactgaga ctcctaccac caccaccacc tccaccctcc ctcctgactt cctctggggt     120
ttcgccactg cctcctacca gattgagggt gctttcgacg aggatggccg tctgccctcc     180
atctgggata ccttctccaa gacccccggc aaggttgagg atggcaccaa cggtgatgtt     240
gcttgcgaca gctaccaccg cactggtgag gacattgaga tcctcaagaa gtacggtgcc     300
aagatctacc gcttctctct gagctggccc cgtatcattc tcttggtgg tcgcaacgac      360
cccatcaacg agaagggcct ccagttctac tccaagttcc tggatgacct ccacgctgct     420
ggtatcgagc ccttcgtcac cctattccac tgggatcttc ctgacgagct gatgaagcgt     480
tacggtggta tgctcaacaa ggaagaattt gtcgccgact acgccaacta cgcccgtgtt     540
gttttcaacg cccttggcag caaggtcaag cactggatca ccttcaacga gccctggtgc     600
tcctccgtcc ttggtcacaa cactggcaag cacgctcctg gtcgtacctc cgaccgtacc     660
aagtcccccg agggtgatgg cacccgtgag ccctggattg tcggtcacaa cctccttgtt     720
gctcacggta ctgttgttga catctaccgc cgtgagttca aggagaagca gggtggtgag     780
atcggtatca ccctcaacgg tgactgggct gagccctggg accccgagaa ccccgccgat     840
gttgaggctt cgaccgcaa gatcgagttc gccatctcct ggttcgccga ccccatctac     900
cacggcaagt accccgacag catggtcaag cagcttggtg accgtctgcc caagttcacc     960
cccgaggaga ttgctttcgt ccacggcagc aacgacttct acggcatgaa ccactactgc    1020
gagaactaca tccgcaaccg cactggtgag cctgaccccg aggacattgc tggcaacctg    1080
gacatcctga tggaggacaa gaacggcaac cccatcggtc cgagactca gtgcgaatgg    1140
ctacgcccct tccccctagg attccgcaag ctcctcaagt ggctagcgga ccgctacaac    1200
aaccccaaga tctacgtgac cgagaacggc acctccgtca gggtgagtc cgacaagcct    1260
ctggaagaag tcctcaacga cgagttccgt gtccagtact accgtgacta catcggtgcc    1320
atggtcgatg ccgttgctca ggatggtgtc aacgtcaagg cctacatggc ctggtccctc    1380
ctcgacaact tcgaatggtc cgagggctac cgctctcgct tcggtgtcac ctacgtcgac    1440
tacaagaacg gccagaagcg tatccccaag aagtctgctc tggtcattgg tgagctgttc    1500
aacaagtaca tccgcaagga gtaaa                                          1525
```

<210> SEQ ID NO 24
<211> LENGTH: 507
<212> TYPE: PRT
<213> ORGANISM: Artificial Sequence
<220> FEATURE:
<223> OTHER INFORMATION: Beta-glucosidase wild-type ZTB-WT

<400> SEQUENCE: 24

```
Met Ser Phe Arg Ser Leu Leu Ala Leu Ser Gly Leu Val Cys Thr Gly
1               5                   10                  15

Leu Ala Met Thr Thr Thr Glu Thr Pro Thr Thr Thr Thr Thr Ser Thr
            20                  25                  30

Leu Pro Pro Asp Phe Leu Trp Gly Phe Ala Thr Ala Ser Tyr Gln Ile
        35                  40                  45

Glu Gly Ala Phe Asp Glu Asp Gly Arg Leu Pro Ser Ile Trp Asp Thr
```

```
                50                  55                  60
Phe Ser Lys Thr Pro Gly Lys Val Glu Asp Gly Thr Asn Gly Asp Val
65                  70                  75                  80

Ala Cys Asp Ser Tyr His Arg Thr Gly Glu Asp Ile Glu Ile Leu Lys
                85                  90                  95

Lys Tyr Gly Ala Lys Ile Tyr Arg Phe Ser Leu Ser Trp Pro Arg Ile
                100                 105                 110

Ile Pro Leu Gly Gly Arg Asn Asp Pro Ile Asn Glu Lys Gly Leu Gln
                115                 120                 125

Phe Tyr Ser Lys Phe Leu Asp Asp Leu His Ala Ala Gly Ile Glu Pro
                130                 135                 140

Phe Val Thr Leu Phe His Trp Asp Leu Pro Asp Glu Leu Met Lys Arg
145                 150                 155                 160

Tyr Gly Gly Met Leu Asn Lys Glu Glu Phe Val Ala Asp Tyr Ala Asn
                165                 170                 175

Tyr Ala Arg Val Val Phe Asn Ala Leu Gly Ser Lys Val Lys His Trp
                180                 185                 190

Ile Thr Phe Asn Glu Pro Trp Cys Ser Ser Val Leu Gly His Asn Thr
                195                 200                 205

Gly Lys His Ala Pro Gly Arg Thr Ser Asp Arg Thr Lys Ser Pro Glu
                210                 215                 220

Gly Asp Gly Thr Arg Glu Pro Trp Ile Val Gly His Asn Leu Leu Val
225                 230                 235                 240

Ala His Gly Thr Val Val Asp Ile Tyr Arg Arg Glu Phe Lys Glu Lys
                245                 250                 255

Gln Gly Gly Glu Ile Gly Ile Thr Leu Asn Gly Asp Trp Ala Glu Pro
                260                 265                 270

Trp Asp Pro Glu Asn Pro Ala Asp Val Glu Ala Cys Asp Arg Lys Ile
                275                 280                 285

Glu Phe Ala Ile Ser Trp Phe Ala Asp Pro Ile Tyr His Gly Lys Tyr
                290                 295                 300

Pro Asp Ser Met Val Lys Gln Leu Gly Asp Arg Leu Pro Lys Phe Thr
305                 310                 315                 320

Pro Glu Glu Ile Ala Phe Val His Gly Ser Asn Asp Phe Tyr Gly Met
                325                 330                 335

Asn His Tyr Cys Glu Asn Tyr Ile Arg Asn Arg Thr Gly Glu Pro Asp
                340                 345                 350

Pro Glu Asp Ile Ala Gly Asn Leu Asp Ile Leu Met Glu Asp Lys Asn
                355                 360                 365

Gly Asn Pro Ile Gly Pro Glu Thr Gln Cys Glu Trp Leu Arg Pro Phe
                370                 375                 380

Pro Leu Gly Phe Arg Lys Leu Leu Lys Trp Leu Ala Asp Arg Tyr Asn
385                 390                 395                 400

Asn Pro Lys Ile Tyr Val Thr Glu Asn Gly Thr Ser Val Lys Gly Glu
                405                 410                 415

Ser Asp Lys Pro Leu Glu Glu Val Leu Asn Asp Glu Phe Arg Val Gln
                420                 425                 430

Tyr Tyr Arg Asp Tyr Ile Gly Ala Met Val Asp Ala Val Ala Gln Asp
                435                 440                 445

Gly Val Asn Val Lys Ala Tyr Met Ala Trp Ser Leu Leu Asp Asn Phe
                450                 455                 460

Glu Trp Ser Glu Gly Tyr Arg Ser Arg Phe Gly Val Thr Tyr Val Asp
465                 470                 475                 480
```

Tyr Lys Asn Gly Gln Lys Arg Ile Pro Lys Lys Ser Ala Leu Val Ile
            485                 490                 495

Gly Glu Leu Phe Asn Lys Tyr Ile Arg Lys Glu
            500                 505

<210> SEQ ID NO 25
<211> LENGTH: 1501
<212> TYPE: DNA
<213> ORGANISM: Artificial Sequence
<220> FEATURE:
<223> OTHER INFORMATION: Beta-glucosidase variant ZTB-4

<400> SEQUENCE: 25

| | | | | | | |
|---|---|---|---|---|---|---|
| atgtccttcc | gctctcttct | ggctctgtcc | ggtctggtct | gcaccggtct | ggcttctgcc | 60 |
| actgcctcca | ccctccctcc | tgacttcctc | tggggtttcg | ccactgccag | ctaccagatt | 120 |
| gagggtgctg | ttgatgagga | tggccgtgga | ccttccatct | gggatacctt | ctgcgctatc | 180 |
| cccggcaaga | ttgccgatgg | ctcttctggc | gatgttgctt | cgacagcta | ccaccgtacc | 240 |
| cacgaagata | ttgctctcct | caagtcctac | ggtgtcaacg | cctaccgctt | ctccatctcc | 300 |
| tggagccgta | tcatccctct | tggtggccgc | aacgaccctg | tcaacgagaa | gggcattgac | 360 |
| cactactcca | agttcgtcga | tgatttgctt | gctgctggta | tcaccccctt | cgtcaccctc | 420 |
| ttccactggg | atcttcccca | ggctctcgag | gaccgctacg | tggtctgct | caacaaggaa | 480 |
| gagttcgtcg | ccgacttcga | gaactacgcc | cgtgtcatgt | tcgagcgctt | cggtgaccgt | 540 |
| gtcaagcact | ggatcacctt | caacgagccc | tggtgctctt | ccgtccttgg | atacaacacc | 600 |
| ggccagttcg | ctcctggtcg | tacctccgac | cgcagcaagt | ccccgttgg | tgactcttcc | 660 |
| accgagccct | ggattgtcgg | ccacaacctg | cttgttgctc | acggtgctgc | cgtcaagatc | 720 |
| taccgtgagg | agttcaagcc | tacccagggt | ggtgagatcg | gtatcaccct | caacggtgac | 780 |
| tgggctgagc | cctgggaccc | cgagaacccc | gccgatgttg | aagcctgcga | ccgcaagatc | 840 |
| gagttcgcca | tctcctggtt | cgccgacccc | atctaccacg | gtgactaccc | tgacagcatg | 900 |
| cgcaagcagc | tcggtgaccg | tctgcccacc | ttcaccccg | aagaagtcgc | tctggtcaag | 960 |
| ggcagcaacg | acttctacgg | catgaaccac | tacactgcca | actacatccg | tcaccgtacc | 1020 |
| ggtgagcctg | accccaacga | cactgctggc | aacctggaga | tcctgctcca | gaacaagaac | 1080 |
| ggcaactcga | ttggtcccga | gactcagtcc | cctggctac | gccctcacgc | tcagggtttc | 1140 |
| cgcaagctcc | tcaactggct | ctccgaccgc | tacaactacc | caagatcta | cgtgaccgag | 1200 |
| aacggcacct | cgctgaaggg | tgagaacgac | ctccccttgg | agcagcttct | gaacgatgac | 1260 |
| ttccgtgtgc | agtacttccg | tgactacatc | ggtgccatgg | ccgatgccta | caccctcgat | 1320 |
| ggtgtcaacg | tccgtgccta | catggcctgg | tcgctgatgg | acaacttcga | atgggcggaa | 1380 |
| ggctacgaga | ctcgcttcgg | tgtgacctac | gttgactacg | agaacggcca | gaagcgctac | 1440 |
| cccaagaagt | ctgctctggt | catcggtgat | atcttcgaca | gcttgattga | gaaggcataa | 1500 |
| a | | | | | | 1501 |

<210> SEQ ID NO 26
<211> LENGTH: 499
<212> TYPE: PRT
<213> ORGANISM: Artificial Sequence
<220> FEATURE:
<223> OTHER INFORMATION: Beta-glucosidase variant ZTB-4

<400> SEQUENCE: 26

```
Met Ser Phe Arg Ser Leu Leu Ala Leu Ser Gly Leu Val Cys Thr Gly
1               5                   10                  15

Leu Ala Ser Ala Thr Ala Ser Thr Leu Pro Pro Asp Phe Leu Trp Gly
                20                  25                  30

Phe Ala Thr Ala Ser Tyr Gln Ile Glu Gly Ala Val Asp Glu Asp Gly
            35                  40                  45

Arg Gly Pro Ser Ile Trp Asp Thr Phe Cys Ala Ile Pro Gly Lys Ile
        50                  55                  60

Ala Asp Gly Ser Ser Gly Asp Val Ala Cys Asp Ser Tyr His Arg Thr
65                  70                  75                  80

His Glu Asp Ile Ala Leu Leu Lys Ser Tyr Gly Val Asn Ala Tyr Arg
                85                  90                  95

Phe Ser Ile Ser Trp Ser Arg Ile Ile Pro Leu Gly Gly Arg Asn Asp
            100                 105                 110

Pro Val Asn Glu Lys Gly Ile Asp His Tyr Ser Lys Phe Val Asp Asp
        115                 120                 125

Leu Leu Ala Ala Gly Ile Thr Pro Phe Val Thr Leu Phe His Trp Asp
130                 135                 140

Leu Pro Gln Ala Leu Glu Asp Arg Tyr Gly Gly Leu Leu Asn Lys Glu
145                 150                 155                 160

Glu Phe Val Ala Asp Phe Glu Asn Tyr Ala Arg Val Met Phe Glu Arg
                165                 170                 175

Phe Gly Asp Arg Val Lys His Trp Ile Thr Phe Asn Glu Pro Trp Cys
            180                 185                 190

Ser Ser Val Leu Gly Tyr Asn Thr Gly Gln Phe Ala Pro Gly Arg Thr
        195                 200                 205

Ser Asp Arg Ser Lys Ser Pro Val Gly Asp Ser Ser Thr Glu Pro Trp
210                 215                 220

Ile Val Gly His Asn Leu Leu Val Ala His Gly Ala Ala Val Lys Ile
225                 230                 235                 240

Tyr Arg Glu Glu Phe Lys Pro Thr Gln Gly Gly Glu Ile Gly Ile Thr
                245                 250                 255

Leu Asn Gly Asp Trp Ala Glu Pro Trp Asp Pro Glu Asn Pro Ala Asp
            260                 265                 270

Val Glu Ala Cys Asp Arg Lys Ile Glu Phe Ala Ile Ser Trp Phe Ala
        275                 280                 285

Asp Pro Ile Tyr His Gly Asp Tyr Pro Asp Ser Met Arg Lys Gln Leu
290                 295                 300

Gly Asp Arg Leu Pro Thr Phe Thr Pro Glu Glu Val Ala Leu Val Lys
305                 310                 315                 320

Gly Ser Asn Asp Phe Tyr Gly Met Asn His Tyr Thr Ala Asn Tyr Ile
                325                 330                 335

Arg His Arg Thr Gly Glu Pro Asp Pro Asn Asp Thr Ala Gly Asn Leu
            340                 345                 350

Glu Ile Leu Leu Gln Asn Lys Asn Gly Asn Ser Ile Gly Pro Glu Thr
        355                 360                 365

Gln Ser Pro Trp Leu Arg Pro His Ala Gln Gly Phe Arg Lys Leu Leu
370                 375                 380

Asn Trp Leu Ser Asp Arg Tyr Asn Tyr Pro Lys Ile Tyr Val Thr Glu
385                 390                 395                 400

Asn Gly Thr Ser Leu Lys Gly Glu Asn Asp Leu Pro Leu Glu Gln Leu
                405                 410                 415

Leu Asn Asp Asp Phe Arg Val Gln Tyr Phe Arg Asp Tyr Ile Gly Ala
```

```
                420             425             430
Met Ala Asp Ala Tyr Thr Leu Asp Gly Val Asn Val Arg Ala Tyr Met
                    435                 440                 445

Ala Trp Ser Leu Met Asp Asn Phe Glu Trp Ala Glu Gly Tyr Glu Thr
        450                 455                 460

Arg Phe Gly Val Thr Tyr Val Asp Tyr Glu Asn Gly Gln Lys Arg Tyr
465                 470                 475                 480

Pro Lys Lys Ser Ala Leu Val Ile Gly Asp Ile Phe Asp Ser Leu Ile
                    485                 490                 495

Glu Lys Ala

<210> SEQ ID NO 27
<211> LENGTH: 715
<212> TYPE: DNA
<213> ORGANISM: Artificial Sequence
<220> FEATURE:
<223> OTHER INFORMATION: Endoglucanase wild-type ZTC-WT

<400> SEQUENCE: 27
atgttcaagg ctctccttgc tgttggtttc gccattgctc tgaccttcgc ctccgctgct    60
cagaccatca ccggccagta cgactgcatt cctgctggtg cctacaccct tgccagaac    120
ctctggggtg agtacgctgg tgttggcagc cagaacagca ctctgatctc caccaacggc    180
aacgccgtca cctggcagac caactggacc tgggccaaca ccccaacac tgtcaagtcc     240
tgcgcttctc actctttccc cattgccagc tctgctccta ctgcctggaa ctggacctac    300
gtgaccgaga gccagggtat ccgtgccgat gtctcctacg acatctggtt cggcaaggcc    360
cagtccggca accccgccac ctccgccagc agctacgaga tcatgatctg gctatccggt    420
cttggtggta tccagcccgt cggtcaccag atcctttccg gtctgaacat tgctggtcac    480
acctggaacc tctggtccgg tcccaactcc aactggcagg tcttctcctt cgtcatctcc    540
tctggcgagg tccgcaactt ctctgccgac ctcaacgagt tcttccagta cctgatccag    600
tcccagggtg ttgcctccac tcagtacctc caggccatcc aggtcggtac tgagcccttc    660
gtcggctctg cctccctcct gaccgagtcc ttcgctgttg ctgtcaatgt ttaaa         715

<210> SEQ ID NO 28
<211> LENGTH: 237
<212> TYPE: PRT
<213> ORGANISM: Artificial Sequence
<220> FEATURE:
<223> OTHER INFORMATION: Endoglucanase wild-type ZTC-WT

<400> SEQUENCE: 28

Met Phe Lys Ala Leu Leu Ala Val Gly Phe Ala Ile Ala Leu Thr Phe
1               5                   10                  15

Ala Ser Ala Ala Gln Thr Ile Thr Gly Gln Tyr Asp Cys Ile Pro Ala
            20                  25                  30

Gly Ala Tyr Thr Leu Cys Gln Asn Leu Trp Gly Glu Tyr Ala Gly Val
        35                  40                  45

Gly Ser Gln Asn Ser Thr Leu Ile Ser Thr Asn Gly Asn Ala Val Thr
    50                  55                  60

Trp Gln Thr Asn Trp Thr Trp Ala Asn Asn Pro Asn Thr Val Lys Ser
65                  70                  75                  80

Cys Ala Ser His Ser Phe Pro Ile Ala Ser Ser Ala Pro Thr Ala Trp
                85                  90                  95

Asn Trp Thr Tyr Val Thr Glu Ser Gln Gly Ile Arg Ala Asp Val Ser
```

```
               100                 105                 110
Tyr Asp Ile Trp Phe Gly Lys Ala Gln Ser Gly Asn Pro Ala Thr Ser
            115                 120                 125

Ala Ser Ser Tyr Glu Ile Met Ile Trp Leu Ser Gly Leu Gly Gly Ile
        130                 135                 140

Gln Pro Val Gly His Gln Ile Leu Ser Gly Leu Asn Ile Ala Gly His
145                 150                 155                 160

Thr Trp Asn Leu Trp Ser Gly Pro Asn Ser Asn Trp Gln Val Phe Ser
                165                 170                 175

Phe Val Ile Ser Ser Gly Glu Val Arg Asn Phe Ser Ala Asp Leu Asn
            180                 185                 190

Glu Phe Phe Gln Tyr Leu Ile Gln Ser Gln Gly Val Ala Ser Thr Gln
        195                 200                 205

Tyr Leu Gln Ala Ile Gln Val Gly Thr Glu Pro Phe Val Gly Ser Ala
    210                 215                 220

Ser Leu Leu Thr Glu Ser Phe Ala Val Ala Val Asn Val
225                 230                 235

<210> SEQ ID NO 29
<211> LENGTH: 736
<212> TYPE: DNA
<213> ORGANISM: Artificial Sequence
<220> FEATURE:
<223> OTHER INFORMATION: Endoglucanase variant ZTC-5

<400> SEQUENCE: 29
atgttcaagg ctctccttgc tgttggtttc gccattgctc tgaccttcgc ctccgctcag      60
accttgactg gccagtacga ctgcgctcct gctggtgcct acaccctctg ccagaacctc     120
tggggtgagg acaacggtgt tggcagccag aactcgaccc tcatctccac ttctggcaac     180
accatctcct ggtccaccac ctacacctgg gccaacaacc caacgatgt caagtcctac      240 gccaacgtcc tctccaacac tgccaagggc atgaccctct ctgccgtccg cgctgctcct     300
accacctggc agtgggaata cgagagcaag tcctccggtc tgcgcgccga tgtctcctac     360
gacatctggt tcggtactgc tccctccggt gaccccgcca cttctgcttc ttcctacgag     420
atcatgatct ggctatccca gcgtggtggt atccagcctg ttggcagcaa gatcctctcc     480
ggtatctccg ttgctggcca cacctggaac tctctacgag gtcccaactc caactgggaa     540
acctactctt tcgtcagcgc cgatggtgac attcgtgact ccgtgccga tctgaaggac      600 ttcttcgact accttgttga gaacgagggt gtctccgaca gccagtacct gcaggccatt     660
cagactggta ccgagcccct tcaccggctct gccaccctca acgtcgagtc cttctccgtt    720
gccgtcaatg tctaaa                                                     736

<210> SEQ ID NO 30
<211> LENGTH: 244
<212> TYPE: PRT
<213> ORGANISM: Artificial Sequence
<220> FEATURE:
<223> OTHER INFORMATION: Endoglucanase variant ZTC-5

<400> SEQUENCE: 30

Met Phe Lys Ala Leu Leu Ala Val Gly Phe Ala Ile Ala Leu Thr Phe
1               5                   10                  15

Ala Ser Ala Gln Thr Leu Thr Gly Gln Tyr Asp Cys Ala Pro Ala Gly
            20                  25                  30

Ala Tyr Thr Leu Cys Gln Asn Leu Trp Gly Glu Asp Asn Gly Val Gly
```

-continued

```
                35                  40                  45
Ser Gln Asn Ser Thr Leu Ile Ser Thr Ser Gly Asn Thr Ile Ser Trp
        50                  55                  60

Ser Thr Thr Tyr Thr Trp Ala Asn Asn Pro Asn Asp Val Lys Ser Tyr
65                  70                  75                  80

Ala Asn Val Leu Ser Asn Thr Ala Lys Gly Met Thr Leu Ser Ala Val
                85                  90                  95

Arg Ala Ala Pro Thr Thr Trp Gln Trp Glu Tyr Glu Ser Lys Ser Ser
                100                 105                 110

Gly Leu Arg Ala Asp Val Ser Tyr Asp Ile Trp Phe Gly Thr Ala Pro
            115                 120                 125

Ser Gly Asp Pro Ala Thr Ser Ala Ser Ser Tyr Glu Ile Met Ile Trp
    130                 135                 140

Leu Ser Gln Arg Gly Gly Ile Gln Pro Val Gly Ser Lys Ile Leu Ser
145                 150                 155                 160

Gly Ile Ser Val Ala Gly His Thr Trp Asn Leu Tyr Glu Gly Pro Asn
                165                 170                 175

Ser Asn Trp Glu Thr Tyr Ser Phe Val Ser Ala Asp Gly Asp Ile Arg
                180                 185                 190

Asp Phe Arg Ala Asp Leu Lys Asp Phe Phe Asp Tyr Leu Val Glu Asn
            195                 200                 205

Glu Gly Val Ser Asp Ser Gln Tyr Leu Gln Ala Ile Gln Thr Gly Thr
        210                 215                 220

Glu Pro Phe Thr Gly Ser Ala Thr Leu Asn Val Glu Ser Phe Ser Val
225                 230                 235                 240

Ala Val Asn Val
```

METHOD FOR IMPROVING THE YIELD OF A POLYPEPTIDE

CROSS REFERENCE TO RELATED APPLICATIONS

This application is a §371 National Stage Application of PCT/EP2010/052918, filed Mar. 8, 2010, which claims priority to European Application No. 09154783.6, filed Mar. 10, 2009.

FIELD OF THE INVENTION

The present invention relates to a method for improving the yield of a polypeptide. In particular, it relates to a method for improving the yield of a polypeptide by modifying the backbone of the polypeptide.

BACKGROUND OF THE INVENTION

Recent rapid developments in genome and meta-genome sequencing has resulted in a large number of genes which represent a wealth of potentially very interesting proteins. Problems to express these genes at a significant level hamper the exploration of the functionality of the proteins encoded by those genes and as a consequence prevent the potential exploitation of such proteins in an economical feasible way. Since in many cases the discovered genes originate from organism which are less suitable for large scale production or which are rather inaccessible to the present genetic engineering tools, it is highly desired to use well established production hosts for which gene transfer systems and well developed genetic engineering tools are available. In particular eukaryotes such as filamentous fungi and yeasts are widely used as cell factories in the production of proteins, in particular the production of extracellular proteins. Because of a long tradition of utilization several of these species are generally regarded as safe (GRAS), which makes them very interesting for manufacture of products for human use. However, despite substantial improvements, the production levels obtained for heterologous genes are often much lower than observed for homologous genes. Often there is no expression of protein at all.

Various techniques exist to increase levels of protein production. These include application of strong promoters, increase of copy number, optimal Kozak sequence, mRNA stabilizing elements, optimized codon usage (WO2008/000632) and gene. These strategies however generally do not guarantee that proteins can be produced at detectable levels. To date the most successful approach for producing heterologous proteins is to express them as translational fusion with an efficiently secreted homologous protein. Nevertheless production levels still lag significantly behind and in many cases expression levels are problematically low. In general low expression in the fermentation leads to lower yields in the recovery. Even if expression is optimized, the final mature protein product may still result in very low production yields due to large losses in the downstream processing. This may be the case when the expressed protein remains associated with the biomass. This results in high losses or alternatively requires use of costly, and sometimes undesirable use of detergents to solubilise the proteins.

BRIEF DESCRIPTION OF THE FIGURES

FIG. 1 provides also a representative map for other pKLPGE-expression plasmids. Indicated are the LAC4 promoter relative to the PGE encoding gene and the amdS selection marker cassette. The *E. coli* DNA can be removed by digestion with restriction enzyme SacII, prior to transformation.

FIG. 2 provides also a representative map for other pANPGE-expression plasmids. In addition are indicated sequences of the glaA promoter and the truncated GlaA and PGE encoding sequences encoding variant PGE enzymes according a method of the invention. The *E. coli* DNA can be removed by digestion with restriction enzyme NotI, prior to transformation of the *A. niger* strains.

FIG. 3 provides also a representative map for other pGBFINZDU-, pGBFINZTB- and pGBFINZTC-plasmids. Indicated are the glaA flanking regions relative to the amdS selection marker cassette. In addition are indicated sequences of the glaA promoter and the ZDU, ZTB and ZTC sequences encoding variant enzymes according a method of the invention. The *E. coli* DNA can be removed by digestion with restriction enzyme NotI, prior to transformation of the *A. niger* strains.

DESCRIPTION OF SEQ ID NUMBERS

Figure 1:
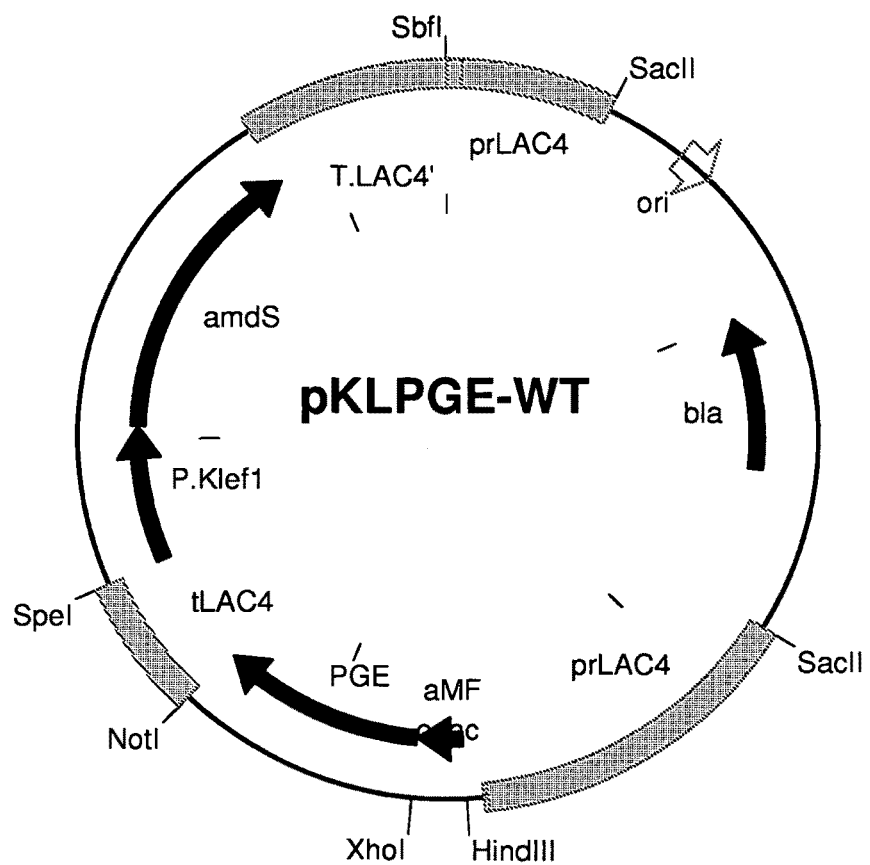
FIG. 1 depicts a plasmid map of *K. lactis* expression vector pKLPGE-WT (construction described in Example 1).

SEQ ID NO: 1: cDNA codon-pair optimized (CPO) pregastric esterase (PGE); processed, i.e. without signal sequence coding part
SEQ ID NO: 2: protein calf pregastric esterase (PGE), including signal sequence
SEQ ID NO: 3: DNA PGE protein feature optimized (PR)) variant KL8, 1 extra glycosylation site added
SEQ ID NO: 4: protein PGE PFO variant KL8, 1 extra glycosylation site added
SEQ ID NO: 5: DNA PGE PFO variant KL9, 5 extra glycosylation sites added
SEQ ID NO: 6: protein PGE PFO variant KL9, 5 extra glycosylation sites added
SEQ ID NO: 7: DNA PGE PFO variant KL11, pI shift of 6.96 to 7.74
SEQ ID NO: 8: protein PGE PFO variant KL11, pI shift of 6.96 to 7.74
SEQ ID NO: 9: DNA PGE PFO variant KL12, pI shift from 6.96 to 6.7
SEQ ID NO: 10: protein PGE PFO variant KL12, pI shift from 6.96 to 6.7
SEQ ID NO: 11: DNA PGE, PGE variant with native signal sequence fused to α-MAT factor signal pre(pro-)sequence
SEQ ID NO: 12: DNA PGE AN3, CPO gene tAG fusion with Kex site (KR)
SEQ ID NO: 13: DNA PGE variant AN12, pI shift from 6.96 to 4.6
SEQ ID NO: 14: protein PGE variant AN12, pI shift from 6.96 to 4.6
SEQ ID NO: 15: DNA PGE variant AN13, pI shift from 6.96 to 4.88
SEQ ID NO: 16: protein PGE variant AN13, pI shift from 6.96 to 4.88
SEQ ID NO: 17: DNA chitinase (ZDU) wild-type
SEQ ID NO: 18: protein chitinase (ZDU) wild-type
SEQ ID NO: 19: DNA chitinase variant ZDU-6
SEQ ID NO: 20: protein chitinase variant ZDU-6
SEQ ID NO: 21: DNA chitinase variant ZDU-7
SEQ ID NO: 22: protein chitinase variant ZDU-7
SEQ ID NO: 23: DNA beta-glucosidase wild-type ZTB-WT
SEQ ID NO: 24: protein beta-glucosidase wild-type ZTB-WT
SEQ ID NO: 25: DNA beta-glucosidase variant ZTB-4
SEQ ID NO: 26: protein beta-glucosidase variant ZTB-4
SEQ ID NO: 27: DNA endoglucanase wild-type ZTC-WT
SEQ ID NO: 28: protein endoglucanase wild-type ZTC-WT
SEQ ID NO: 29: DNA endoglucanase variant ZTC-5
SEQ ID NO: 30: protein endoglucanase variant ZTC-5

DETAILED DESCRIPTION

The present invention relates to a method for improving the secretion of a polypeptide of interest by a eukaryotic host cell by modifying the value of a set of relevant protein features in the amino acid backbone of the polypeptide to fall within an optimal range or to become more close to an optimal value for one or more protein features in the eukaryotic host.

One advantage is that proteins with interesting functionalities which before were not secreted or were only secreted in such low amounts that commercial application was unattractive, now become available for industrial processes because of their improved secretion. Another advantage is that downstream processing and recovery of polypeptides become easier since the designed polypeptides are already separated from the biomass.

In the present context, protein features are properties that can be computationally derived from the protein amino acid sequence and DNA sequence.

Modification of a polypeptide is herein defined as any event resulting in a change in the amino acid sequence of the polypeptide. A modification is construed as one or more modifications. Modification may be accomplished by the introduction (insertion), substitution or removal (deletion) of one or more amino acids in the polypeptide backbone.

In the present context, the term 'secretion' refers to the appearance of a polypeptide in the extracellular medium, typically the growth medium or production medium. The polypeptide which is secreted is free from the biomass. The level of secretion may be measured by methods known in the art, including by activity assays (units of activity), specific activity (units per weight protein), quantitative PAGE analysis, quantitative mass spectrometry and antibody assays.

The expression 'improvement of the secretion of a polypeptide' refers to an increase in the amount of polypeptide which is secreted in the extracellular medium of a cell. The improvement may be reflected by the fact that a polypeptide which is normally not secreted, such as for example an intracellular polypeptide, is now secreted. The improvement may also reside in the fact that a polypeptide which is expected to be secreted, for example because it contains a signal sequence, and which is not secreted, is now secreted. Improvement is of course always measured with reference to identical host genetic background and identical culture or fermentation conditions. In these cases, improved secretion may be clear from, for example, the appearance of a protein band in a polyacrylamide gel, where there was no band visible before improvement.

Alternatively, the improvement may be reflected by the fact that a polypeptide which is secreted in very low amounts, shows increased levels of secretion.

In one embodiment, the amount of polypeptide secreted is determined by measuring the activity of the polypeptide in the extracellular medium. In comparison to the situation before improvement, the activity in the extracellular medium may be increased by at least 5%, at least 10%, at least 15% or at least 20%. Preferably the activity is increased by at least 25%, at least 30%, at least 35% or at least 40%. In a more preferred embodiment, the activity is at least 45%, at least 50%, at least 60%, at least 70%, at least 80%, at least 90%, at least 100%, at least 200%, at least 500% or at least 1000% increased. The activity may be increased from no activity to some activity in the extracellular medium.

Any eukaryotic cell may be used in the method of the invention. Preferably, the eukaryotic cell is a mammalian, insect, plant, fungal, or algal cell. Preferred mammalian cells include e.g. Chinese hamster ovary (CHO) cells, COS cells, 293 cells, PerC6 cells, and hybridomas. Preferred insect cells include e.g. Sf9 and Sf21 cells and derivatives thereof. More preferably, the eukaryotic cell is a fungal cell, i.e. a yeast cell, such as *Candida, Hansenula, Kluyveromyces, Pichia, Saccharomyces, Schizosaccharomyces,* or *Yarrowia* strain. More preferably from *Kluyveromyces lactis, S. cerevisiae, Hansenula polymorpha, Yarrowia lipolytica* and *Pichia pastoris*, or a filamentous fungal cell. Most preferably, the eukaryotic cell is a filamentous fungal cell.

"Filamentous fungi" include all filamentous forms of the subdivision *Eumycota* and *Oomycota* (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Thermoascus, Thielavia, Tolypocladium*, and *Trichoderma*.

Preferred filamentous fungal cells belong to a species of an *Aspergillus, Chrysosporium, Penicillium, Talaromyces* or *Trichoderma* genus, and most preferably a species of *Aspergillus niger, Aspergillus awamori, Aspergillus foetidus, Aspergillus sojae, Aspergillus fumigatus, Talaromyces emersonii, Aspergillus oryzae, Chrysosporium lucknowense, Trichoderma reesei* or *Penicillium chrysogenum*. When the host cell according to the invention is an *Aspergillus* host cell, the host cell preferably is CBS 513.88 or a derivative thereof.

Several strains of filamentous fungi are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL) *Aspergillus niger* CBS 513.88, *Aspergillus oryzae* ATCC 20423, IFO 4177, ATCC 1011, ATCC 9576, ATCC14488-14491, ATCC 11601, ATCC12892, *P. chrysogenum* CBS 455.95, *Penicillium citrinum* ATCC 38065, *Penicillium chrysogenum* P2, *Talaromyces emersonii* CBS 124.902, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* ATCC44006 and derivatives thereof.

In one embodiment of the invention, *A. niger* or *K. lactis* is used.

In one embodiment, the eukaryotic cell is a host cell in which the polypeptide is produced by recombinant technology. Suitable methods for transforming or transfecting host cells can be found in Sambrook, et al. (*Molecular Cloning: A Laboratory Manual*, $2^{nd}$, ed. Cold Spring Harbor Laboratory, Cold Spring Harbor Laboratory Press, Cold Spring Harbor, N.Y., 1989), Davis et al., *Basic Methods in Molecular Biology* (1986) and other laboratory manuals. Accordingly, the present invention also relates to a method for the production of a polypeptide of interest by applying a method according to the invention to improve the secretion of the polypeptide to the polypeptide of interest and producing the polypeptide modified according to the invention by recombinant technology. The present invention also relates to said recombinantly produced polypeptide. The present invention also relates to a polypeptide obtainable by a method according to the invention to improve the secretion of the polypeptide; preferably said polypeptide is obtained by a method according to the invention to improve the secretion of the polypeptide.

The polypeptide of interest of which the secretion is improved according to a method of the invention may be any polypeptide having a biological activity of interest. The polypeptide may be a collagen or gelatin, or a variant or hybrid thereof. The polypeptide may be an antibody or parts thereof, an antigen, a dotting factor, an enzyme, a hormone or a hormone variant, a receptor or parts thereof, a regulatory protein, a structural protein, a reporter, or a transport protein such as serum albumin, e.g. Bovine Serum Albumin and Human Serum Albumin, or such as a transferrin, e.g. lactoferrin, a protein involved in secretion process, a protein involved in folding process, a chaperone, a peptide amino acid transporter, a glycosylation factor, a transcription factor, a synthetic peptide or oligopeptide, a protein which in its native form is an intracellular protein and is secreted by methods known in the art such as fusion to a signal peptide and fusion to a polypeptide that is already secreted in its native form. Such intracellular protein may be an enzyme such as a protease, ceramidases, epoxide hydrolase, aminopeptidase, acylases, aldolase, hydroxylase, aminopeptidase, lipase. The polypeptide may be an enzyme secreted extracellularly in its native form. Such enzymes may belong to the groups of oxidoreductase, transferase, hydrolase, lyase, isomerase, ligase, catalase, cellulase, chitinase, cutinase, deoxyribonuclease, dextranase, esterase. The enzyme may be a carbohydrase, e.g. cellulases such as endoglucanases, β-glucanases, cellobiohydrolases or β-glucosidases, hemicellulases or pectinolytic enzymes such as xylanases, xylosidases, mannanases, galactanases, galactosidases, pectin methyl esterases, pectin lyases, pectate lyases, endo polygalacturonases, exopolygalacturonases rhamnogalacturonases, arabanases, arabinofuranosidases, arabinoxylan hydrolases, galacturonases, lyases, or amylolytic enzymes; hydrolase, isomerase, or ligase, phosphatases such as phytases, esterases such as lipases, proteolytic enzymes, oxidoreductases such as oxidases, transferases, or isomerases. The enzyme may be a phytase. The enzyme may be an aminopeptidase, asparaginase, amylase, carbohydrase, carboxypeptidase, endo-protease, metallo-protease, serine-protease catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, protein deaminase, invertase, laccase, lipase, mannosidase, mutanase, oxidase, pectinolytic enzyme, peroxidase, phospholipase, polyphenoloxidase, ribonuclease, transglutaminase, or glucose oxidase, hexose oxidase, monooxygenase. The polypeptide of which the secretion is improved may be homologous or heterologous to the host cell. A suitable example of a homologous polypeptide is an *Aspergillus niger* protein which is cloned into and produced by an *Aspergillus niger*. Suitable examples of heterologous expression include a bacterial polypeptide, for example from *E. coli* or *Bacillus*, cloned into and produced by a filamentous fungus or a yeast, or a mammalian protein, for example from bovine or goat, which is cloned into and produced by a filamentous fungus or a yeast, or a filamentous fungal polypeptide which is cloned and produced by a yeast, or a filamentous fungal protein which is cloned into and produced by another fungus. Preferably, the nucleic acids encoding the polypeptides are optimized, for example by codon pair optimization, for expression in the relevant host cell. Codon-pair optimization is a method wherein the nucleotide sequences encoding a polypeptide have been modified with respect to their codon-usage, in particular the codon-pairs that are used, is to obtain improved expression of the nucleotide sequence encoding the polypeptide and/or improved production of the encoded polypeptide. Codon pairs are defined as a set of two subsequent triplets (codons) in a coding sequence. Codon-pair optimization is preferably performed as described in WO2008/000632.

Preferably, the specificity of the modified polypeptide is substantially the same as before the improvement of secretion. This means for example that substrate specificity or binding specificity is substantially maintained. In this context, the term "substantially maintained" means that more than 60%, more than 65%, more than 70% or more than 75% of the specificity is maintained. Preferably more than 80%, 85% or 90% of the specificity is maintained. Most preferably, more than 95%, 96%, 97%, 98% or 99% of the specificity is maintained.

According to the method of the invention, the level of activity in the extracellular medium is increased, which is an indication of improved secretion. However, specific activity of the modified polypeptide does not have to be increased, as long as it is not decreased. Therefore, specific activity is preferably substantially the same as or higher than before the improvement of secretion. In a preferred embodiment, specific activity is substantially the same as before improvement. In this context the phrase 'substantially the same level of activity' refers to a level of activity which differs less than 15%, preferably less than 12% or less than 10%, more preferably less than 8%, less than 6% or less than 4% from the level of activity of the parent polypeptide.

In the present context, the terms 'polypeptide' and protein' are used interchangeably. Any type of polypeptide may have its secretion improved by the method of the invention. In a preferred embodiment, the polypeptide is one of the list cited earlier herein.

According to the method of the invention, the value of a set of relevant protein features in the amino acid backbone is modified to fall within an optimal range or to become more close to an optimal value for one or more protein features in the eukaryotic host.

The amount of change of a protein feature between a modified polypeptide and a reference polypeptide can be defined in two ways: relative improvement (RI) and normalized relative improvement ($RI_N$)

RI of a protein feature is defined in terms of absolute deviation (D) of a protein feature from the optimal value:

$RI=(D_{REF}-D_{PFO})/D_{REF}$, where $D=|F_{POI}-F_{OPT}|$, $F_{POI}$ is the value of the feature of the protein of interest, being either the reference or the PFO, $F_{OPT}$ is the optimal feature value.

$RI_N$ is defined in terms of normalized deviation ($D_N$) to make sense which features matter substantially. $D_N$ takes into account the upper bound (UB) and lower bound (LB) of a feature value (see Table 1).

$RI_N=D_{N,REF}-D_{N,PFO}$, where $D_N=(F_{POI}-F_{OPT})/(UB-F_{OPT})$ if $F_{POI}>F_{OPT}$ $D_N=(F_{POI}-F_{OPT})/(LB-F_{OPT})$, if $F_{POI}<F_{OPT}$ According to the method of the invention, modifications are made to the polypeptide backbone. In this context, the term "backbone" refers to the regular structure which is formed when amino acids are linked together through peptide bonds and form a sequence of covalently linked amino acids. In the present invention, preferably the backbone of the mature polypeptide is modified. In the context of the present invention "mature polypeptide" is defined herein as a polypeptide that is in its final functional form following translation and any post-translational modifications, such as N-terminal processing, C-terminal truncation, glycosylation, phosphorylation, etc. The polypeptide before modification is referred to as the parent or reference or wild-type polypeptide to distinguish it from the modified polypeptide which results from it. The terms "parent-", "wild-type-" and "reference-polypeptide" are used interchangeably herein. When the polypeptide is a chimeric polypeptide, i.e. a translational fusion with an efficiently secreted polypeptide, preferably a polypeptide native to the host cell, the entire chimeric polypeptide may be modified according to the invention. When the chimeric polypeptide comprises an efficiently secreted polypeptide as a leader polypeptide fused to polypeptide of interest, the polypeptide of interest is preferably modified.

As is known to the person skilled in the art it is possible that the N-termini of the mature polypeptide might be heterogeneous as well as the C-terminus of the mature polypeptide due to processing errors during maturation. In particular such processing errors might occur upon overexpression of the polypeptide. In addition, exo-protease activity might give rise to heterogeneity. The extent to which heterogeneity occurs depends also on the host and fermentation protocols that are used. Such N-terminal and C-terminal processing artefacts might lead to shorter polypeptides or longer polypeptides compared with the expected mature polypeptide.

In one embodiment of the invention, the method comprises:
  (i) determining an optimal range and an optimal value for one or more protein features in the eukaryotic host, and
  (ii) determining a set of relevant protein features in the eukaryotic host, which features will improve the secretion of the polypeptide by the eukaryotic host if one or more of these relevant features is modified in the amino acid backbone of the polypeptide, and
  (iii) modifying the value of the relevant protein features to fall within the optimal range or more close to the optimal value as determined in (i), wherein (i) and (ii) may be performed in any order.

Any method may be used to determine the set of relevant features. In one embodiment, a relevant set of features to improve the secretion of a polypeptide is determined as follows:
  (i) collecting or creating a dataset S, which contains the secretion levels of a suitable amount of proteins in a certain eukaryotic host and the amino acid and DNA sequences of these proteins. Dataset S may contain secreted proteins (S+). Preferably, dataset S also contains non-secreted proteins (S−). For example, one can express all predicted secreted proteins in *A. niger* (Tsang et al., 2009, Fungal Genetics and Biology, 46: S153-160). The proteins that are secreted belong to the set S+, while the proteins that are not secreted belong to the set S−. Any method can be used to measure the level of secretion. Alternatively, the set S− may contain non-secretary proteins known in the literature in the eukaryotic host. The proteins in S may be homologous or heterologous to the eukaryotic host.
  (ii) Computing protein features (F) for all proteins in the dataset S. F may be derived both from the DNA sequence and the amino acid sequences of these proteins;
  (iii) Using statistical classification methods to select a subset of protein features computed in ii) (Fs) that gives the best performance of a statistical classifier to distinguish between S+ and S−, according to a suitably defined classifier performance criterion. Fs might be derived both from the DNA sequence (Fs_DNA) and the amino acid sequence (Fs_AA);

The protein features in Fs_AA are the relevant features for modification to improve protein secretion in the corresponding eukaryote host.

Since preferably, the backbone of the mature polypeptide is modified according to the method of the invention, the protein features are preferably computed from a set of mature proteins.

Standard statistical classification methods, which are well known in the art, can be used, such as Linear Discriminant Classifier (LDC), Quadratic Discriminant Classifier (QDC), Nearest Mean Classifier (NMC), 1-/k-Nearest Neighbour classifiers, support vector machine and decision tree, etc (Webb, Statistical Pattern Recognition, $2^{nd}$ ed, John Wiley & sons). When applying such methods, the dataset S might be divided into a training dataset and a validation dataset and validation schemes well known in the art (such as 10-fold cross validation) may be used.

Any classifier performance measures known in the art may be used, for example, specificity, sensitivity, accuracy, precision and Area Under the Receiver Operation Characteristics (ROC) curve.

Any suitable method may be used to determine an optimal range or an optimal value of protein features.

In one embodiment, an optimal range or an optimal value of protein features for a eukaryotic host are determined as follows:

i) Collecting or creating a dataset S, which contains the secretion levels of a suitable amount of proteins in a certain eukaryotic host and the amino acid and DNA sequences of these proteins. Dataset S may contain secreted proteins (S+). Preferably, dataset S also contains non-secreted proteins (S−). For example, one can express all predicted secreted proteins in *A. niger* (Tsang et al., 2009, Fungal Genetics and Biology, 46: S153-160). The proteins that are secreted belongs to the set S+, while the proteins that are not secreted belongs to the set S−. Any method can be used to measure the level of secretion. Alternatively, the set S− may contain non-secretary proteins known in the literature in the eukaryotic host. The proteins in S may be homologous or heterologous to the eukaryotic host.

ii) Computing protein features (F) for all proteins in the dataset S. F may be derived both from the DNA sequence and the amino acid sequences of these proteins;

iii) Determining an optimal value (F_opt) for each feature for the corresponding eukaryote host: The optimal value may also be obtained by computing measures of central tendency of each protein feature computed from S+. Any measures of central tendency can be used, for example, geometric mean, harmonic mean, arithmetic mean, trimmed mean, most frequent value and the median. The computed measure for central tendency is an optimal value for the feature for the corresponding eukaryotic host. Alternatively, fit a probability distribution for each protein feature computed from S+ such that the distribution of the feature values is well described by the chosen probability distribution. Any probability distribution can be used, for example normal distribution, exponential distribution, or log normal distribution can be used. The mean of the probability distribution is an optimal value for the feature for the corresponding eukaryote host.

iv) Determining an optimal range of each feature for the corresponding eukaryote host: considering the set S+ containing only secreted proteins, a lower bound of the optimal range for a protein feature is defined as the value corresponding to the 0.3-, 0.2-, 0.15 or preferably the 0.10- and 0.05-quantile of the protein feature computed from S+. Here the value 0.3, 0.2, 0.15, etc. refers to cumulative probabilities. Quantiles corresponding to a certain cumulative probability can be computed by any statistical methods, for example, using the quantile function of the Statistical Toolbox, Matlab R2007a (The Mathworks Inc). An upper bound of the optimal range of a protein feature is defined as the value corresponding to the 0.7-, 0.8-, 0.85 or preferably the 0.90- and 0.95-quantile of the protein feature computed from S+. Alternatively, considering the whole dataset S containing both secreted and non-secreted proteins, a lower bound of the optimal range for a protein feature may be defined as a value of the protein feature below which 70%, 80%, 85%, preferably 90% or 95% of the proteins in S is not secreted; an upper bound of the optimal range of a protein feature is defined as a value of the protein feature above which 70%, 80%, 85%, preferably 90% or 95% of the proteins in S is not secreted.

The set of relevant features and optimal ranges and values will vary from host cell to host cell. For *A. niger* the relevant protein features (Fs_AA) to be modified to increase protein secretion include, but are not limited to: basic amino acid frequency, polar amino acid frequency, non-polar amino acid frequency, tiny amino acid frequency, small amino acid frequency, charged amino acid frequency, net charge (at pH 7.2), isoelectric point, frequency of asparagine, arginine, isoleucine, cysteine, histidine, glutamine, valine, lysine, glycine, threonine and leucine, turn (as calculated by Garnier), PEST motif as calculated by EPESTFIND, local feature (LF) values for pI, in particular LF1 and LF6, LF values for Gravy score, in particular LF2 and LF4, LF values for aroma score, in particular LF3, LF4 and LF6, atomic composition w.r.t. sulphur (S) and localization features (e.g. predicted by MultiLoc localization prediction tool).

Net charge has the same unit as the charge of a proton. Net/net positive/net negative/total charge per length have the same unit as the charge of a proton, but normalized to the length of the polypeptide.

The net charge of a polypeptide is herein estimated assuming that all amino acids are fully exposed to the solvent, that neighboring peptides have no influence on the pK of any given amino acid, and that the constitutive amino acids, as well as the N- and C-termini, are unmodified. Different programs can be used to calculate the net charge of a polypeptide at a particular pH (by default pH=7.2), for example, by using the 'isoelectric' function of the Bioinformatics Toolbox of Matlab (version R2008b), or by using the 'pepstats' function of the EMBOSS Explorer, available at emboss.sourceforge.net/.

The net charge per length is herein defined as the net charge of a polypeptide divided by the length of the polypeptide.

The net positive charge per length is herein defined as the net positive charge of a polypeptide calculated by summing up the partial charges of the N-terminus and all lysine, arginine and histidine residues of a polypeptide at pH 7.2. The net positive charge per length is determined by dividing the net positive charge of a polypeptide by the length of the polypeptide.

The net negative charge per length is herein defined as the net negative charge of a polypeptide calculated by summing up the partial charges of the C-terminus and all aspartate, glutamate, cysteine and tyrosine residues of a polypeptide at pH 7.2. The net negative charge per length is determined by dividing the net negative charge of a polypeptide by the length of the polypeptide.

The total charge per length is herein defined as the total charge of a polypeptide calculated by subtracting the net positive charge of the polypeptide (a positive number) by the net negative charge of the polypeptide (a negative number). The total charge per length is determined by dividing the total charge of a polypeptide by the length of the polypeptide.

The gravy score is herein defined as the hydropathy index of a polypeptide as defined by Kyte and Doolittle (1982). Each amino acid has a hydrophobicity score between 4.6 and −4.6. 4.6 is assigned to the most hydrophobic and −4.6 to the most hydrophilic proteins. The GRAVY score of a polypeptide is preferably determined according to Kyte and Doolittle (1982). Kyte, J. and Doolittle, R. 1982 A simple method for displaying the hydropathic character of a protein. *J. Mol. Biol.*, 157: 105-132.

The Aroma score of a polypeptide is calculated herein by summing the frequencies of the three aromatic amino acids, Phe, Tyr and Trp in the polypeptide.

The aliphatic index is herein defined as the relative volume occupied by aliphatic side chains. The aliphatic index of a polypeptide (AI) is calculated according to the formula of Ikai (1980): AI=f_Ala+a f_Val+b (f_Ile+f_Leu). Amino acids alanine, valine, isoleucine and leucine have aliphatic side chains. Where a is the relative volume of the valine side chain (a=2.9) and b is the relative volume of the leucine and isoleucine side chains (b=3.9). f_Ala, f_Val, f_Ile and f_Leu are frequencies of alanine, valine, isoleucine and leucine in the polypeptide, respectively. Ikai, A. J. 1980 Thermostability and aliphatic index of globular proteins. *J. Biochem.*, 88: 1895-1898

For GRAVY and aliphatic one could also refer to *Protein Identification and Analysis Tools on the ExPASy Server*; Gasteiger E., Hoogland C., Gattiker A., Duvaud S., Wilkins M. R., Appel R. D., Bairoch A.; (In) *John M. Walker (ed): The Proteomics Protocols Handbook, Humana Press* (2005). pp. 571-607.

Classes of amino acids based on their physio-chemical properties:
Acidic: D, E
Aliphatic: A, I, L, V
Aromatic: F, W, Y
Basic: H, K, R
Charged: D, E, H, K, R
Non-polar: A, C, F, G, I, L, M, P, V, W, Y
Polar: D, E, H, K, N, Q, R, S, T
Small: A, C, D, G, N, P, S, T, V
Tiny: A, C, T, S, G The features based on the composition of single elements in a sequence are calculated from the frequency fi of the element i. Frequency and fraction are herein used interchangeably. The frequency is defined as number of times ni an element i occurs in a sequence divided by the total number of elements in the sequence. Single elements e.g. amino acids in the sequences can be combined to multiple elements e.g. tiny, acidic.

The surface accessibility of an amino acid residue within a polypeptide can be determined by any method known in the art.

If the polypeptide has an experimentally solved structure, the solvent accessible surface area (ASA) is given in Å2 and the area is calculated by rolling a sphere the size of a water molecule over the protein surface [1]. The ASA is then transformed to a relative surface area (RSA), which is calculated as the ASA of a given amino acid residue in the polypeptide chain, relative to the maximal possible exposure of that residue in the centre of a tri-peptide flanked with either glycine [2] or alanine [3]. A residue with an RSA greater than a threshold value alpha (RSA>=alpha, 0<=alpha<=1) is said to be exposed, while a residue with an RSA less than a threshold value beta (RSA<=alpha, 0<=beta<=1) is said to be buried. Preferably, alpha>=0.25, more preferably alpha=0.25. Preferably beta<=0.25, more preferably beta=0.25.

The surface accessibility can also be predicted from the amino acid sequence of a polypeptide, if the structure of the polypeptide is not available. Different methods are available in the literature to predict the surface accessibility from the amino acid sequence of a polypeptide, for example, as described in [3], [4], [5] and [6]. Preferably, the RSA is predicted using the so-called NetSurfP method described in [4], which can be accessed online www.cbs.dtu.dk/services/NetSurfP/. In this application, surface accessibility is predicted from the amino acid sequence of the mature protein. The definition of exposed and buried residues is the same as before.

[1] Connolly M: Analytical molecular surface calculation. Journal of Applied Crystallography 1983, 16(5):548-558.
[2] Chothia C: The nature of the accessible and buried surfaces in proteins. J Mol Biol 1976, 105(1):1-12.
[3] Ahmad S, Gromiha M M, Sarai A: Real value prediction of solvent accessibility from amino acid sequence. Proteins 2003, 50(4):629-635.
[4] Bent Petersen et al: A generic method for assignment of reliability scores applied to solvent accessibility predictions. BMC Structural Biology 2009, 9: 51.
[5] Dor O, Zhou Y: Real-SPINE: an integrated system of neural networks for real-value prediction of protein structural properties. Proteins 2007, 68(1):76-81.
[6] Faraggi E, Xue B, Zhou Y: Improving the prediction accuracy of residue solvent accessibility and real-value backbone torsion angles of proteins by guided-learning through a two-layer neural network. Proteins 2009, 74(4): 847-856.

Optimal values and ranges for *A. niger* are presented in Table 1.

TABLE 1

Lower bound (LB), upper bound (UB) and optimal values ($F_{OPT}$) of protein features

|  | Whole protein | | | Mature protein | | |
| --- | --- | --- | --- | --- | --- | --- |
|  | $F_{OPT}$ | LB | UB | $F_{OPT}$ | LB | UB |
| pI | 4.46 | 3.46 | 6.21 | 4.39 | 3.86 | 5.26 |
| Net charge | −21.20 | −66.10 | −4.7 | −22.11 | −36.26 | −9.50 |
| Net charge per length | −0.040 | −0.150 | −0.01 | −0.047 | −0.080 | −0.024 |
| Net positive charge per length | NA | NA | NA | 0.063 | 0.044 | 0.082 |
| Net negative charge per length | NA | NA | NA | −0.113 | −0.137 | −0.091 |
| Total charge per length | NA | NA | NA | 0.176 | 0.147 | 0.212 |
| Gravy score | −0.22 | −0.55 | 0.06 | −0.280 | −0.439 | −0.118 |
| Aroma score | 0.110 | 0.070 | 0.17 | 0.111 | 0.083 | 0.133 |
| Aliphatic index | 0.750 | 0.450 | 0.93 | 0.728 | 0.606 | 0.822 |
| Tiny | 0.356 | 0.264 | 0.505 | 0.351 | 0.305 | 0.430 |
| Small | 0.588 | 0.525 | 0.714 | 0.588 | 0.550 | 0.664 |
| Polar | 0.443 | 0.398 | 0.512 | 0.452 | 0.425 | 0.493 |
| Non-polar | 0.557 | 0.488 | 0.602 | 0.548 | 0.507 | 0.575 |
| Charged | 0.181 | 0.096 | 0.271 | 0.187 | 0.156 | 0.224 |
| Acidic | 0.106 | 0.075 | 0.207 | 0.110 | 0.088 | 0.133 |
| Basic | 0.075 | 0.020 | 0.119 | 0.077 | 0.053 | 0.100 |
| Aliphatic | 0.186 | 0.110 | 0.236 | 0.181 | 0.150 | 0.208 |
| Ala | 0.089 | 0.042 | 0.155 | 0.081 | 0.059 | 0.106 |
| Arg | 0.029 | 0.006 | 0.049 | 0.029 | 0.014 | 0.045 |
| Asn | 0.055 | 0.032 | 0.099 | 0.056 | 0.041 | 0.074 |
| Asp | 0.061 | 0.040 | 0.142 | 0.063 | 0.048 | 0.085 |
| Cys | 0.013 | 0.000 | 0.066 | 0.013 | 0.005 | 0.024 |
| Gln | 0.035 | 0.012 | 0.09 | 0.036 | 0.020 | 0.050 |
| Glu | 0.042 | 0.019 | 0.078 | 0.044 | 0.031 | 0.063 |
| Gly | 0.087 | 0.068 | 0.136 | 0.088 | 0.072 | 0.108 |
| His | 0.017 | 0.000 | 0.072 | 0.018 | 0.008 | 0.031 |
| Ile | 0.047 | 0.022 | 0.083 | 0.047 | 0.033 | 0.064 |
| Leu | 0.075 | 0.023 | 0.12 | 0.069 | 0.049 | 0.091 |
| Lys | 0.028 | 0.000 | 0.071 | 0.028 | 0.016 | 0.044 |
| Met | 0.017 | 0.002 | 0.041 | 0.015 | 0.005 | 0.024 |
| Phe | 0.038 | 0.008 | 0.061 | 0.038 | 0.026 | 0.052 |
| Pro | 0.049 | 0.009 | 0.129 | 0.050 | 0.031 | 0.069 |
| Ser | 0.089 | 0.047 | 0.172 | 0.088 | 0.064 | 0.124 |
| Thr | 0.080 | 0.057 | 0.132 | 0.080 | 0.062 | 0.108 |

TABLE 1-continued

Lower bound (LB), upper bound (UB) and optimal values ($F_{OPT}$) of protein features

| | | | | | | |
|---|---|---|---|---|---|---|
| Trp | 0.021 | 0.000 | 0.045 | 0.021 | 0.011 | 0.033 |
| Tyr | 0.048 | 0.025 | 0.147 | 0.050 | 0.033 | 0.067 |
| Val | 0.063 | 0.034 | 0.102 | 0.063 | 0.048 | 0.080 |

| | Exposed residues | | | Buried residues | | |
|---|---|---|---|---|---|---|
| | $F_{OPT}$ | LB | UB | $F_{OPT}$ | LB | UB |
| pI | 4.16 | 3.63 | 4.93 | 5.43 | 4.11 | 7.47 |
| Net charge | −16.86 | −29.98 | −6.15 | −4.57 | −10.83 | 0.52 |
| Net charge per length | −0.037 | −0.066 | −0.016 | −0.010 | −0.023 | 0.001 |
| Net positive charge per length | 0.040 | 0.024 | 0.058 | 0.025 | 0.015 | 0.035 |
| Net negative charge per length | −0.078 | −0.102 | −0.060 | −0.036 | −0.048 | −0.025 |
| Total charge per length | 0.118 | 0.096 | 0.151 | 0.061 | 0.044 | 0.078 |
| Gravy score | −0.587 | −0.726 | −0.472 | 0.314 | 0.174 | 0.449 |
| Aroma score | 0.019 | 0.008 | 0.029 | 0.094 | 0.065 | 0.115 |
| Aliphatic index | 0.150 | 0.096 | 0.205 | 0.584 | 0.462 | 0.679 |
| Tiny | 0.172 | 0.131 | 0.256 | 0.179 | 0.138 | 0.207 |
| Small | 0.294 | 0.252 | 0.383 | 0.291 | 0.245 | 0.331 |
| Polar | 0.277 | 0.243 | 0.344 | 0.170 | 0.127 | 0.205 |
| Non-polar | 0.161 | 0.129 | 0.198 | 0.388 | 0.338 | 0.425 |
| Charged | 0.119 | 0.097 | 0.154 | 0.065 | 0.046 | 0.086 |
| Acidic | 0.076 | 0.057 | 0.098 | 0.033 | 0.021 | 0.044 |
| Basic | 0.044 | 0.025 | 0.065 | 0.032 | 0.018 | 0.047 |
| Aliphatic | 0.033 | 0.018 | 0.049 | 0.149 | 0.119 | 0.176 |
| Ala | 0.033 | 0.021 | 0.047 | 0.047 | 0.030 | 0.068 |
| Arg | 0.015 | 0.006 | 0.027 | 0.013 | 0.004 | 0.022 |
| Asn | 0.036 | 0.024 | 0.049 | 0.021 | 0.010 | 0.033 |
| Asp | 0.044 | 0.031 | 0.062 | 0.020 | 0.010 | 0.029 |
| Cys | 0.000 | 0.000 | 0.005 | 0.011 | 0.003 | 0.022 |
| Gln | 0.021 | 0.012 | 0.035 | 0.014 | 0.006 | 0.021 |
| Glu | 0.032 | 0.020 | 0.047 | 0.013 | 0.006 | 0.020 |
| Gly | 0.041 | 0.028 | 0.064 | 0.046 | 0.030 | 0.063 |
| His | 0.006 | 0.002 | 0.014 | 0.011 | 0.004 | 0.020 |
| Ile | 0.006 | 0.002 | 0.013 | 0.040 | 0.028 | 0.057 |
| Leu | 0.012 | 0.004 | 0.021 | 0.057 | 0.037 | 0.075 |
| Lys | 0.021 | 0.010 | 0.033 | 0.007 | 0.002 | 0.014 |
| Met | 0.002 | 0.000 | 0.006 | 0.012 | 0.004 | 0.021 |
| Phe | 0.004 | 0.000 | 0.009 | 0.034 | 0.023 | 0.046 |
| Pro | 0.028 | 0.016 | 0.042 | 0.023 | 0.011 | 0.033 |
| Ser | 0.052 | 0.032 | 0.088 | 0.034 | 0.019 | 0.048 |
| Thr | 0.045 | 0.030 | 0.069 | 0.034 | 0.022 | 0.049 |
| Trp | 0.002 | 0.000 | 0.006 | 0.019 | 0.008 | 0.029 |
| Tyr | 0.011 | 0.004 | 0.019 | 0.039 | 0.024 | 0.054 |
| Val | 0.013 | 0.006 | 0.023 | 0.050 | 0.035 | 0.066 |

In Table 1, all features computed from the whole protein sequence are based on the length of the whole protein. All features computed from the mature protein sequence, the exposed residues and the buried residues, are based on the length of the mature protein.

Preferably, the optimal values and ranges features are selected from Table 2; these features are referred to as the primary features, the other features, i.e. the features in Table 1 that are not in Table 2 are secondary features.

TABLE 2

| | Primary features | | | |
|---|---|---|---|---|
| | Computed from | | | |
| Feature | Whole protein | Mature protein | Exposed residues | Buried residues |
| pI | Y | Y | Y | |
| Net charge (pH 7.2) | Y | Y | Y | |

TABLE 2-continued

| | Primary features | | | |
|---|---|---|---|---|
| | Computed from | | | |
| Feature | Whole protein | Mature protein | Exposed residues | Buried residues |
| Net charge (pH 7.2) per length | Y | Y | Y | |
| Net positive charge (pH 7.2) per length | | Y | Y | |
| Net negative charge (pH 7.2) per length | | | Y | |
| Total charge (pH 7.2) per length | | Y | Y | |
| Gravy score | | | | |
| Aroma score | | | Y | |
| Aliphatic index | Y | Y | | Y |
| Tiny amino acid frequency | | | | Y |
| Small amino acid frequency | Y | Y | | Y |
| Polar amino acid frequency | | Y | | |
| Non-polar amino acid frequency | | Y | | |
| Charged amino acid frequency | Y | Y | Y | |
| Acidic amino acid frequency | | | | Y |
| Basic amino acid frequency | Y | Y | Y | |
| Arg | Y | Y | Y | |
| Gln | Y | | | |
| Glu | Y | Y | Y | |
| Lys | Y | Y | Y | |
| Met | | | | Y |
| Phe | | Y | Y | |
| Thr | | Y | Y | |

"Y": indicates that the feature is a primary feature in the corresponding column of either "whole protein" or "mature protein". All features computed from the whole protein sequence are based on the length of the whole protein. All features computed from the mature protein sequence, the exposed residues and the buried residues in the mature protein are based on the length of the mature protein.

For *K. lactis*, the preferred primary features are depicted in Table 3.

TABLE 3

Primary features and their values for mature proteins in *K. lactis*

| Feature | Optimal value |
|---|---|
| Glycosylation sites | 6 |
| gravy | −0.40 |
| polar amino acid frequency | 0.48 |
| nonpolar amino acid frequency | 0.52 |
| charged amino acid frequency | 0.25 |
| acidic amino acid frequency | 0.11 |
| basic amino acid frequency | 0.14 |
| Glu | 0.053 |
| Lys | 0.081 |
| Thr | 0.057 |

In another embodiment, the secretion of the polypeptide is improved by the following steps:
i) computing protein features for the polypeptide,
ii) determining if one or more protein features of the polypeptide are outside the optimal range or substantially deviate from the optimal value for the eukaryotic host, wherein substantial deviation is defined as a difference of 20%, 30%, 40% or more than 50% from the optimal value, iii) rationally changing the amino acid sequence of the polypeptide, such that the value of one or more Fs_AA of the polypeptide falls within the optimal range or is shifted towards the optimal value by a suitable amount, preferably a decrease in the difference between a protein feature of the polypeptide and the optimal value of the protein feature by 10%, 15%, 20%, or more than 30%.

Preferably, 2, 3, 4 or 5 protein features are modified in combination, more preferably, more than 10, 15 or 20 protein features are modified in combination. Most preferably, more than 25 or 30 protein features are modified in combination.

Preferably, the optimal range is taken from Table 1, more preferably, the optimal range is taken from Table 2. Alternatively, the optimal range is taken from Table 3.

In step iii) above, the amino acid sequence of the polypeptide may be rationally changed by any methods known in the art. For example, this may be achieved by:

(i) retrieving homologous sequences;
(ii) aligning the homologous sequences to the sequence of interest;
(iii) identifying amino acids which are crucial for the proteins functional properties;
(iv) introduce desired amino acid sequence features while retaining functional properties;
(vi) translating the final modified sequence back into the gene using the most optimal codons for the given host;
(vii) cloning and expression of the redesigned polypeptide in the host.

Preferably, at least 5% of the amino acids of the amino acid backbone is modified, more preferably at least 10%, even more preferably at least 15%, even more preferably at least 20% of the amino acids of the amino acid backbone is modified.

Preferably, at least 5 amino acids of the amino acid backbone is modified, more preferably at least 10 amino acids, even more preferably at least 15 amino acids, even more preferably at least 20 amino acids, even more preferably at least 25 amino acids, even more preferably at least 30 amino acids of the amino acid backbone is modified.

Preferably, according to the invention, primary features are improved while the secondary features are kept within a certain boundary. Therefore an overall optimality score F is defined based on $D_N$ values of all n primary features and all m secondary features:

$$F = \left( \sum_{i=1}^{n} |D_{N,i}|^p + \eta \sum_{j=1}^{m} |D_{N,j}|^p \right)^{1/p}$$

η is a weighing factor between and including 0 and 1 ($0 \leq \eta \leq 1$). Preferably $\eta \leq 0.5$, more preferably $\eta \leq 0.4$, most preferably $\eta = 0.3$. p is between and including 1 and 5 ($1 \leq p \leq 5$), preferably p=2 (F represents then the Euclidean distance). Preferably $\eta = 0.3$ and p=2. Preferably an improvement in F-score of at least 5% with respect to the wild type reference protein is achieved, more preferably at least 10%, even more preferably at least 15%, even more preferably at least 20% and even more preferably at least 30% improvement is achieved.

Preferably, at least 2, 3, 4, or 5 features are modified, more preferably at least 10, even more preferably at least 15, even more preferably at least 20, even more preferably at least 25, and even more preferably at least 30 features are modified.

Preferably, at least 2, 3, 4, or 5 features are improved, more preferably at least 10, even more preferably at least 15, even more preferably at least 20, even more preferably at least 25, and even more preferably at least 30 features are improved, whereas preferably, less than 10, even more preferably less than 5, even more preferably less than 4 features are worsened. Preferably, the features are primary features.

Homologous sequences are preferably retrieved by performing BLAST searches of appropriate sequences databases. The homologous sequences preferably have at least 30%, preferably at least 40%, more preferably at least 50%, 60%, 70%, 80%, 90%, 95,%, 96%, 97%, 98% or 99% identity with the sequence of interest. Most preferably, the homologous sequences preferably have about 50% identity with the sequence of interest. The person skilled in the art will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). Any method known in the art may be used for alignment. The percent identity between two amino acid sequences or between two nucleotide sequences may for example be determined using the Needleman and Wunsch algorithm for the alignment of two sequences. (Needleman, S. B. and Wunsch, C. D. (1970) J. Mol. Biol. 48, 443-453).

Methods to identify amino acids crucial for essential functional properties of interest are known in the art. Suitable tools include using a 3D structure or a 3D model of the protein of interest, mutagenesis studies of the protein of interest or of homologous proteins, the use of site saturated libraries to establish functionally neutral substitutions versus functional substitutions.

When introducing amino acid sequence features, substitutions are preferably chosen in such a way that at the given position the amino acid which is more conform the required amino acid sequence characteristics is selected from the group of amino acids which is observed in homologous sequences. State of the art modeling techniques may be applied to identify allowable substitutions which are not observed in natural homologues. Preferred references for modelling techniques which allow the generation of new sequences adopting a given fold are:

Kuhlman B, Dantas G, Ireton G C, Varani G, Stoddard B L, Baker D (2003). Design of a novel globular protein fold with atomic-level accuracy *Science* 302, 1364-8.

Baker D (2006). Prediction and design of macromolecular structures and interactions. *Philos. Trans. R. Soc. Lond., B, Biol. Sci.* 361, 459-63 De Novo protein design: towards fully automated sequence selection *Journal of Molecular Biology*, Volume 273, Issue 4, 7 Nov. 1997, Pages 789-796 Bassil I. Dahiyat, Catherine A. Sarisky, Stephen L. Mayo State of the art computational method allow for the generation of numerous potential sequences which may adopt a given protein fold. By introducing feature optimisation into the scoring functions which are used to filter out the most optimal sequences the most optimal sequences for a given production host might be selected in a computational way.

Protein features which may be modified according to the method of the invention include compositional, physiological and structural features. Suitable examples of such features are the number of amino acids, molecular weight, isoelectric point, net charge at a specific pH, GRAVY score, aliphatic index, instability index, compositional features, atomic composition with respect to C, H, N, O, S atoms, amino acid frequency, dipeptide frequency, tripeptide frequency, acidic amino acid frequency, aliphatic amino acid frequency, aromatic amino acid frequency, basic amino acid frequency, glycosylation pattern and charged amino acid frequency and the features as mentioned in Table 1. A combination of modified features is also encompassed by the present invention. Preferably 2, 3, 4 or 5 protein features are modified in combination. More preferably, more than 10, 15 or 20 protein features are modified in combination. Most preferably, more than 25 or 30 protein features are modified in combination.

In one embodiment of the invention, one or more glycosylation sites are introduced while other protein features are modified as well. In another embodiment of the invention, the charged amino acid frequency is modified while other protein features are modified as well. In another embodiment of the invention, the polar amino acid frequency is modified while other protein features are modified as well.

The protein feature computed from the entire amino acid or DNA sequence is an average value for the entire protein, which may not reveal local protein properties. For example, a protein could be on average hydrophilic but still contain a large internal hydrophobic region. Local protein properties can be computed from the amino acid or DNA sequence, for example, with the method outlined by Benita et al. (Benita et al., 2006. Molecular and Cellular Proteomics, 5: 1567-1580).

Figure 9:
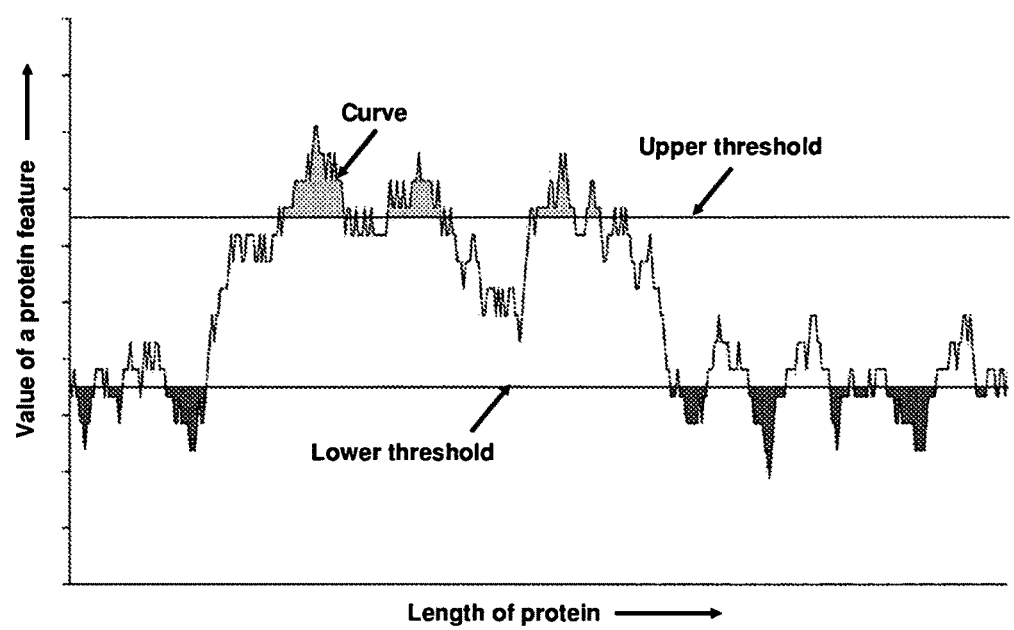
FIG. 9 depicts local protein features.

To compute the local property of a certain protein feature, one may compute the protein feature locally in a sliding window of a suitable number of amino acids or nucleotides. The obtained value is then plotted as a curve along the length of the amino acid or DNA sequence of the protein as illustrated in FIG. 9.

A number of local features can be defined:

| Local feature (LF) | Definition |
| --- | --- |
| LF1 | Area above the curve and below the lower threshold |
| LF2 | Area below the curve and above the higher threshold |
| LF3 | Largest continuous area above the curve and below the lower threshold |
| LF4 | Largest continuous area below the curve and above the higher threshold |
| LF5 | Fraction of the curve below the lower threshold |
| LF6 | Fraction of the curve above the upper threshold |

For example, LF1 corresponds to dark-gray colored area in FIG. 1, while LF2 corresponds to light-gray colored area in FIG. 1. The area can be calculated using the trapezoid method (Benita et al., 2006. Molecular and Cellular Proteomics, 5: 1567-1580).

For computing the local features a suitable upper and lower threshold, as well as the size of the sliding window can be chosen. The sliding window can be of any size. For example, a sliding windows size of 21 amino acids or base pairs can be used. The value of the upper and lower threshold can be chosen to reflect extreme peaks in the curve. For example, a higher upper threshold will take more extreme peaks into account than a lower one. Preferably, upper and lower thresholds are chosen such that the Fischer criteria is maximized for the dataset S+ and S−. The Fischer criteria ($J_F$) is defined as:

$$J_F = \frac{|\mu_{S-} - \mu_{S+}|^2}{\sigma_{S-}^2 + \sigma_{S+}^2}$$

Where $\mu_{S-}$ and $\mu_{S+}$ represent means of the local feature values computed from the set S− and S+, respectively, and $\sigma_{S-}^2$ and $\sigma_{S+}^2$ the variance of the local feature values computed from the set S− and S+, respectively.

Local features defined above can be calculated for any protein features, for example the Gravy score, aroma score and the isoelectric point.

In addition to the features that can be derived from the sequences of successfully secreted protein, it was observed that in particular increasing the hydrophilicity of the solvent accessible surface of target proteins was very successful in increasing the amount of soluble protein which was secreted form the cells. More specifically, not only the expression was increased, but also significantly more protein accumulated in the broth in a soluble form not attached to the biomass or other insoluble material. Given proteins with improved surface hydrophilicity could be recovered at significantly higher secretion. Upon removal of the biomass (by filtration or centrifugation) the major part of the produced protein ends up in the filtrate or the supernatant.

In creasing the hydrophilicity can be done by:
  substituting non-polar amino adds by more polar amino acids
  substituting less polar amino acids by more polar amino acids
  substituting polar amino acids by charged amino acids As such increasing the hydrophilicity by increasing the number of more polar or charged amino acids will change the amino acid composition and as such can be considered as compositional features which can be adapted in order to increase secretion.

Non-polar amino acids are selected from the group A, V, L, I, C, M, F. Amino acids G, P, Y, W can be considered as non-polar in a polar context and as polar in a non-polar context. More polar residues are selected from the group S, T, N, Q, D, E, H, R, K. Charged residues are selected from the group D, E, H, R, K. Acidic or negatively charged residues are selected from E, D. Basic or positively charged residues are selected from H, K, R. Using a comparative scale for polarity: [A, V, L, I, M, F, C]<[G, P, Y, W]<[S, T]<[N, Q, H]<[D, E, K, R].

It is known that highly hydrophobic surface regions tend to lead to undesired aggregation or undesired sticking to biomass resulting in high production stress in the production host, accumulation of protein in the host, and hampered secretion or no secretion at all. It was observed that substitutions which increase the overall hydrophilicity are very effective in secretion improvement in particular when these residues comprise solvent accessible residues (=protein surface residues). More specifically it was observed that when substituting non-polar residues for more polar residues in accessible surface regions, the fraction of polar residues might even exceed the fraction of polar residues set by the upper boundaries of the compositional features analysis. Non-compatibility of the target protein's sequence features with the host requirements may be compensated for by increasing the hydrophilicity of target protein, more specifically by introducing additional charge distributed in such a way that the positive and negative charge are evenly distributed over the surface preventing negative or positive charge hotspots.

Although some prediction tools are available for predicting which amino acids are likely to be on the surface given a certain amino acid sequence, the performance of these tools is quite poor when it is required to predict solvent accessible non-polar or hydrophobic patches. Therefore to modulate the hydrophilicity of the protein accessible surface a 3D structure or a 3D structural model is required. The 3D structure of protein can be determined by X-ray crystallography and by NMR. In addition comparative modelling or template based modelling can be applied to construct reliable 3D models for a given sequences based on 3D structures of homologous proteins (en.wikipedia.org/wiki/Homology modeling). Various servers and software packages for comparative modelling be found at: en.wikipedia.org/wiki/Protein structure prediction software.

For a recent review on protein structure prediction and modelling see Yang Zhang, Current Opinion in Structural Biology 2008, 18:342-348.

Given the atomic coordinates of a 3D structure or 3D model the accessible surface can be calculated by methods known in the art. A well known method is the calculation via a rolling-ball algorithm developed by Frederic Richards (1977, "Areas, volumes, packing and protein structure." Annu Rev Biophys Bioeng, 6:151-176). See also en.wikipedia.org/wiki/Accessible surface area For determination of the accessible surface the quaternary structure of the final mature protein should be considered in order to avoid that substitutions will disturb the interaction between the individual polypeptides (the monomers) in the multimer (e.g. dimer, trimer, tetramer etc)

Surface modulation comprises:
Spotting area's where non-polar residues are accessible from the solvent giving rise to potential sticky patches, which could hamper proper secretion and recovery.
Exclude those area's that play a functional role e.g. the active site in general and binding pockets for substrate, co-substrates and co-factors more in particular.
Substitute non-polar for more polar residues which include also charged residues
Substitution polar residues for more polar residues or charged residues.
Redistribution of charged residues in order to avoid region with high negative charge or regions with high positive charge
Instead of replacing hydrophobic surfaces patches, such regions may also be shielded by introducing glycosylation closely to the non-polar regions In case of the primary structure, increased hydrophilicity is represented by comparing number of polar residues before and after modification e.g.

|  | wt | variant |
|---|---|---|
| polar | 84 | 92 |
| charged | 40 | 44 |
| basic | 19 | 22 |
| acid | 21 | 22 |
| non-polar | 118 | 110 |

When considering the accessible surface the contribution of various polar amino acids can expressed as the fraction of the accessible surface formed by a particular amino acid or a particular group of amino acids with respect to the total accessible surface. For example, the total accessible surface of the charged residues can be calculated and compared to the total accessible surface area. By taking all the polar residues the polar accessible surface can be calculated. The hydrophilicity of the proteins surface is said to increase when the fraction of polar surface increases at the cost of non-polar surface.

In principle one can also introduce glycosylation and estimate the area which is shielded by the glycosylation. The distribution of charges may be done by any available method, including visual inspection.

In one embodiment, the features to be modified for improved secretion are surface charge (re)distribution, surface polar-non-polar distribution, sequence motifs, such as glycosylation, or a combination of these. The skilled person will understand that modification of one feature, for example an amino acid, will in many instances effect a modification of another feature, for example atomic composition with respect to C, H, N, O, S atoms.

It is to be understood that the methods according to the present invention can conveniently be combined with a state of the art technique to increase levels of protein production or with combinations of one or more of these techniques. These include but are not limited to application of strong promoters, increase of copy number, optimal Kozak sequence, mRNA stabilizing elements and optimized codon usage (WO2008/000632).

EXAMPLES

Strains

*A. niger* Strains:

WT 1: This *A. niger* strain is used as a wild-type strain. This strain is deposited at the CBS Institute under the deposit number CBS 513.88.

WT 2: This *A. niger* strain is a WT 1 strain comprising a deletion of the gene encoding glucoamylase (glaA). WT 2 was constructed by using the "MARKER-GENE FREE" approach as described in EP 0 635 574 B1. In this patent it is extensively described how to delete glaA specific DNA sequences in the genome of CBS 513.88. The procedure resulted in a MARKER-GENE FREE ΔglaA recombinant *A. niger* CBS 513.88 strain, possessing finally no foreign DNA sequences at all.

WT 3: To disrupt the pepA gene encoding the major extracellular aspartic protease PepA in WT 2, pepA specific DNA sequences in the genome of WT 2 were deleted, as described by van den Hombergh et al. (van den Hombergh J P, Sollewijn Gelpke M D, van de Vondervoort P J, Buxton F P, Visser J. (1997)—Disruption of three acid proteases in *Aspergillus niger*—effects on protease spectrum, intracellular proteolysis, and degradation of target proteins—Eur J. Biochem. 247 (2): 605-13). The procedure resulted in a MARKER-GENE FREE WT 3 strain, with the pepA gene inactivated in the WT 2 strain background.

WT 4: To delete the hdfA gene in WT 3, the method as earlier described in detail in WO05/095624 was used to generate *Aspergillus niger* WT 4 (ΔglaA, ΔpepA, ΔhdfA).

WT 5: This *A. niger* strain is a WT 4 strain comprising a deletion which results in an oxalate deficient *A. niger* strain. WT 5 was constructed by using the method as described in EP1157100 and U.S. Pat. No. 6,936,438, in which an oxalate deficient strain was obtained by deletion of the oahA gene, encoding oxaloacetate hydrolase, Strain WT 5 was selected as a representative strain with the oahA gene inactivated in the WT 4 strain background.

WT 6: This *A. niger* strain is a WT 5 strain comprising the deletion of three genes encoding alpha-amylases (amyB, amyBI and amyBII) in three subsequent steps. The construction of deletion vectors and genomic deletion of these three genes has been described in detail in WO2005095624. The vectors pDEL-AMYA, pDEL-AMYBI and pDEL-AMYBII, described in WO2005095624, have been used according the "MARKER-GENE FREE" approach as described in EP 0 635 574 B1. The procedure described above resulted in WT 6, an oxalate deficient, MARKER-GENE FREE ΔglaA, ΔpepA, ΔhdfA, ΔamyA, ΔamyBI and ΔamyBII amylase-negative recombinant *A. niger* CBS 513.88 strain, possessing finally no foreign DNA sequences at all. As such, strain WT 6 has a low amylase background, has a higher HR/NHR ratio for more efficient targeting of sequences and is more optimized for extracellular protein expression and detection compared to WT 1.

K. lactis Strains:

To assess the expression of PGE and its variants in K. lactis two strains were used. GG799 (New England Biolabs) and a derivative of K. lactis CBS 685.97, also called WT 7 herein, that is in more detail describe in the U.S. Pat. No. 6,265,186 B1. Strain K. lactis WT 7 was derived from CBS 685.97 by means of mutagenesis (classical strain improvement) and genetic engineering.

Chitinase Activity Assay

The reaction mix contained: 3 mg of chitin-azure (Sigma), 0.5 ml of 0.1 M Na-citrate-phosphate buffer, pH 5.0 and 0.1 ml of sample to be analyzed (culture liquid). The reaction mix was incubated for 24 hours at 37° C. with shaking, centrifuged for 10 min at 12000 rpm and the OD590 was measured.

Beta-Glucosidase Activity Using pNP-β-Glucopyranoside as a Substrate.

A 3 mM pNP-β-glucopyranoside (Sigma N7006) stock solution was prepared in 50 mM sodium acetate buffer pH=4.5. Assay: 250 µl substrate-stock (3 mM)+250 µL diluted enzyme sample was incubated at 40° C. Reactions were stopped at t=0, 10, 20 and 30 minutes by mixing 100 µl incubate with 100 µl 1M sodiumcarbonate. The extinction was determined at 405 nm using a MTP reader. Activity is expressed in µmol pNP released/ml/min Beta-Glucosidase Activity Using Cellobiose as Substrate.

A cellobiose (Sigma C7252) stock solution of 10 mM final concentration was prepared in 50 mM sodium acetate buffer pH=4.5. For the assay 2000 µl substrate-stock (10 mM)+100 µL diluted enzyme sample were mixed and incubated at 40° C. Reactions were stopped at t=0, 10, 20 and 30 minutes by mixing 100 µl incubate+100 µl 50 mM sodiumhydroxide. Samples were subjected to ultrafiltration and analyzed using High Performance Anion Exchange Chromatography with Pulsed Amperometric Detection (HPAEC-PAD), performed on a Dionex DX-500 equipped with an ED 40 pulsed amperometric detector. Activity is expressed in µmol glucose released/ml/min Endo-Glucanase Activity Using AZO-CM-Cellulose.

The assay is carried out according the Megazyme procedure S-ACMC 04/07 (Megazyme International Ireland Ltd, secure.megazyme.com/downloads/en/data/S-ACMC.pdf). Activity was measured on 2% AZO-CM-Cellulose in 100 mM sodium acetate buffer pH 4.6 at 40° C. For the assay 250 µL substrate stock (2%)+250 µL diluted enzyme solution were mixed. After 30 minutes 1250 µL of precipitant solution was added. Reactions were stopped by adding precipitant solution: 300 mM sodium acetate buffer pH=5 with 20 mM Zn-acetate in ethanol 76%. De extinction at 590 nm was measured of the supernatant after centrifugation at 1000×g for 10 minutes, using a spectrophotometer. Activity is expressed in µmol dye released/ml/min.

Tributyrine Plate Assay

The Rhodamine B lipase plate screening assay was done with tributyrin (C4) as a substrate. The Rhodamine B plate assay is commonly used for the screening of lipase activity presence in the samples and was adapted from assay described in literature (G. Kouker, K. E. Jaeger, Appl. and Environ. Microbiol, 1987, 211-213). All chemicals used were analytical grade. An arabic gum emulsion was made by dissolving 17.9 g NaCl and 0.41 g KH$_2$PO$_4$ in 400 ml of H$_2$O and finally 540 ml of glycerol (87%) was added. Six (6.0) g of Arabic gum was slowly added and after dissolving the total volume of 1000 ml was achieved by adding of H$_2$O.

Rhodamine B solution was prepared by dissolving Rhodamine B at concentration of 20 mg/ml in ethanol. A 4% agarose solution was prepared by dissolving 4 g agarose in 100 ml buffer solution (0.1 M Acetate pH=5.5) by heating. The substrate used to screen for lipase activity was tributyrin.

Plate assay procedure: 1 ml of substrate and 1.5 ml Arabic gum emulsion was mixed with 5 ml buffer solution and sonificated using a Soniprep with an amplitude of 20 micron for 2×60 sec or optionally an Ultraturax, set at green for 2 minutes. To this solution 7.5 ml of hot agarose solution was added together with 150 µl of Rhodamine B. The final solution was poured in a Petri dish plate. Plates were stored in the refrigerator until use. Just before use holes of 3 mm diameter were made using a replicator. 10 µl of solution to be checked for lipase activity was pipetted into a hole, after which the plate was incubated at 37° C. for 18-24 hours. The fluorescent halo around the hole is indicative for lipase activity.

pNP-Butyrate Assay

Pre-Gastric Esterase (PGE) activity was determined at 37° C. on a final concentration of 1 mM para-nitrophenyl butyrate as substrate against an internal enzyme standard. A substrate solution was prepared by making a 50 mM para-nitrophenyl butyrate stock solution in acetonitril, which was diluted five times in 0.1 M sodium phosphate buffer pH 6.7 containing 0.2% BSA and 2% Triton X-100. 120 µl of 0.1 M sodium phosphate buffer pH 6.7 containing 0.2% BSA, 15 µl of substrate solution was added. After preheating to 37° C., 15 µl of sample in an appropriate dilution was added (dilution in 0.1 M sodium phosphate buffer pH 6.7 containing 0.2% BSA), after which the absorbance increase over 5 minutes of incubation at 37° C. was measured spectrophotometrically at 405 nm. Sample responses were corrected for a blank background (incubation of 15 µl of 0.1 M sodium phosphate buffer pH 6.7 containing 0.2% BSA instead of sample) and typically ranged from 0.05 to 0.5 dAbs after blank correction.

The internal standard was calibrated in a titrimetric assay on tributyrin, performed at pH 6.0 and 30° C. Five ml of a PGE sample solution (prepared in milliQ water) were added to 30 mL of a pre-heated tributyrin/Arabic gum emulsion (93 and 57 g/L in water, respectively). Free fatty acid release was measured over 5 minutes by titration with 0.02 N NaOH.

SDS-PAGE Electrophoresis

Sample pre-treatment: 30 µl sample was added to 35 µl water and 25 µl NuPAGE™ LDS sample buffer (4×) Invitrogen and 10 µl NuPAGE™ Sample Reducing agent (10×) Invitrogen. Samples were heated for ten minutes at 70° C. in a thermo mixer.

SDS-PAGE was performed in duplicate according to the supplier's instructions (Invitrogen: Gel: 4-12% Bis-Tris gel, Buffer: MES SDS running buffer, Runtime: 35 minutes). One of the two gels was used for blotting, 10 µl of the sample solutions and 1 µl marker M12 (Invitrogen) were applied on the gels (NuPAGE™ BisTris, Invitrogen). The gels were run at 200V, using the XCELL Surelock, with 600 ml 20 times diluted MES-SDS buffer in the outer buffer chamber and 200 ml 20 times diluted MES-SDS buffer, containing 0.5 ml of antioxidant (NuPAGE™ Invitrogen) in the inner buffer chamber. After running, the gels were fixed for one hour with 50% Methanol/7% Acetic acid (50 ml), rinsed twice with demineralised water and stained with Sypro Ruby (50 ml, Invitrogen) overnight.

Images were made using the Typhoon 9200 (610 BP 30, Green (532 nm), PMT 600V, 100 micron) after washing the gel for ten minutes with demineralised water.

Western Blotting

PGE Polyclonal Antibody

PGE polyclonal antibodies were ordered at Eurogentec (Belgium) using the speedy 28-days program and two synthesized PGE peptides as antigens. The PGE antibody was validated against the commercial Piccantase C (DFS) enzyme preparation (data not shown).

Western blotting was performed according to method of analysis S2300.

membrane: NC 0.45 μm
Runtime: 90 minutes at 25V
Buffer: transfer buffer with methanol After the transfer to the membrane the following steps were performed:
Block the membrane in 20 ml skim milk (1% skim milk in PBST; 10 mM PBS+0.05% TWEEN20) for two hours.
Antibody 1: SY0716, Rabbit; dissolve 40 μl Antibody in 20 ml PBST) overnight at room temperature (1:500).
Rinse membrane with PBS-T and wash next 3×20' with PBST buffer.
Antibody 2: ECL Plex Goat Anti-Rabbit IgG Cy3 (GE Healthcare); dissolve 10 μl ECL Plex in 25 ml PBST, keep in dark) 1 hour. (1:2500)
Rinse membrane 4 times and wash next 2×10' in PBST
Wash 2×10' in PBS An image was made of the membrane using the Typhoon 9200 (670 BP 30, green (532 nm), PMT 450V, 100 micron).
Molecular Biology Techniques In the examples herein, using molecular biology techniques known to the skilled person (see: Sambrook & Russell, *Molecular Cloning: A Laboratory Manual*, 3rd Ed., CSHL Press, Cold Spring Harbor, N.Y., 2001), several genes were over expressed and others were down regulated as described below.

Figure 6:
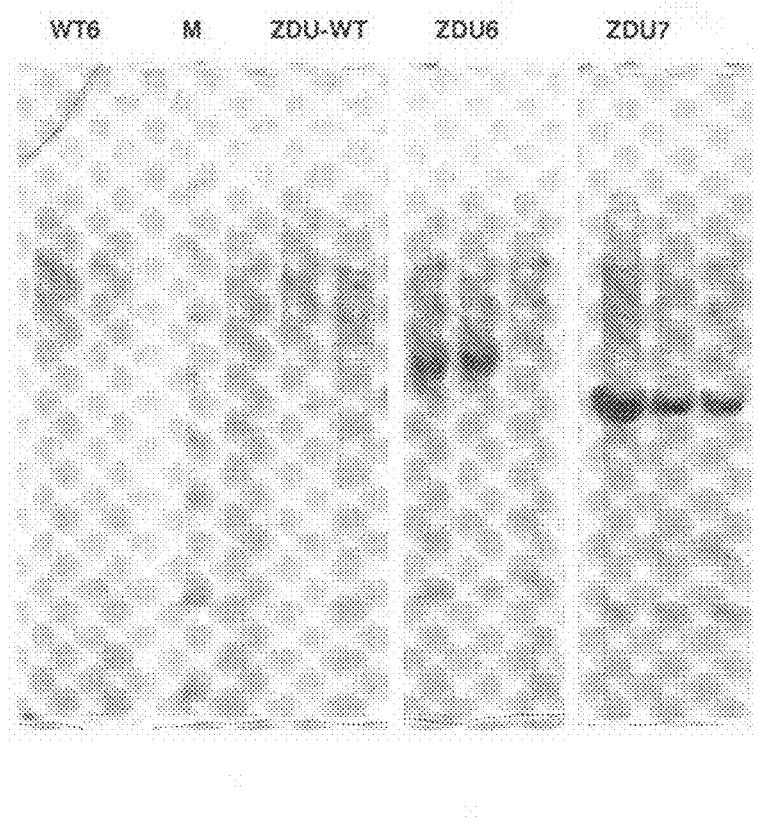
FIG. 6 depicts SDS-PAGE analysis of culture broth of *A. niger* WT6 and ZDU strains after 4 days of fermentation expressing variant ZDU constructs, all under control of the glaA promoter. Details about the different constructs and ZDU proteins expressed can be found in Table 6. For all transformant groups indicated, three transformants were isolated and cultivated independently.

All gene replacement vectors described and used, were designed according to known principles and constructed according to routine cloning procedures. In essence, these vectors comprise approximately 1-2 kb flanking regions of the respective ORF sequences, to target for homologous recombination at the predestined genomic loci. In addition, they contain the *A. nidulans* bi-directional amdS selection marker for transformation, in-between direct repeats. The method applied for gene deletion in all examples herein uses linear DNA, which integrates into the genome at the homologous locus of the flanking sequences by a double cross-over, thus substituting the gene to be deleted by the amdS gene. After transformation, the direct repeats allow for the removal of the selection marker by a (second) homologous recombination event. The removal of the amdS marker can be done by plating on fluoro-acetamide media, resulting in the selection of marker-gene-free strains. Using this strategy of transformation and subsequent counter-selection, which is also described as the "MARKER-GENE FREE" approach in EP 0 635 574, the amdS marker can be used indefinitely in strain modification programs. The general procedure for gene disruption is depicted in FIG. 6 of WO2006040312. The general design of deletion vectors was previously described in EP635574B and WO 98/46772 and the use of general cloning vector pGBDEL for constructing deletion vectors and the counter-selection procedure were a.o. described in WO06/040312.

Examples of the general design of expression vectors and specifically pGBFIN-expression vectors for gene over expression, transformation, use of markers and selective media can be found in WO199846772, WO199932617, WO2001121779, WO2005095624, EP 635574B and WO2005100573.
Shake Flask Fermentations

*A. niger* strains were pre-cultured in 20 ml CSL pre-culture medium (100 ml flask, baffle) as described in the Examples: "*Aspergillus niger* shake flask fermentations" section of WO 99/32617. After growth for 18-24 hours at 34° C. and 170 rpm, 10 ml of this culture is transferred to Fermentation Medium (FM). Fermentation in FM is performed in 500 ml flasks with baffle with 100 ml fermentation broth at 34° C. and 170 rpm for the number of days indicated, generally as described in WO99/32617.

The CSL medium consisted of (in amount per liter): 100 g Corn Steep Solids (Roquette), 1 g $NaH_2PO_4*H_2O$, 0.5 g $MgSO_4*7H_2O$, 10 g glucose*$H_2O$ and 0.25 g Basildon (antifoam). The ingredients were dissolved in demi-water and the pH was adjusted to pH 5.8 with NaOH or $H_2SO_4$; 100 ml flasks with baffle and foam ball were filled with 20 ml fermentation medium and sterilized for 20 minutes at 120° C.

The fermentation medium (FM) consisted of (in amount per liter): 150 g maltose*$H_2O$, 60 g Soytone (peptone), 1 g $NaH_2PO_4*H_2O$, 15 g $MgSO_4*7H2O$, 0.08 g Tween 80, 0.02 g Basildon (antifoam), 20 g MES, 1 g L-arginine. The ingredients were dissolved in demi-water and the pH was adjusted to pH 6.2 with NaOH or $H_2SO4$; 500 ml flasks with baffle and foam ball were filled with 100 ml fermentation broth and sterilized for 20 minutes at 120° C.

For *K. lactis* shake flask fermentations, a single colony of a *K. lactis* PGE transformant was inoculated into 100 ml (flask) of YEP (4%)-D/MES medium that contained per liter: 10 g yeast extract, 20 g Bacto peptone, 40 g glucose and 100 mM MES pH 6.7. The fermentation was performed at 30° C. in a shake incubator at 280 rpm. Supernatant was collected at day 2 and 3 and further analysed as describe below.

Example 1

Construction of *K. lactis* and *A. niger* Expression Vectors for Wild-Type Enzymes and Enzyme Variants According a Method of the Invention In this example a number of expression vectors were constructed for variants of the enzymes of the invention. All variants for expression in *Kluyveromyces* were cloned in a pKLPGE-vector very similar to the pKLAC2 expression vector (New England Biolabs). The general layout of all pKLPGE-vectors can be found in FIG. 1. All variants for expression in *Aspergillus* were cloned in a pGBFIN-5 or a pGBTOP-expression vector. The construction, general layout and use of these vectors are described in detail in WO199932617.
*K. lactis* Constructs Calf pregastric esterase (PGE) is an industrially interesting enzyme and its full length cDNA sequence was published by Timmermans et. al. (1994, Gene 147: 259-262). For expression of PGE in *Kluyveromyces lactis*, this cDNA sequence was codon pair optimized (SEQ ID No. 1) and prepared synthetically (e.g. DNA2.0, USA, GeneArt, Sloning, Germany). An expression construct containing a fusion with the *K. lactis* α-factor pre(pro-) signal sequence and a KREAEA Kex pre(pro-)-sequence processing site was made. Via HindIII and NotI restriction sites, the synthetic gene was cloned in the *K. lactis* expression vector, yielding pKLPGE-WT (FIG. 1), which also contained an amdS selection marker. In addition, several PGE variants were designed with improved protein features according a method of the invention. These mutants differed from the codon pair optimised wild type PGE enzyme (SEQ ID No. 2) with respect to the number of glycosylation sites and/or with respect to hydrophobicity. The PGE mutant enzyme encoding genes were also codon pair optimized and prepared synthetically, as described above. The variants were cloned into the *K. lactis* expression vector as essentially described before using XhoI and NotI cloning sites. All relevant nucleotide and protein details for PGE constructs can be found in Table 4.

TABLE 4

Overview of wildtype and mutants of PGE enzymes expressed in K. lactis

| Name mutant construct | Nucleotide ref SEQ ID No. | Protein ref SEQ ID No. | Description of construct and modification compared to wildtype native full PGE sequence (SEQ ID NO. 2). (Within brackets corresponding positions in the mature PGE sequence) |
|---|---|---|---|
| pKLPGE-WT | 1 | 2 | Codon pair optimized PGE as fusion with the K. lactis α-factor signal sequence and a KREAEA kex site |
| pKLPGE-8 | 3 | 4 | 1 extra glycosylation site was added by modifying amino acid K98 [79] to N |
| pKLPGE-9 | 5 | 6 | 5 extra glycosylation sites were added by modifying amino acids:<br>A70 [51] to S<br>K98 [79] to N<br>R158 [139] to N and R159 [140] to K<br>H318 [289] to N and P320 [301] to S<br>I361 [342] to T |
| pKLPGE-11 | 7 | 8 | pI shift of 6.96 to 7.74; number of polar residues was increased from 165 to 181 and number of charged amino acids residues from 80 to 91 |
| pKLPGE-12 | 9 | 10 | pI shift from 6.96 to 6.7; number of polar residues was increased from 165 to 188 and number of charged amino acids residues from 80 to 103 |
| pKLPGE-10 | 11 | 2 | PGE variant with native signal sequence fused to α-MAT factor signal pre(pro-)sequence |

A. niger Constructs

Figure 2:
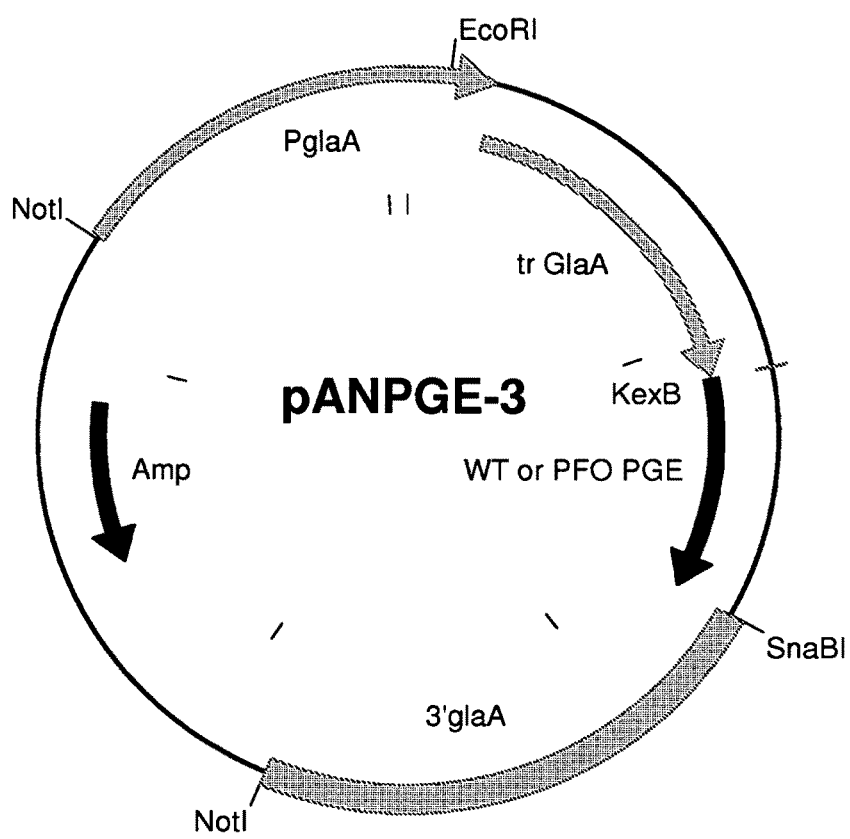
FIG. 2 depicts a plasmid map of expression vector pANPGE-3 (construction described in Example 1).

For expression of Calf pregastric esterase PGE in A. niger, the cDNA sequence was codon pair optimized (SEQ ID No. 12) and prepared synthetically (e.g. DNA2.0, USA, GeneArt, Sloning, Germany). The codon pair optimized PGE encoding gene was prepared synthetically as a fusion to a truncated glucoamylase carrier protein (tAG). The fusion fragment was inserted into a pGBTOP-A. niger expression vector as shown for pANPGE-3 in FIG. 2.

Figure 3:
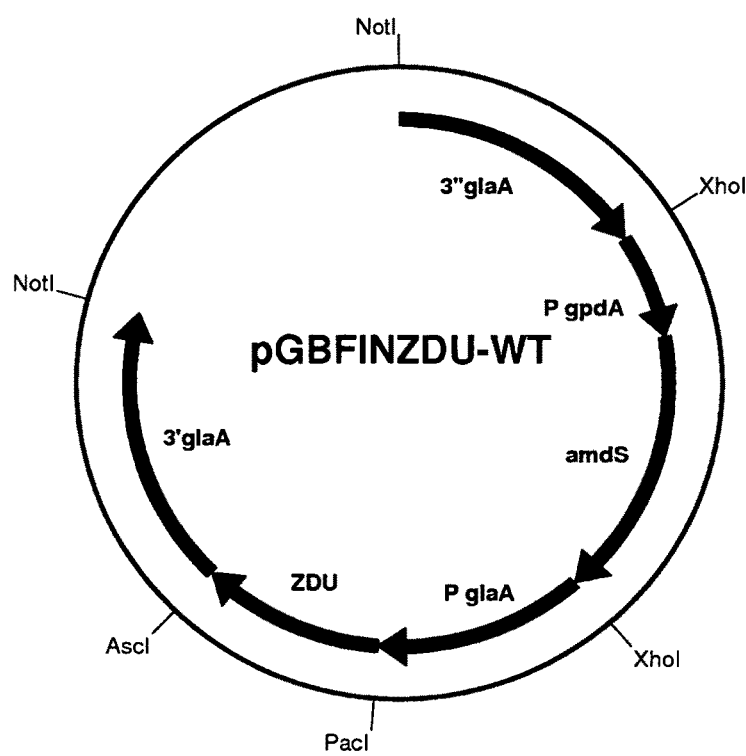
FIG. 3 depicts a plasmid map of expression vector pGBFINZDU-WT (construction described in Example 1).

The wild-type A. niger gene An08g09030 encoding a putative chitinase (ZDU, EC 3.2.1.14, Uniprot A5AB48) was identified in the A. niger genome sequence (EMBL: AM269948-AM270415; Pel et al., "Genome sequencing and analysis of the versatile cell factory Aspergillus niger CBS 513.88". Nat. Biotechnol. 2007 February; 25 (2):221-231). The cDNA sequence of the wild-type chitinase ZDU can be identified as SEQ ID NO. 17 with the deduced wild-type chitinase ZDU protein sequence as SEQ ID NO. 18. The coding sequence of An08g09030 was codon pair optimized (as detailed in WO2008000632) and the translational initiation sequence of the glucoamylase glaA promoter has been modified into 5'-CACCGTCAAA ATG-3' in all expression constructs generated (as also detailed in WO2006/077258). In addition, an optimal translational termination sequence was used, and therefore the wild-type 5'-TGA-3' translational termination sequence was replaced by 5'-TAAA-3' (as detailed in WO2006/077258) in all expression constructs. The optimized chitinase ZDU construct was synthesized completely as PacI-AscI fragment, subcloned and sequence verified. The PacI-AscI restriction sites at the ends of the synthesized fragments were used to allow cloning in the large vector fragment of a PacI-AscI digested pGBFIN-5 expression vector, generating a pGBFINZDU-WT expression vector (FIG. 3).

In addition and in a similar way as for the ZDU chitinase, the Talaromyces emersonii beta-glucosidase (ZTB, EC 3.2.1.21, Uniprot Q8X214) and Phanerochaete chrysosporium endoglucanase (ZTC, EC 3.2.1.4, Uniprot Q66NB6) were codon pair optimized (as detailed in WO2008000632) and with all appropriate control elements cloned as PacI-AscI fragments in pGBFIN-5, generating pGBFINZTB-WT and pGBFINZTC-WT, respectively Protein feature optimizations (PFO) according a method of the invention were applied to the calf pregastric esterase, A. niger chitinase protein sequence, the T. emersonii beta-glucosidase and P. chrysosporium endoglucanase protein sequences. The coding sequences comprising designed variants of the calf pregastric esterase were synthesized completely as EcoRI-SnaBI fragments and sequence verified. The synthesized fragments were cloned in a pGBTOP-vector, generating pANPGE-expression constructs. All relevant nucleotide and protein details for A. niger PGE constructs can be found in Table 5.

TABLE 5

Wild-type and variant enzyme expression constructs for A. niger, references and their properties
Calf pregastric esterase LipF

| Construct | Info | PFO | F-score | SEQ ID DNA | SEQ ID Protein | Details |
|---|---|---|---|---|---|---|
| pANPGE-3 | pI = 6.96 | N | 10.7 | 12 | 2 | CPO gene<br>tAG fusion with Kex site (KR) |
| pANPGE-12 | pI = 4.6 | Y | 7.4 | 13 | 14 | pI shift from 6.96 to 4.6, number of polar residues was increased from 165 to 186 and number of charged amino acids residues from 80 to 88 |

TABLE 5-continued

Wild-type and variant enzyme expression constructs for *A. niger*, references and their properties
Calf pregastric esterase LipF

| Construct | Info | PFO | F-score | SEQ ID DNA | SEQ ID Protein | Details |
|---|---|---|---|---|---|---|
| pANPGE-13 | pI = 4.88 | Y | 7.2 | 15 | 16 | pI shift from 6.96 to 4.88, number of polar residues was increased from 165 to 180 and number of charged amino acids residues from 80 to 83 |

The coding sequences comprising designed variants of the chitinase, the beta-glucosidase and endoglucanase were synthesized completely as PacI-AscI fragments, subcloned and sequence verified. The PacI-AscI restriction sites at the ends of the synthesized fragments were used to allow cloning in the large vector fragment of a PacI-AscI digested pGBFIN-5 expression vector, generating variant pGBFIN-expression vectors. The variant expression constructs were named as described below, and characteristics and reference to respective nucleotide and protein sequences of the pGBFINZDU-constructs can be deduced from Table 6, of the pGBFINZTB-constructs from Table 7 and of the pGBFINZTC-constructs from Table 8.

TABLE 6

Wild-type and variant enzyme expression constructs for *A. niger*, references and their properties
Chitinase *A. niger*

Figure 5:
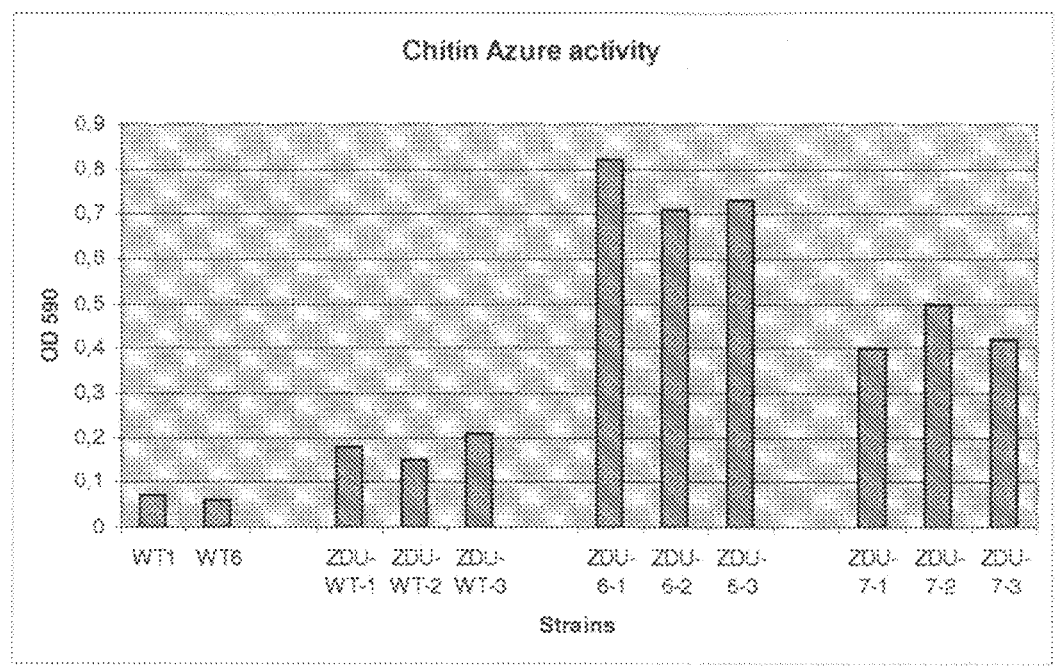
FIG. 5 depicts chitinase activity in culture broth of *A. niger* strains after 3 days of fermentation expressing different ZDU constructs, all under control of the glaA promoter. Depicted is the chitinase activity in culture broth of *A. niger* strains expressing variant SDU constructs wherein signal sequence, N-terminus and protein designs have been modified. Details about the different constructs can be found in Table 6. Relative chitinase activities are depicted as OD590 measurements. For all transformant groups indicated, three transformants were isolated and cultivated independently.

| Construct/Strain | PFO | F-score | SEQ ID DNA | SEQ ID Protein | Example | Activity | Assay | SDS-PAGE |
|---|---|---|---|---|---|---|---|---|
| WT6 | | | | | | low | FIG. 5 | absent |
| ZDU wt | N | 9.7 | 17 | 18 | 4 | low | FIG. 5 | faint |
| ZDU 6 | Y | 5.7 | 19 | 20 | 4 | improved up to 3-fold | FIG. 5 | strong |
| ZDU 7 | Y | 4.0 | 21 | 22 | 4 | improved up to 2-fold | FIG. 5 | strong |

TABLE 7

Wild-type and variant enzyme expression constructs for *A. niger*, references and their properties
Beta-Glucosidase *Talaromyces emersonii*

| Construct/Strain | PFO | F-score | SEQ ID DNA | SEQ ID Protein | Example | pNP activity | Cellobiose activity | SDS-PAGE |
|---|---|---|---|---|---|---|---|---|
| WT6 | | | | | | low | low | absent |
| ZTB wt | N | 11.3 | 23 | 24 | 4 | low | low | absent |
| ZTB 4 | Y | 8.2 | 25 | 26 | 4 | improved up to 20-fold | improved up to 30-fold | strong |

TABLE 8

Wild-type and variant enzyme expression constructs for *A. niger*, references and their properties

| Construct/Strain | PFO | F-score | SEQ ID DNA | SEQ ID Protein | Example | AZO-Cellulose activity | SDS-PAGE |
|---|---|---|---|---|---|---|---|
| WT6 | | | | | | very low | absent |
| ZTC wt | N | 11.3 | 27 | 28 | 4 | very low | absent |
| ZTC 5 | Y | 5.2 | 29 | 30 | 4 | highly improved | strong |

Example 2

Expression and Secretion Analysis of Wild-Type and Protein Feature Optimized PGE's in *K. lactis*

Strains *K. lactis* GG799 or *K. lactis* WT 7 were transformed with all *K. lactis* pKLPGE-constructs (Table 4) that also contained the amdS selection marker. For each of the transformations, 20 colonies were purified on selective medium containing acetamide. Part of the colony was used to generate a DNA template for a PCR reaction to determine the copy number of the PGE construct in each strain. Per construct, 3 transformants, positive in the PCR screen, were further screened on a plate assay containing tributyrine as an enzymatic substrate. For the wt PGE enzyme, no clear activity halo could be detected using the tributyrine plate assay. Also analysis of the supernatant on SDS-PAGE for PGE production did not show a positive result. Surprisingly, for 4 out of the 5 PGE mutants with optimized protein features a clear activity halo could be observed using the tributyrine plate assay. A number of transformants for wt and mutant PGE's were grown in shake flasks and broth and supernatant were examined for lipase activity using pNP-butyrate as a substrate. A summary of various activity assays for the PGE mutants is shown in Table 9.

TABLE 9

Activity tests of PGE wt and PFO variants

| Sample K. lactis Transformant | Day 2 | | | | Day 3 | | | |
|---|---|---|---|---|---|---|---|---|
| | pNP assay (U/ml) | | Plate assay | | pNP assay (U/ml) | | Plate assay | |
| | Broth | Supernatant | Broth | Supernatant | Broth | Supernatant | Broth | Supernatant |
| pKLPGE-WT #1 | <0.12 | <0.1 | − | − | <0.12 | <0.1 | − | − |
| pKLPGE-WT #2 | <0.12 | <0.1 | − | − | <0.12 | <0.1 | − | − |
| pKLPGE-WT #3 | <0.12 | <0.1 | − | − | <0.12 | <0.1 | − | − |
| pKLPGE-8 #1 | <0.2 | <0.1 | +/− | − | 0.24 | <0.1 | ++ | − |
| pKLPGE-8 #2 | <0.2 | <0.1 | + | +/− | 0.22 | <0.1 | ++ | +/− |
| pKLPGE-8 #3 | <0.2 | <0.1 | +/− | − | 0.31 | <0.1 | ++ | − |
| pKLPGE-9 #1 | 0.37 | <0.1 | ++ | ++ | 0.71 | 0.15 | +++ | +++ |
| pKLPGE-9 #2 | <0.2 | <0.1 | ++ | + | 0.23 | <0.12 | ++ | ++ |
| pKLPGE-9 #3 | 0.44 | <0.1 | ++ | +/− | 0.98 | 0.15 | +++ | +++ |
| pKLPGE-11 #1 | <0.2 | <0.1 | + | − | 0.28 | <0.1 | + | +/− |
| pKLPGE-11 #2 | 0.27 | <0.1 | + | − | 0.57 | <0.1 | + | +/− |
| pKLPGE-11 #3 | 0.32 | <0.1 | + | − | 0.84 | <0.1 | + | +/− |
| pKLPGE-12 #1 | 1.4 | 0.28 | ++ | + | 1.9 | 0.41 | ++ | + |
| pKLPGE-12 #2 | 4.0 | 0.67 | ++ | + | 6.6 | 1.2 | + | + |
| pKLPGE-12 #3 | 8.0 | 1.6 | ++ | +/− | 13 | 2.8 | ++ | + |
| pKLPGE-10 #1 | <0.2 | <0.1 | − | − | <0.12 | <0.1 | − | − |
| pKLPGE-10 #2 | <0.2 | <0.1 | − | − | <0.12 | <0.1 | − | − |
| pKLPGE-10 #3 | <0.2 | <0.1 | − | − | <0.12 | <0.1 | − | − |
| GG799/WT 7 | <0.12 | <0.1 | − | − | <0.12 | <0.1 | − | − |

For *K. lactis* pKLPGE-WT (PGE CPO) transformants (various copy number) maximum activity of 0.2 U/ml was obtained. By protein feature optimization of PGE, i.e as expressed in pKLPGE-12, an increase in activity of more than 50× was observed for this PGE mutant. A number of mutants of the PGE-9, PGE-11 and PGE-12 variants were fermented on a larger scale basis, confirming the improved secretion (data not shown). In this example it was shown that by modification of the number of glycosylation sites and by changing the polarity of the hydrophobic enzyme parts exposed to the surface (determined based on PGE modeling) we could dramatically improve the PGE enzyme expression and secretion in *K. lactis*. Furthermore a significant amount of the activity was also found in the supernatant.

Example 3

Expression and Secretion Analysis of Wild-Type and Protein Feature Optimized PGE's in *A. niger*

*A. niger* WT 6 was co-transformed with a pGBAAS construct carrying the *A. nidulans* amdS selection marker and the variant pANPGE-plasmids (Table 5). For each of the transformations, 20 colonies were purified on selective medium containing acetamide and subsequently spore plates were prepared, all as described in WO99/32617. To select *A. niger* transformants that were true co-transformants, e.g. that they contained both PGE and amdS cassettes, a PCR check (not shown). The result showed that at least 50% among the 20 selected transformants contained one or more copies of the PGE expressing construct. These PGE containing transformants were continued with. The spores of the PGE contransformants were harvested and shake flask fermentations were performed in FM medium. At day 2 supernatant samples were collected and screened for lipase activity using the tributyrine plate assay.

In samples harvested from the *A. niger* pANPGE-3 transformants very small activity halos could be detected (data not shown). For pANPGE-12 and pANPGE-13 transformants large activity halos could be detected (data not shown). For each construct pANPGE-3, pANPGE-12 and pANPGE-13, transformants (1-3) that showed the largest halo on the tributyrine plate assay were examined for lipase activity using pNP-butyrate as a substrate. A summary of various activity assays for the PGE mutants is shown in Table 10.

TABLE 10

Wild-type and PFO PGE variants expressed in *A. niger* Calf pregastric esterase LipF

| Construct | PFO | F-score | SEQ ID DNA | SEQ ID Protein | Activity pNP day 2 & 3 supernatant | | Activity Tributyrate plate assay day 2 supernatant |
|---|---|---|---|---|---|---|---|
| pANPGE-3 | N | 10.7 | 12 | 2 | 0.6 | 0.1 | +/− |
| pANPGE-12 | Y | 7.4 | 13 | 14 | 4.7 | 5.8 | ++ |
| pANPGE-13 | Y | 7.2 | 15 | 16 | 5.6 | 7.5 | ++++ |

++++, +++, ++, +, +/−, − corresponded to very large, large, medium, small, not clear and no halo on the tributyrine plate assay, respectively.

Figure 4:
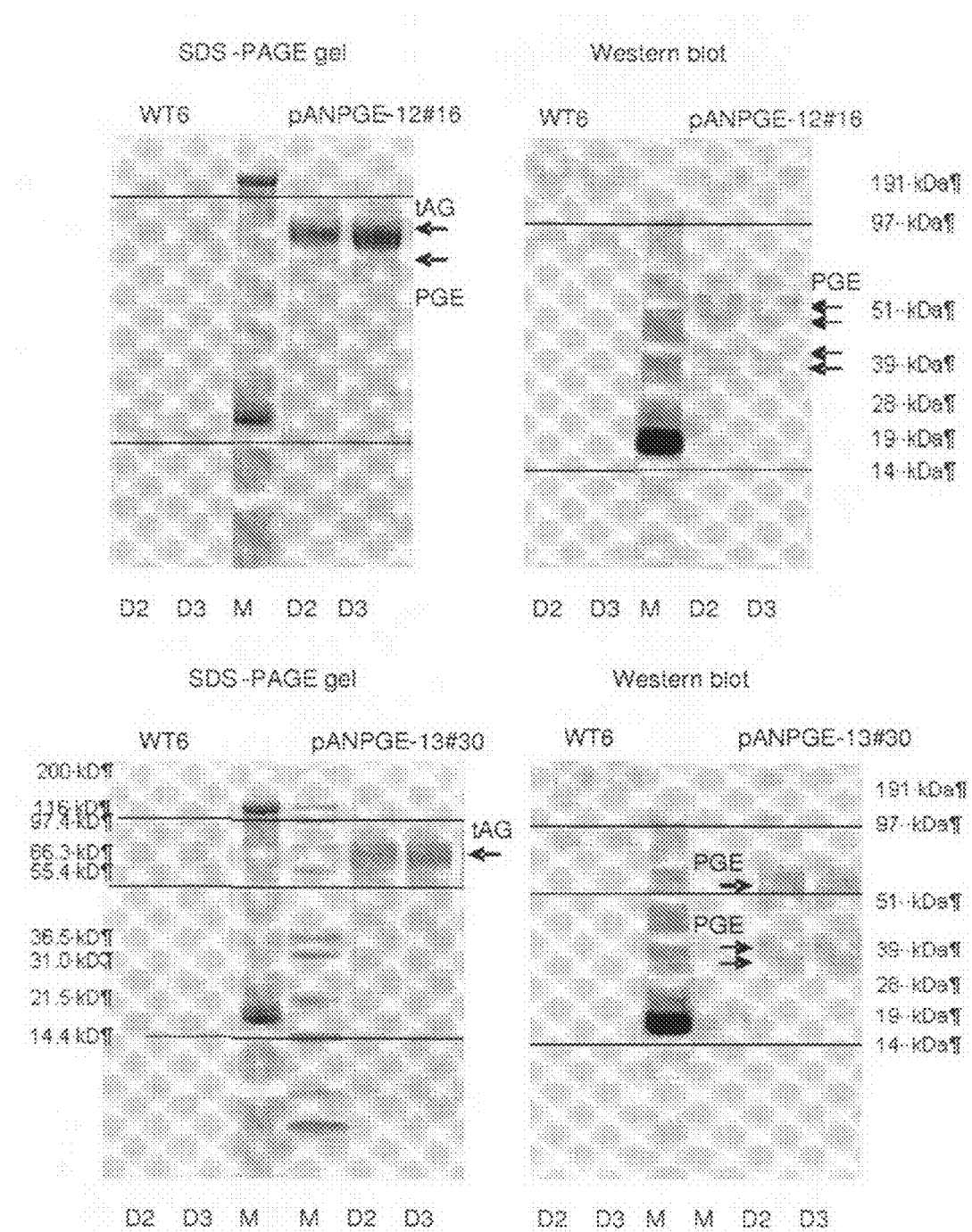
FIG. 4 SDS-PAGE and western blot analysis of *A. niger* WT6 and the PGE mutant transformants pANPGE12#16 (A) and pANPGE13#30 (B). Supernatant of day 2 (D2) and day 3 (D3) of the cultures was analyzed. The horizontal lines that are at the 14 kDa and 97 kDa are for alignment of the SDS-PAGE and Western blot. The marker size on the left-hand side correspond to the SDS-PAGE stained marker and the marker on the right-hand side corresponds to the Western blot marker.

The supernatant samples of WT6 and selected transformants pANPGE-12#16 and pANPGE-13#30 were further analysed on SDS-PAGE gel (Invitrogen) and by western blotting using PGE polyclonal antibodies (see FIG. 4). For the *A.* niger PGE PFO variant of pANPGE-12, a band corresponding to the mature PGE could be detected on the SDS-PAGE gel. Using the PGE polyclonal antibody PGE, cross-hybridizing bands could be detected in supernatants of both transformants. The highest molecular weight band (about 55 kDa) corresponds probably to the mature PGE mutant and the cross-hybridizing bands of the lower molecular weight could be a result of a proteolytic degradation.

It is concluded that by changing the polarity of the enzyme parts exposed to the surface (determined based on PGE modelling) following the rules of protein feature optimisation we could dramatically improve the PGE enzyme expression in *A. niger*. Furthermore high enzymatic activity was also found in the supernatant.

Example 4

Expression of Wild-Type and PFO Optimized Fungal Enzymes in *A. niger*

The pGBFINZDU-, pGBFINZTB- and pGBFINZTC-expression constructs, prepared in Example 1 (super), were introduced by transformation using *A. niger* as described below. In order to introduce the different pGBFINZDU-, pGBFINZTB- and pGBFINZTC-vectors (Table 6, 7 and 8, respectively) in WT 6, a transformation and subsequent selection of transformants was carried out as described in WO1998/46772 and WO1999/32617. In brief, linear DNA of all the pGBFIN-constructs was isolated and used to transform *A. niger* WT 6. Transformants were selected on acetamide media and colony purified according standard procedures. Colonies were diagnosed for integration at the glaA locus and for copy number using PCR. Three independent transformants for each pGBFINZDU-, pGBFINZTB- and pGBFINZTC-construct with similar estimated copy numbers (putative single copy) were selected and named using the number of the transforming plasmid, as for example ZDU-WT-1, ZDU-WT-2, ZDU-WT-3, ZDU-6-1, ZDU-6-2, ZDU-6-3, etc...., respectively.

The selected ZDU-, ZTB- and ZTC-strains and *A. niger* WT6 were used to perform shake flask experiments in 100 ml of the FM medium as described above at 34° C. and 170 rpm in an incubator shaker using a 500 ml baffled shake flask. After day 3, day 4 and day 5 of fermentation, samples were taken to determine the amount of extracellular protein produced by gel electrophoresis and the chitinase activity.

The production of chitinase expressed by each of the transformants of the *A. niger* ZDU-transformants containing the different constructs, was measured in the culture supernatant. The measured chitinase activity levels at day 3 are indicated in FIG. 5. In addition, the culture supernatants sampled at day 4 were analyzed by SDS gel electrophoresis and staining (FIG. 6). From these results, it is clear that an optimized protein features have a positive impact on protein secretion and results in detectable and thus increased protein expression levels and increased activity levels for the chitinase enzyme. Results have been summarized in Table 6.

Figure 7:
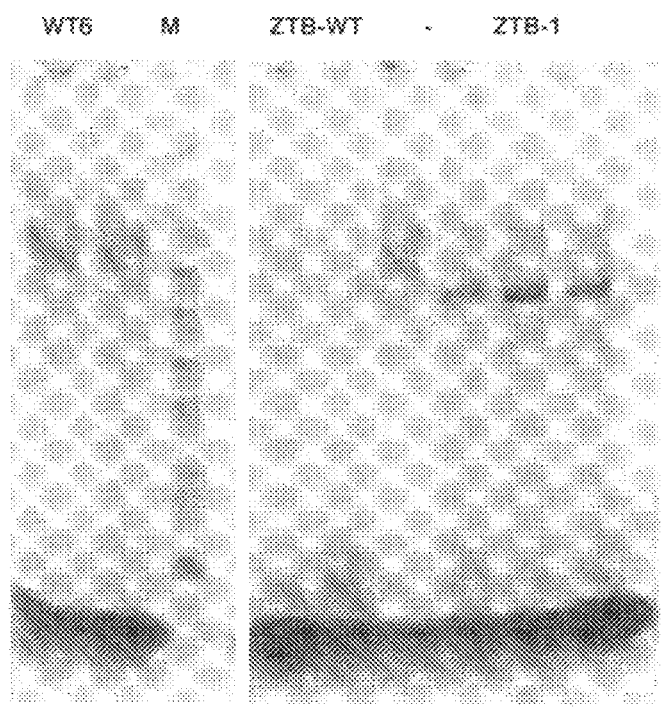
FIG. 7 depicts SDS-PAGE analysis of culture broth of *A. niger* WT6 and ZTB-strains after 4 days of fermentation expressing variant ZTB constructs, all under control of the glaA promoter. Details about the different constructs and ZTB proteins expressed can be found in Table 7. For all transformant groups indicated, three transformants were isolated and cultivated independently.

The production of beta-glucosidase expressed by each of the transformants of the *A. niger* ZTB-transformants containing the different constructs, was measured in the culture supernatant. The culture supernatants sampled at day 4 were analyzed by SDS gel electrophoresis and staining (FIG. 7). From these results, it is clear that an optimized protein features have a positive impact on protein secretion and results in detectable and thus increased protein expression levels for the beta-glucosidase enzyme. In addition the activity in the supernatant sampled at day 3 was determined at pH=4.5 and 40° C. using pNP-β-glucopyranoside as a substrate. The supernatant of the beta-glucosidase which had been subjected to protein feature optimization showed an activity increase of up to 20-fold compared to the parent beta-glucosidase encoded by a codon optimised gene. The background beta-glucosidase activity which is measured for the empty host was two- to four-fold lower than from the parent beta-glucosidase encoded by a codon optimised gene. The activity was also measured using cellobiose as a substrate at pH=4.5 and 40° C. The measured increase in activity was at least 30-fold compared to the parent beta-glucosidase encoded by a codon optimized gene (empty host strains show three- to ten-fold lower than from the parent beta-glucosidase encoded by a codon optimized gene). Results have been summarized in Table 7.

Figure 8:
FIG. 8 depicts SDS-PAGE analysis of culture broth of *A. niger* WT6 and ZTC-strains after 5 days of fermentation expressing variant ZTC constructs, all under control of the glaA promoter. Details about the different constructs and ZTC proteins expressed can be found in Table 8. For the ZTC-WT transformant group indicated, three transformants were isolated and cultivated independently, for the other two strain types two strains.

The production of endo-glucanase expressed by each of the transformants of the *A. niger* ZTC-transformants containing the different constructs, was measured in the culture supernatant. The culture supernatants sampled at day 4 were analyzed by SDS gel electrophoresis and staining (FIG. 8). From these results, it is clear that optimized protein features have a positive impact on protein secretion and results in detectable and thus increased protein expression levels for the endoglucanase enzyme. The endo-glucanase activity in the supernatant sampled at day 3 was determined at pH=4.5 and 40° C. using AZO-CM-cellulose as a substrate. The supernatant of the endo-glucanase which had been subjected to protein feature optimization showed an increase in activity of over 350-fold compared the codon optimized gene expressed in the same host. It should be noted that due to the very low background activity in the empty strain (undetectable by SDS-PAGE), the increase in activity was expressed in such high figure. For the endo-glucanase encoded by a codon optimized gene the measured activity was about the background activity observed for the empty host strain. Results have been summarized in Table 8.

Clearly, these examples show how a method of the invention for protein feature optimization can be used for improved secretion and production of proteins and enzymes of interest. Additionally, these results indicate that a method of the invention can be broadly applied to improve protein expression in a host, although the expression construct and host has already several other optimizations, such as for example a strong promoter, an improved translation initiation sequence, an improved translational termination sequence, an optimized codon and codon pair usage and/or an improved host for protein expression.

The invention claimed is:

1. A method for the production of a polypeptide of interest by a eukaryotic host cell, which method comprises modifying a value of a set of relevant protein features in an amino acid backbone of the polypeptide to fall within an optimal range or to become closer to an optimal value for one or more protein features in the eukaryotic host, wherein said protein features are properties that can be calculated from the protein amino acid sequence and DNA sequence, the method comprising the steps of:
(i) providing a sequence for the polypeptide of interest,
(ii) determining an optimal range and an optimal value for one or more protein features in the eukaryotic host,
(iii) determining a set of relevant protein features in the eukaryotic host, which features will improve secretion of the polypeptide by the eukaryotic host if one or more of said relevant features is modified in the amino acid backbone of the polypeptide of interest, and
(iv) modifying the sequence for the polypeptide of interest such that the value of the relevant protein features falls within the optimal range or closer to the optimal value as determined in (i), and
(v) producing the modified polypeptide by the eukaryotic host cell,
wherein said method improves the secretion of said polypeptide of interest,
wherein the specificity and/or specific activity of the polypeptide after said modifying substantially remains the same as before improvement of the secretion,
wherein (i) and (ii) may be performed in any order,
wherein the relevant set of protein features is determined by:
a. collecting or creating a dataset S, which contains secretion levels of a suitable amount of proteins in a certain eukaryotic host and amino acid and DNA sequences thereof;
b. calculating values of protein features (F) for all proteins in the dataset S;
c. using a statistical classification method to select a subset of protein features (Fs) that gives the best performance of a statistical classifier to distinguish between secreted proteins (S+) and non-secreted proteins (S−) in the dataset S, according to a suitably defined classifier performance criterion; and
wherein the optimal range or the optimal value of protein features for a eukaryotic host is determined by:
d. collecting or creating a dataset S, which comprises secretion levels of a suitable amount of proteins in a certain eukaryotic host and amino acid and DNA sequences thereof;
e. calculating protein features (F) for all proteins in the dataset S;
f. determining an optimal value (F opt) for each feature for the eukaryotic host by fitting a probability distribution for each protein feature calculated from secreted proteins (S+) such that the distribution of the feature values is well described by the chosen probability distribution;
g. determining an optimal range of each feature for the eukaryotic host;

wherein the relevant set of protein features is selected from the group consisting of: the number of amino acids, molecular weight, isoelectric point, net charge at a specific pH, GRAVY score, aliphatic index, instability index, compositional features, atomic composition of C, H, N, O, S atoms, amino acid frequency, dipeptide frequency, tripeptide frequency, acidic amino acid frequency, aliphatic amino acid frequency, aromatic amino acid frequency, basic amino acid frequency, local features, localization features, glycosylation pattern and/or charged amino acid frequency.

2. The method according to claim 1, wherein the protein features are calculated from a set of mature protein sequences.

3. A method for the production of a polypeptide of interest by a eukaryotic host cell, said method comprising:
   (i) providing a sequence for the polypeptide of interest,
   (ii) calculating values of protein features for the polypeptide,
   (iii) determining if one or more values of protein features of the polypeptide are outside an optimal range or substantially deviate from an optimal value for the eukaryotic host,
   (iv) changing an amino acid sequence of the provided sequence for the polypeptide, such that the value of one or more protein features derived from the amino acid sequence (Fs_AA) of the polypeptide falls within an optimal range or is shifted towards an optimal value by a suitable amount, defined by relative improvement (RI) or normalized relative improvement (RIN) wherein the change defined by RI or RIN is optionally more than 10%,
   (v) producing the modified polypeptide by the eukaryotic host cell,
   wherein the optimal range or the optimal value of protein features for a eukaryotic host is determined by:
      a. collecting or creating a dataset S, which comprises secretion levels of proteins in a certain eukaryotic host and amino acid and DNA sequences thereof;
      b. calculating protein features (F) for all proteins in the dataset S;
      c. determining an optimal value (F opt) for each feature for the eukaryote host by fitting a probability distribution for each protein feature calculated from secreted proteins (S+) such that the distribution of the feature values is well described by the chosen probability distribution;
      d. determining an optimal range of each feature for the eukaryote host;
   wherein said relevant protein features (Fs_AA) are selected from the group consisting of: basic amino acid frequency, polar amino acid frequency, non-polar amino acid frequency, tiny amino acid frequency, small amino acid frequency, charged amino acid frequency, net charge (at pH 7.2), isoelectric point, frequency of asparagine, arginine, isoleucine, cysteine, histidine, glutamine, valine, lysine, glycine, threonine and leucine, turn as calculated by Garnier, PEST motif as calculated by EPESTFIND, local feature (LF) values for pi, including LF1 and LF6, LF values for Gravy score, including LF2 and LF4, LF values for aroma score, including LF3, LF4 and LF6, atomic composition w.r.t, sulphur (S) and localization features;
   wherein the specificity and/or specific activity of the polypeptide after said modifying substantially remains the same as before improvement of the secretion, and wherein secretion of said polypeptide of interest by a eukaryotic host is improved.

4. The method according to claim 1 wherein the sequence of the polypeptide of interest is modified with respect to one or more of the following features: basic amino acid frequency, polar amino acid frequency, non-polar amino acid frequency, tiny amino acid frequency, small amino acid frequency, charged amino acid frequency, net charge at pH 7.2, isoelectric point, frequency of Asn, Arg, Ile, Cys, His, Gln, Val, Lys, Gly, Thr and Leu, respectively, localization features, turn as calculated by Garnier, PEST motif as calculated by EPESTFIND, LF values for pI, LF values for Gravy score, LF values for aroma score, and/or sulphur (S) composition.

5. The method according to claim 1 wherein the sequence of the polypeptide of interest is modified with respect to one or more features selected from the group consisting of: pI, net charge, net charge per length, net positive charge per length, net negative charge per length, total charge per length, gravy score, aroma score, aliphatic index, tiny amino acid frequency, small amino acid frequency, polar amino acid frequency, non-polar amino acid frequency, charged amino acid frequency, acidic amino acid frequency, basic amino acid frequency, aliphatic amino acid frequency, and frequency of Ala, Arg, Asn, Asp, Cys, Gln, Glu, Gly, His, Ile, Leu, Lys, Met, Phe, Pro, Ser, Thr, Trp, Tyr and Val, respectively.

6. The method according to claim 1 wherein the sequence of the polypeptide of interest is modified with respect to one or more features selected from the group consisting of: pI, net charge (pH7.2), net charge (pH7.2) per length, net positive charge (pH7.2) per length, total charge (pH7.2) per length, aliphatic index, small amino acid frequency, polar amino acid frequency, non-polar amino acid frequency, charged amino acid frequency, amino acid frequency, and frequency of Arg, Gln, Glu, Lys, Phe and Thr, respectively.

7. The method according to claim 1 wherein the sequence of the polypeptide of interest is modified with respect to one or more features selected from the group consisting of: glycosylation sites, gravy score, polar amino acid frequency, non-polar amino acid frequency, charged amino acid frequency, acidic amino acid frequency, basic amino acid frequency, and frequency of Glu, Lys and Thr, respectively.

8. The method according to claim 1 wherein at least 5% of the amino acids are modified.

9. The method according to claim 1 wherein at least 5 of the amino acids are modified.

10. The method according to claim 1, wherein at least 2 features are modified.

11. The method according to claim 1, wherein at least 2 features are improved and less than 10 features are worsened.

12. The method according to claim 1 wherein the sequence of the mature peptide is modified.

13. The method according to claim 1, wherein the eukaryotic cell is a yeast cell or a filamentous fungal cell.

14. The method according to claim 1, wherein the polypeptide is a mammalian or a bacterial polypeptide.

15. The method according to claim 1, wherein improvement of secretion is measured by increase in activity and wherein the activity in the extracellular medium is increased by at least 5%.

16. The method according to claim 1, wherein the polypeptide is an enzyme, a membrane protein, a hormone or a receptor.

* * * * *